(12) United States Patent
Bennani et al.

(10) Patent No.: US 8,716,324 B2
(45) Date of Patent: *May 6, 2014

(54) TRICYCLIC INDENO-PYRROLE DERIVATIVES AS SEROTONIN RECEPTOR MODULATORS

(75) Inventors: Youssef L. Bennani, Boston, MA (US); Bayard Huck, Sudbury, MA (US); Michael J. Robarge, Burton, OH (US)

(73) Assignee: Athersys, Inc., Clevelend, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/526,249

(22) Filed: Jun. 18, 2012

(65) Prior Publication Data

US 2012/0252859 A1 Oct. 4, 2012

Related U.S. Application Data

(63) Continuation of application No. 13/071,732, filed on Mar. 25, 2011, now Pat. No. 8,232,311, which is a continuation of application No. 12/478,362, filed on Jun. 4, 2009, now Pat. No. 7,935,830, which is a continuation of application No. 11/189,952, filed on Jul. 26, 2005, now abandoned.

(60) Provisional application No. 60/592,047, filed on Jul. 29, 2004.

(51) Int. Cl.
*A61K 31/403* (2006.01)
*C07D 209/70* (2006.01)
*C07D 409/04* (2006.01)

(52) U.S. Cl.
CPC ............ *C07D 209/70* (2013.01); *C07D 409/04* (2013.01)
USPC .......................................... 514/411; 548/427

(58) Field of Classification Search
CPC ............................. C07D 209/70; C07D 409/04
See application file for complete search history.

(56) References Cited

U.S. PATENT DOCUMENTS 4,622,405 A * 11/1986 DeBernardis et al. ........ 548/427
7,304,081 B2 * 12/2007 Yao et al. ...................... 514/370

* cited by examiner

*Primary Examiner* — Noble Jarrell
*Assistant Examiner* — Valerie Rodriguez-Garcia
(74) *Attorney, Agent, or Firm* — Wood, Philips, Katz, Clark & Mortimer

(57) ABSTRACT

The present invention generally relates to a series of compounds, to pharmaceutical compositions containing the compounds, and to use of the compounds and compositions as therapeutic agents. More specifically, compounds of the present invention are tricyclic indeno-pyrrole compounds. These compounds are serotonin receptor (5-HT) ligands and are useful for treating diseases, disorders, and conditions wherein modulation of the activity of serotonin receptors (5-HT) is desired (e.g. anxiety, depression and obesity).

6 Claims, No Drawings

US 8,716,324 B2

TRICYCLIC INDENO-PYRROLE DERIVATIVES AS SEROTONIN RECEPTOR MODULATORS

This application is a continuation of U.S. patent application Ser. No. 13/071,732, filed on Mar. 25, 2011, which is a continuation of U.S. patent application Ser. No. 12/478,362, filed on Jun. 4, 2009, which is a continuation of U.S. patent application Ser. No. 11/189,952, filed on Jul. 26, 2005 and which claims a priority of U.S. Provisional Patent Application Ser. No. 60/592,047, filed on Jul. 29, 2004. The disclosures of all the above-identified applications are hereby incorporated by reference in their entirety.

FIELD OF THE INVENTION

The present invention generally relates to a series of compounds, to pharmaceutical compositions containing the compounds, and to use of the compounds and compositions as therapeutic agents. More specifically, compounds of the present invention are tricyclic indeno-pyrrole compounds. These compounds are serotonin receptor (5-HT) ligands and are useful for treating diseases, disorders, and conditions wherein modulation of the activity of serotonin receptors (5-HT) is desired (e.g. addiction, anxiety, depression and obesity).

BACKGROUND OF THE INVENTION

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, addiction and schizophrenia. Serotonin also plays an important role in peripheral systems, such as the gastrointestinal system, where it has been found to mediate a variety of contractile, secretory, and electrophysiologic effects.

Because of the broad distribution of serotonin within the body, there is a need for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism, and Huntington's chorea), and chemotherapy-induced vomiting.

The major classes of serotonin receptors ($5\text{-HT}_{1-7}$) contain one to seven separate receptors that have been formally classified. See Glennon, et al., *Neuroscience and Behavioral Reviews*, 1990, 14, 35; and D. Hoyer, et al. *Phannacol. Rev.* 1994, 46, 157-203.

For example, the $5\text{-HT}_2$ family of receptors contains $5\text{-HT}_{2a}$, $5\text{-HT}_{2b}$, and $5\text{-HT}_{2c}$ subtypes, which have been grouped together on the basis of primary structure, secondary messenger system, and operational profile. All three $5\text{-HT}_2$ subtypes are G-protein coupled, activate phospholipase C as a principal transduction mechanism, and contain a seven-transmembrane domain structure. There are distinct differences in the distribution of the three $5\text{-HT}_2$ subtypes in a mammal. The $5\text{-HT}_{2b}$ and $5\text{-HT}_{2a}$ receptors are widely distributed in the peripheral nervous system, with $5\text{-HT}_2$ also found in the brain. The $5\text{-HT}_{2b}$ receptor has been found only in the central nervous system, being highly expressed in many regions of the human brain. See G. Baxter, et al. *Trends in Pharmacol. Sci.* 1995, 16, 105-110.

Subtype $5\text{-HT}_{2a}$ has been associated with effects including vasoconstriction, platelet aggregation, and bronchoconstriction, as well as certain CNS effects, while subtype $5\text{-HT}_{2c}$ has been associated with diseases that include depression, anxiety, obsessive compulsive disorder, addiction, panic disorders, phobias, psychiatric syndromes, and obesity. Very little is known about the pharmacologic role of the $5\text{-HT}_{2b}$ receptor. See F. Jenck, et al., *Exp. Opin. Invest. Drugs*, 1998, 7, 1587-1599; M. Bos, et al., *J. Med. Chem.*, 1997, 40, 2762-2769; J. R. Martin, et al., *The Journal of Pharmacology and Experimental Therapeutics*, 1998, 286, 913-924; S. M. Bromidge, et al., 1. *Med. Chem.*, 1998, 41,1598-1612; G. A. Kennett, *Drugs*, 1998, 1, 4, 456-470; and A. Dekeyne, et al., *Neuropharmacology*, 1999, 38, 415-423.

U.S. Pat. Nos. 4,622,405; 5,049,564 and 5,244,888 and WO 90/06927 disclose various indeno-pyrrole derivatives.

SUMMARY OF THE INVENTION

The present invention is directed to compounds of the formula:

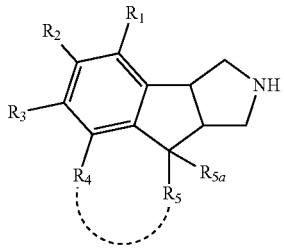

where $R_1$ is selected from the group consisting of H, halogen, $C_{1-10}$alkyl, $C_{2-10}$ alkenyl, $C_{2-10}$ alkynyl, perhaloalkyl, CN, $N(R_6)_2$, $SR_6$, $CON(R_6)_2$, $NR_6COR_7$, $NR_6CO_2R_7$, $SO_2N(R_6)_2$, $NR_6SO_2R_7$, aryl, heteroaryl, $C_{1-10}$alkylaryl, and $C_{1-10}$alkylheteroaryl;

$R_2$, $R_3$ and $R_4$ are independently selected from the group consisting of H, halogen, $C_{1-10}$alkyl, $C_{2-10}$ alkenyl, $C_{2-10}$ alkynyl, perhaloalkyl, CN, $OR_6$, $N(R_6)_2$, $SR_6$, $OCOR_7$, $CON(R_6)_2$, $NR_6COR_7$, $NR_6CO_2R_7$, $SO_2N(R_6)_2$, $NR_6SO_2R_7$, aryl, heteroaryl, $C_{1-10}$ alkylaryl, and $C_{1-10}$alkylheteroaryl or $R_2$ and $R_3$ together with the ring to which they are attached form a 5 to 7 membered carbocyclic or heterocyclic ring;

$R_5$ is selected from the group consisting of H, $C_{1-10}$ alkyl, $C_{2-10}$ alkenyl, $C_{2-10}$ alkynyl, perhaloalkyl, CN, $OR_6$, $N(R_6)_2$, $SR_6$, $OCOR_7$, $CON(R_6)_2$, $NR_6COR_7$, $NR_6CO_2R_7$, $NR_6SO_2R_7$, aryl, heteroaryl, $C_{1-10}$alkylaryl, and $C_{1-10}$ alkylheteroaryl, or $R_4$ and $R_5$ together with the ring to which they are attached form a 6 to 8 membered aryl or heteroaryl ring;

$R_{5a}$ is H; or $R_5$ and $R_{5a}$ taken together form a cyclopropane ring;

$R_6$ is selected from the group consisting of H, $C_{1-10}$, alkyl, $C_{2-10}$ alkenyl, $C_{2-10}$ alkynyl, perhaloalkyl, $C_{1-10}$ alkyl-O—$C_{1-10}$ alkyl, aryl, heteroaryl, $C_{1-10}$alkyl-0-aryl, $C_{1-10}$ alkyl-O-heteroaryl, $C_{1-10}$ alkylaryl, and $C_{1-10}$ alkylheteroaryl; and $R_7$ is selected from the group consisting of $C_{1-10}$ alkyl, $C_{2-10}$ alkenyl, $C_{2-10}$ alkynyl, perhaloalkyl, $C_{1-10}$alkyl-O—$C_{1-10}$ alkyl, aryl, heteroaryl, $C_{1-10}$alkyl-O-aryl, $C_{1-10}$alkyl-O-heteroaryl, $C_{1-10}$ alkylaryl, and $C_{1-10}$ alkylheteroaryl;

provided that if $R_1$, $R_2$, $R_5$ and $R_{5a}$ are H, then $R_3$ and/or $R_4$ must be H and the pharmaceutically acceptable salts thereof.

Included herein are the various stereoisomers of the compounds of Formula (I).

Another embodiment of the present invention provides a pharmaceutical composition comprising a compound of Formula (I), or a pharmaceutically acceptable salt thereof, and a pharmaceutically acceptable carrier.

Still another embodiment of the present invention provides a method of treating a disease, disorder and/or condition in a mammal (e.g., animal or human), wherein a 5-HT$_{2c}$ receptor is implicated and modulation of a 5-HT$_{2c}$ function is desired. The method comprises administering a therapeutically effective amount of a compound of Formula (I), or a pharmaceutically acceptable salt thereof, to the mammal.

Yet another embodiment of the present invention comprises a method of modulating 5-HT receptor function with an effective amount of compound of Formula (I), or a pharmaceutically acceptable salt thereof.

A further embodiment of the present invention provides a method of treating or preventing diseases, disorders, and/or conditions of the central nervous system. The method comprises administering a therapeutically effective amount of a compound of Formula (I), or a pharmaceutically acceptable salt thereof, to the mammal.

Specific diseases, disorders and/or conditions for which compounds of the Formula (I) may have activity include cardiovascular disorders, obesity, depression, schizophrenia, anxiety, obsessive compulsive disorder, addiction, panic disorders, sleep disorders, migraine, Type II diabetes, epilepsy, phobias and psychiatric syndromes.

DETAILED DESCRIPTION OF THE INVENTION

The following definitions are used, unless otherwise described:

As used herein, the term "alkyl" includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$-$C_8$ hydrocarbon group, such as cyclopropyl, cyclobutyl, cyclopentyl, and cyclohexyl. Reference to an individual group or moiety, such as "propyl," embraces only the straight chain group or moiety. A branched chain isomer, such as "isopropyl," is specifically referred to.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl radical containing from 2 to 10 carbon atoms. Examples of such radicals include, but are not limited to, ethynyl, propynyl, propargyl, butynyl, hexynyl, decynyl and the like.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "halo" is defined herein to include fluoro, chloro, bromo, or iodo. Similarly, the term "halogen" is defined herein to include fluorine, chlorine, bromine, and iodine.

The term "amino", alone or in combination, includes the group —NH$_2$ or —NR$_a$R$_b$ wherein R$_a$ and R$_b$ are independently hydrogen, alkyl or aryl.

The term "aryl," alone or in combination, is defined herein as a monocyclic or bicyclic aromatic group (e.g., phenyl or naphthyl) that can be unsubstituted or substituted, for example, with one or more, and in particular one to three of the following substituents selected from the group consisting of H, halo, CN, NO$_2$, CF$_3$, N$_3$, C$_{1-6}$ alkyl, OH, NR$^a$R$^b$, OC$_{1-6}$ alkyl, OR$^a$, C(=O)NR$^a$R$^b$, C(=S)NR$^a$R$^b$, tetrazoyl, triazoyl, amidinyl, guanidinyl, thioguanidinyl, cyanoguanadinyl, and aryl. Generally, "aryl" denotes a phenyl group, or an ortho-fused bicyclic carbocyclic group having nine to ten ring atoms in which at least one ring is aromatic (e.g. naphthyl or tetrahydronaphthyl). The term "aryl" also is abbreviated in the various chemical structures as "Ar."

The term "carbocylic" includes any closed ring of carbon atoms, including alicyclic and aromatic structures.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl. Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, 1,3-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group consisting of non-peroxide oxygen, sulfur, and N(Z) wherein Z is absent or is H, O, C$_{1-4}$alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The term "Het" generally represents a heterocyclic group, saturated or partially unsaturated, containing at least one heteroatom selected from the group consisting of oxygen, nitrogen, and sulfur, and optionally substituted with C$_{1-6}$alkyl or C(=O)OR$^b$. Typically "Het" is a monocyclic, bicyclic, or tricyclic group containing one or more heteroatoms selected from the group consisting of oxygen, nitrogen, and sulfur. A "Het" group also can contain an oxo group (=O) attached to the ring. Nonlimiting examples of Het groups include 1,3-dihydrobenzofuran, 1,3-dioxolane, 1,4-dioxane, 1,4-dithiane, furanyl, imidazolyl, 2H-pyran, 2-pyrazoline, 4H-pyran, chromanyl, imidazolidinyl, imidazolinyl, indolinyl, isochromanyl, isoindolinyl, morpholine, oxazolyl, piperazinyl, piperidine, piperidynyl, pyrazolidine, pyrimidinyl, pyrazolidinyl, pyrazolinyl, pyrrolidine, pyrroline, quinuclidine, and thiomorpholine.

Preferably, R$_1$ is C$_{1-5}$ alkyl, halogen, CF$_3$, aryl, heteroaryl or H; R$_2$, R$_3$ and R$_4$ are independently C$_{1-5}$alkyl, —O—R$_6$, halogen, CF$_3$, aryl, heteroaryl or H; R$_5$ is C$_{1-5}$-alkyl, —OR$_6$ or C$_{2-6}$alkene; and R$_6$ is C$_{1-5}$alkyl or H.

Presently preferred compounds include:
5-Methoxy-8-methyl-1,2,3,3a,8,8a-hexahydroindeno[1,2-c]pyrrole;
5-Hydroxy-8-methyl-1,2,3,3a,8,8a-hexahydroindeno[1,2-c]pyrrole;
5-Methoxy-6-chloro-8-methyl-1,2,3,3a,8,8a-hexahydroindeno[1,2-c]pyrrole;
5-Hydroxy-6-chloro-8-methyl-1,2,3,3a,8,8a-hexahydroindeno[1,2-c]pyrrole;
6-Chloro-8-methyl-1,2,3,3a,8,8a-hexahydroindeno[1,2-c]pyrrole;
5-(4-Fluorobenzyloxy)-6-chloro-8-methyl-1,2,3,3a,8,8a-hexahydroindeno[1,2-c]pyrrole;
5-Benzyloxy-6-chloro-8-methyl-1,2,3,3a,8,8a-hexahydroindeno[1,2-c]pyrrole;
5-(2-Fluorobenzyloxy)-6-chloro-8-methyl-1,2,3,3a,8,8a-hexahydroindeno[1,2-c]pyrrole;
5-(3-Fluorobenzyloxy)-6-chloro-8-methyl-1,2,3,3a,8,8a-hexahydroindeno[1,2-c]pyrrole;
1,2,3,3a,8,8a-Hexahydroindeno[1,2-c]pyrrole;
6-Chloro-1,2,3,3a,8,8a-hexahydroindeno[1,2-c]pyrrole;
6,7-Dichloro-8-methyl-1,2,3,3a,8,8a-hexahydroindeno[1,2-c]pyrrole;
4,5-Dimethoxy-6-chloro-8-methyl-1,2,3,3a,8,8a-hexahydroindeno[1,2-c]pyrrole;
4,6-Dichloro-5-Methoxy-8-methyl-1,2,3,3a,8,8a-hexahydroindeno[1,2-c]pyrrole; and
6-(2,6-Difluorophenyl)-1,2,3,3a,8,8a-hexahydroindeno[1,2-c]pyrrole.

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, furmaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfumingagents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The compounds of the present invention may be prepared by the procedures set forth in Schemes 1, 2 and 3. The general analytical conditions set forth after the Schemes were utilized in all examples.

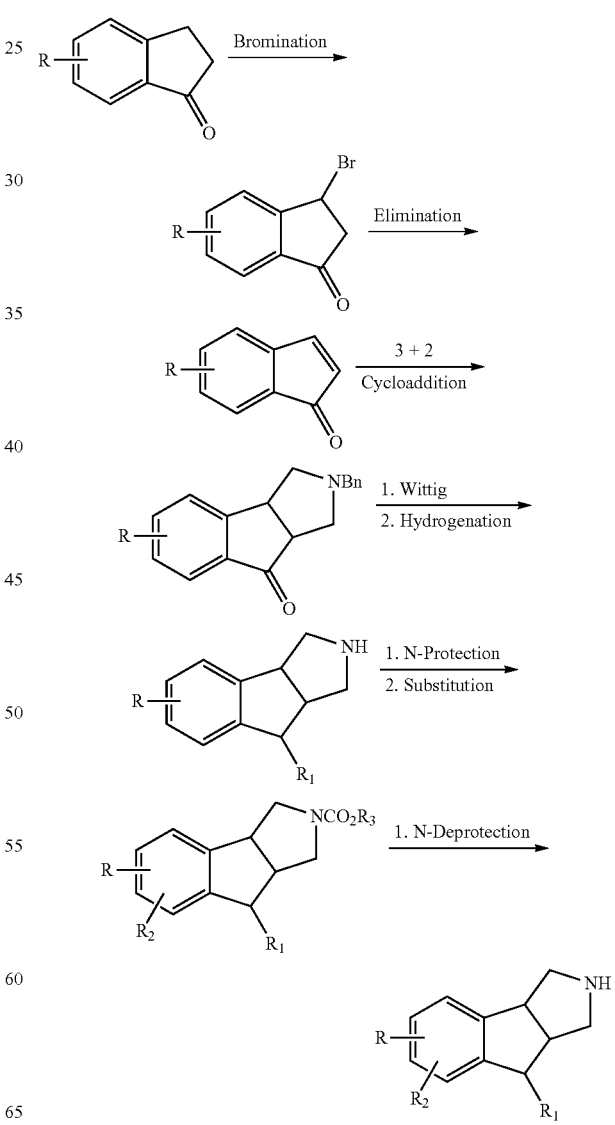

Scheme 1. Synthesis of 8-Substituted-Indeno-pyrroles via a 3 + 2 cycloaddition on substituted indenones.

Scheme 2. Synthesis of Indeno-pyrroles via a Beckmann rearrangement on substituted indenes.

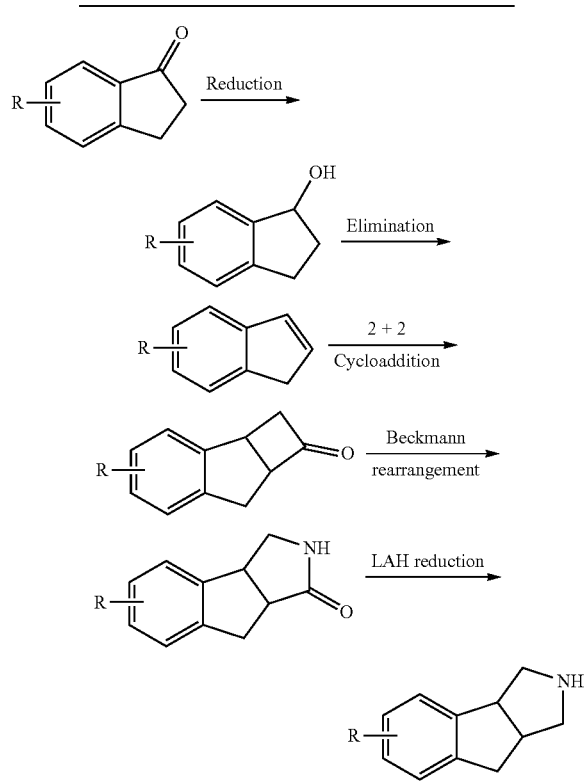

Scheme 3. Synthesis of 8-Substituted-Indeno-pyrroles via a 3 + 2 cycloaddition on substituted cis-substituted-phenyl acrylic acid ethyl esters.

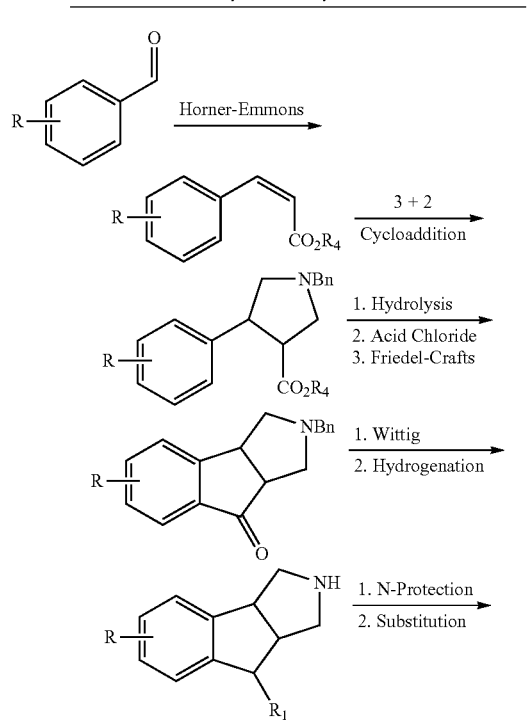

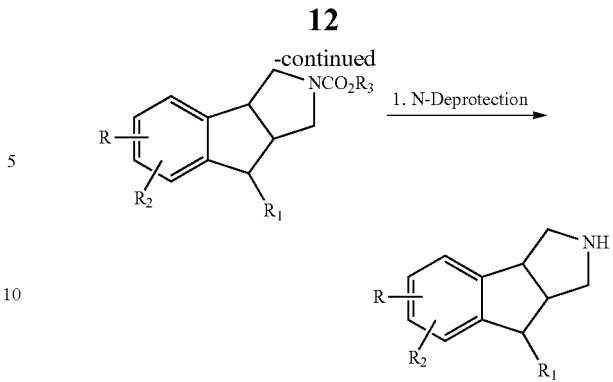

General Analytical Conditions:

HPLC analysis and purification was performed using a Waters 2525 binary gradient pump, Waters 2767 sample manager, waters 2487 UV detector (220 and 254 nM), and Waters Micromass ZQ electrospray mass spec detector. The Micromass ZQ was set for both positive and negative ionization (cone voltage=25 and 50, respectively).

Analytical HPLC analysis was performed as follows:
Waters XTerra MS C18 50×4.6 mm 3.5 μm column
Mobile Phase: 10 mM Ammonium Acetate buffer at pH 5.75 and Acetonitrile
Acetonitrile: 10 to 75% at 3.5 minutes, 75 to 99% at 3.9 minutes, 99% hold to 4.2 minutes, 99 to 10% at 4.5 minutes, re-equilibrate.

Preparative HPLC was performed as follows:
Waters XTerra Prep MS C18 50×19 mm 5 μm column
Mobile Phase: 10 mM Ammonium Acetate buffer at pH 5.75 and Acetonitrile
Acetonitrile: 10 to 99% at 8 minutes, 99% hold to 9 minutes, 99 to 10% at 9.5 minutes, re-equilibrate NMR analysis was performed using a Bruker BioSpin UltraShield NMR (300 MHz)

EXAMPLES

Example 1

5-Methoxy-8-methyl-1,2,3,3a,8,8a-hexahydroindeno [1,2-c]pyrrole

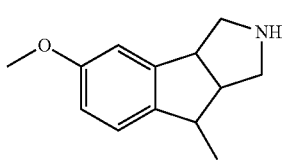

Step A. 3-Bromo-5-methoxy-1-indanone. (Scheme 1)

N-bromosuccinimide (12.1 g, 67.9 mmol) and 2,2'-azobisisobutyronitrile (0.1 g, 0.6 mmol) were added to a solution of 5-methoxy-1-indanone (10.0 g, 61.7 mmol) in carbon tetrachloride (104 mL). The reaction mixture was stirred for 3 hours at 85° C. and then allowed to cool to room temperature. The reaction mixture was filtered through Celite, which was then washed with $CH_2Cl_2$ (100 mL). The filtrate was washed with brine (50 mL), dried over $MgSO_4$, and concentrated to afford the subtitle compound, which was used without further purification. MS calculated for $C_{10}H_9BrO_2$+H: 241, observed: 241.

Step B. 5-Methoxy-inden-1-one.

DBU (9.2 mL, 61.7 mmol) was added to a solution of 5-methoxy-3-bromo-1-indanone (14.8 g, 61.7 mmol) in THF (100 mL) at −10° C. dropwise over 10 minutes. The resulting solution was stirred at −10° C. for 20 minutes, quenched via addition of saturated aqueous NH$_4$Cl (100 mL), and extracted with EtOAc (3×100 mL). The combined organic extracts were washed with brine (100 mL), dried over MgSO$_4$, and concentrated. The crude product was purified by column chromatography (SiO$_2$) using a 0-35% ethyl acetate-hexanes gradient to afford 5.4 g (55%—two steps) of the subtitle compound. $^1$H NMR (CDCl$_3$ 300 MHz) δ 7.42 (d, 1H), 7.38 (d, 1H), 6.62 (s, 1H), 6.60 (d, 1H), 5.89 (d, 1H), 3.85 (s, 3H) ppm. MS calculated for C$_{10}$H$_8$O$_2$+H: 161, observed: 161.

Step C. 2-Benzyl-5-methoxy-2,3,3a,8a-tetrahydro-1H-2-aza-cyclopenta[a]inden-8-one.

N-(Methoxymethyl)-N-(trimethylsilylmethyl)benzylamine (17.3 mL, 67.6 mmol) and TFA (3.4 mL) were added to a solution of 5-methoxy-inden-1-one (5.4 g, 33.8 mmol) in CH$_2$Cl$_2$ (165 mL) at 0° C. The reaction was stirred for 3 hours at room temperature and quenched with saturated aqueous NaHCO$_3$ (165 mL). The organic layer was separated, washed with brine (100 mL), dried over MgSO$_4$, and concentrated to afford the subtitle compound, which was used without further purification. MS calculated for C$_{19}$H$_{19}$NO$_2$+H: 294, observed: 294.

Step D. 2-Benzyl-5-methoxy-8-methylene-1,2,3,3a,8,8a-hexahydroindeno[1,2-c]pyrrole.

Methyltriphenylphosphonium bromide (18.1 g, 50.7 mmol) and potassium tert-butoxide (5.7 g, 50.7 mmol) were added to a solution of 2-benzyl-5-methoxy-2,3,3a,8a-tetrahydro-1H-2-aza-cyclopenta[a]inden-8-one (9.9 g, 33.8 mmol) in anhydrous ether (68 mL). The reaction mixture was stirred for 1 hour at room temperature then filtered through celite. The celite was washed with ether (200 mL), and the filtrate was concentrated. The crude product was purified by column chromatography (SiO$_2$) using a 0-35% ethyl acetate-hexanes gradient to afford 8.1 g (82%—two steps) of the subtitle compound. MS calculated for C$_{20}$H$_{21}$NO+H: 292, observed: 292.

Step E. 5-Methoxy-8-methyl-1,2,3,3a,8,8a-hexahydroindeno[1,2-c]pyrrole.

Ammonium formate (8.1 g) and palladium (10 wt. % on activated carbon, 4.0 g) were added to a solution of 2-benzyl-5-methoxy-8-methylene-1,2,3,3a,8,8a-hexahydroindeno[1,2-c]pyrrole (8.1 g, 27.8 mmol) in MeOH (140 mL). The reaction mixture was stirred for 4 hours at 60° C. and then filtered through celite. The celite was washed with MeOH (200 mL) and the filtrate was concentrated to afford 5.6 g (quantitative yield) of the title compound. An aliquot of the crude product was purified by reverse-phase liquid chromatography to afford the title compound. MS calculated for C$_{13}$H$_{17}$NO+H: 204, observed: 204.

Example 2

5-Hydroxy-8-methyl-1,2,3,3a,8,8a-hexahydroindeno[1,2-c]pyrrole

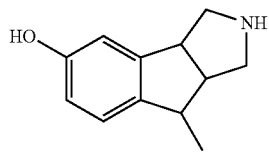

Step A. N-Ethylcarbamate-5-methoxy-8-methyl-1,2,3,3a,8,8a-hexahydroindeno[1,2-c]pyrrole. (Scheme 1)

Hydrogen sodium carbonate (11.7 g, 139 mmol) and ethyl chloroformate (3.2 mL, 33.4 mmol) were added to a solution of 5-methoxy-8-methyl-1,2,3,3a,8,8a-hexahydroindeno[1,2-c]pyrrole (from Example 1, Step E) (5.6 g, 27.8 mmol) in THF/H$_2$O (140 mL, 1/1, v/v), and stirred overnight at room temperature. The reaction mixture was quenched by addition of an aqueous HCl solution (200 mL, 1.0 M) and the product was extracted with EtOAc (3×100 mL). The combined organic extracts were dried over MgSO$_4$ and concentrated. The crude product was purified by column chromatography (SiO$_2$) using a 0-35% ethyl acetate-hexanes gradient to afford 2.7 g (35%) of the subtitle compound. $^1$H NMR (CDCl$_3$ 300 MHz) * 7.07 (d, 1H), 6.78 (m, 2H), 4.09 (m, 2H), 3.79 (m, 5H), 3.63 (m, 1H), 3.52 (m, 1H), 3.32 (m, 1H), 3.07 (m, 1H), 2.95 (m, 1H), 1.26 (m, 6H) ppm. MS calculated for C$_{16}$H$_{21}$NO$_3$+H: 276, observed: 276.

Step B. 5-Hydroxy-8-methyl-1,2,3,3a,8,8a-hexahydroindeno[1,2-c]pyrrole.

N-Ethylcarbamate-5-methoxy-8-methyl-1,2,3,3a,8,8a-hexahydroindeno[1,2-c]pyrrole (12 mg, 0.045 mmol) was dissolved in concentrated HCl (2 mL) and stirred for 20 hours at 120° C. The reaction solution was cooled to room temperature, diluted with H$_2$O (2 mL), and washed with EtOAc (5 mL). The aqueous solution was concentrated on a speed vac to afford the title compound as the hydrochloride salt. MS calculated for C$_{12}$H$_{15}$NO+H: 190, observed: 190.

Example 3

5-Methoxy-6-chloro-8-methyl-1,2,3,3a,8,8a-hexahydroindeno[1,2-c]pyrrole

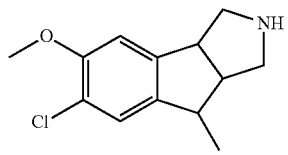

Step A. N-Ethylcarbamate-5-methoxy-6-chloro-8-methyl-1,2,3,3a,8,8a-hexahydroindeno[1,2-c]pyrrole. (Scheme 1)

N-chlorosuccinimide (0.22 g, 1.6 mmol) and acetic acid (8 mL) were added to a solution of N-ethylcarbamate-5-methoxy-8-methyl-1,2,3,3a,8,8a-hexahydroindeno[1,2-c]pyrrole (from Example 2, Step A) (0.45 g, 1.6 mmol) in DCE (8 mL), and stirred for 3 hours at 60° C. The reaction mixture was cooled to room temperature, diluted with CH$_2$Cl$_2$ (50 mL), and washed with H$_2$O (50 mL). The organic extract was dried over MgSO$_4$ and concentrated. The crude product was purified by column chromatography (SiO$_2$) using a 0-35% ethyl acetate-hexanes gradient to afford 250 mg (51%) of the subtitle compound. MS calculated for C$_{16}$H$_{20}$ClNO$_3$+H: 310, observed: 310.

Step B. 5-Methoxy-6-chloro-8-methyl-1,2,3,3a,8,8a-hexahydroindeno[1,2-c]pyrrole.

Barium hydroxide octahydrate (0.63 g, 2.0 mmol) was added to a solution of N-ethylcarbamate-5-methoxy-6-chloro-8-methyl-1,2,3,3a,8,8a-hexahydroindeno[1,2-c]pyrrole (61 mg, 0.2 mmol) in MeOH (4 mL), and stirred for 24 hours at reflux. The reaction mixture was cooled to room temperature and neutralized to pH=7 with aqueous HCl (50 mL, 1 M). The product was extracted with CH$_2$Cl$_2$, dried over MgSO$_4$, and concentrated. The crude product was purified by reverse-phase liquid chromatography to afford the title compound. MS calculated for $C_{13}H_{16}ClNO+H$: 238, observed: 238.

Example 4

5-Hydroxy-6-chloro-8-methyl-1,2,3,3a,8,8a-hexahydroindeno[1,2-c]pyrrole

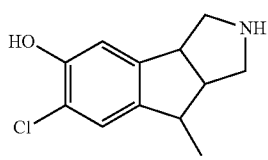

A solution of N-ethylcarbamate-5-methoxy-6-chloro-8-methyl-1,2,3,3a,8,8a-hexahydroindeno[1,2-c]pyrrole (from Example 3, Step A) (61 mg, 0.2 mmol) in concentrated HCl was stirred overnight at 120° C. The reaction solution was cooled to room temperature and concentrated on a speed vac. The crude product was purified by reverse-phase liquid chromatography to afford the title compound. $^1$H NMR ($d_6$-DMSO 300 MHz) * 7.04 (s, 1H), 6.73 (s, 1H), 3.52 (m, 1H), 3.22 (m, 2H), 2.83 (m, 3H), 2.41 (m, 1H), 1.18 (d, 3H) ppm. MS calculated for $C_{12}H_{14}ClNO+H$: 224, observed: 224.

Example 5

6-Chloro-8-methyl-1,2,3,3a,8,8a-hexahydroindeno[1,2-c]pyrrole

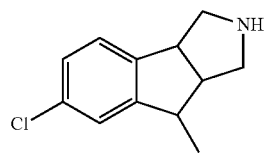

Step A. N-Ethylcarbamate-5-hydroxy-6-chloro-8-methyl-1,2,3,3a,8,8a-hexahydroindeno[1,2-c]pyrrole. (Scheme 1)

BBr$_3$ (3.7 mL, 1.0 M in CH$_2$Cl$_2$) was added to a solution of N-ethylcarbamate-5-methoxy-6-chloro-8-methyl-1,2,3,3a,8,8a-hexahydroindeno[1,2-c]pyrrole (from Example 3, Step A) (0.49 g, 1.6 mmol) in CH$_2$Cl$_2$ (32 mL), and stirred overnight at room temperature. The excess BBr$_3$ was quenched with the dropwise addition of H$_2$O (10 mL), and washed with saturated aqueous NaHCO$_3$ (50 mL) and brine (50 mL). The organic extract was dried over MgSO$_4$ and concentrated to afford the subtitle compound, which was used without further purification. MS calculated for $C_{15}H_{18}ClNO_3+H$: 296, observed: 296.

Step B. N-Ethylcarbamate-5-hydroxy-6-chloro-8-methyl-1,2,3,3a,8,8a-hexahydroindeno[1,2-c]pyrrole, O-trifluoromethanesulfonate.

Pyridine (0.23 mL, 2.85 mmol) and trifluoromethanesulfonic anhydride (0.32 mL, 1.90 mmol) were added to a solution of N-ethylcarbamate-5-hydroxy-6-chloro-8-methyl-1,2,3,3a,8,8a-hexahydroindeno[1,2-c]pyrrole (0.28 g, 0.95 mmol) in CH$_2$Cl$_2$ (10 mL), and stirred for 1.5 hours at room temperature. The reaction was diluted with CH$_2$Cl$_2$ (10 mL), washed with H$_2$O (10 mL), aqueous HCl (1.0 M, 10 mL), saturated aqueous NaHCO$_3$ (10 mL), and brine (10 mL). The organic extract was dried over MgSO$_4$ and concentrated to afford the subtitle compound, which was used without further purification. MS calculated for $C_{16}H_{17}F_3ClNO_5S+H$: 428, observed: 428.

Step C. N-Ethylcarbamate-6-chloro-8-methyl-1,2,3,3a,8,8a-hexahydroindeno[1,2-c]pyrrole.

To a mixture of N-ethylcarbamate-5-hydroxy-6-chloro-8-methyl-1,2,3,3a,8,8a-hexahydroindeno[1,2-c]pyrrole, o-trifluoromethanesulfonate (60 mg, 0.14 mmol), palladium(II) acetate (6 mg, 0.028 mmol) and 1,3-bis(diphenylphosphino)propane (12 mg, 0.035 mmol) in MeOH (0.5 mL) and DMSO (0.5 mL) was added Et$_3$N (0.2 mL, 1.4 mmol). The resulting mixture was stirred for 2 hours at 80° C. then cooled to room temperature. The reaction mixture was diluted with EtOAc (5 mL) and then washed with H$_2$O (2 mL). The organic extract was dried over MgSO$_4$ and concentrated to afford 15 mg (35% yield) of the subtitle compound, which was used without further purification. MS calculated for $C_{15}H_{18}ClNO_2+H$: 280, observed: 280.

Step D. 6-Chloro-8-methyl-1,2,3,3a,8,8a-hexahydroindeno[1,2-c]pyrrole.

The title compound was prepared by the method of Example 4 using N-ethylcarbamate-6-chloro-8-methyl-1,2,3,3a,8,8a-hexahydroindeno[1,2-c]pyrrole. The crude product was purified by reverse-phase liquid chromatography to afford the title compound. MS calculated for $C_{12}H_{14}ClN+H$: 208, observed: 208.

Example 6

5-(4-Fluorobenzyloxy)-6-chloro-8-methyl-1,2,3,3a,8,8a-hexahydroindeno[1,2-c]pyrrole

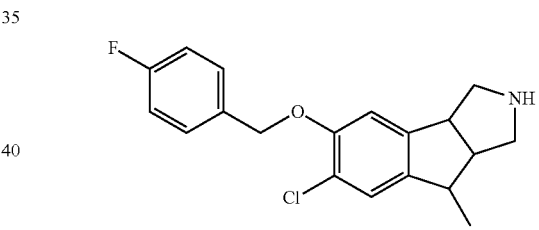

Step A. N-Ethylcarbamate-5-(4-fluorobenzyloxy)-6-chloro-8-methyl-1,2,3,3a,8,8a-hexahydroindeno[1,2-c]pyrrole. (Scheme 1)

4-Fluorobenzyl bromide (23 µL, 0.19 mmol) and potassium carbonate (100 mg, 0.78 mmol) were added to a solution of N-ethylcarbamate-5-hydroxy-6-chloro-8-methyl-1,2,3,3a,8,8a-hexahydroindeno[1,2-c]pyrrole (from Example 5, Step A) (46 mg, 0.16 mmol) in acetonitrile (3 mL), and stirred overnight at 80° C. The reaction was cooled to room temperature, concentrated by rotary evaporation and taken up in H$_2$O (5 mL). The product was extracted with EtOAc (3×10 mL). The combined organic extracts were dried over MgSO$_4$ and concentrated to afford the subtitle compound, which was used without further purification. MS calculated for $C_{22}H_{23}ClFNO_3+H$: 404, observed: 404.

Step B. 5-(4-Fluorobenzyloxy)-6-chloro-8-methyl-1,2,3,3a,8,8a-hexahydroindeno[1,2-c]pyrrole.

The title compound was prepared by the method of Example 3, Step B utilizing N-Ethylcarbamate-5-(4-fluorobenzyloxy)-6-chloro-8-methyl-1,2,3,3a,8,8a-hexahydroindeno[1,2-c]pyrrole. The crude product was purified by reverse-phase liquid chromatography to afford the title compound. $^1$H NMR ($d_6$-DMSO 300 MHz) * 7.51 (m, 2H), 7.23

(m, 3H), 7.09 (s, 1H), 5.18 (m, 2H), 3.63 (m, 1H), 3.27 (m, 2H), 2.7-3.0 (m, 3H), 2.45 (m, 1H), 1.18 (d, 3H) ppm. MS calculated for $C_{19}H_{19}ClFNO+H$: 332, observed: 332.

Example 7

5-Benzyloxy-6-chloro-8-methyl-1,2,3,3a,8,8a-hexahydroindeno[1,2-c]pyrrole

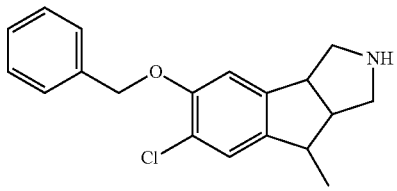 [SMILES: CC1c2cc(Cl)c(OCc3ccccc3)cc2C2CNCC12]

Step A. N-Ethylcarbamate-5-benzyloxy-6-chloro-8-methyl-1,2,3,3a,8,8a-hexahydroindeno[1,2-c]pyrrole. (Scheme 1)

The subtitle compound was prepared by the method of Example 6, Step A utilizing N-ethylcarbamate-5-hydroxy-6-chloro-8-methyl-1,2,3,3a,8,8a-hexahydroindeno[1,2-c]pyrrole (from Example 5, Step A) and benzyl bromide. The crude product was obtained without further purification. MS calculated for $C_{22}H_{24}ClNO_3+H$: 386, observed: 386.

Step B. 5-Benzyloxy-6-chloro-8-methyl-1,2,3,3a,8,8a-hexahydroindeno[1,2-c]pyrrole.

The title compound was prepared by the method of Example 3, Step B utilizing N-ethylcarbamate-5-benzyloxy-6-chloro-8-methyl-1,2,3,3a,8,8a-hexahydro-indeno[1,2-c]pyrrole. The crude product was purified by reverse-phase liquid chromatography to afford the title compound. $^1H$ NMR ($d_6$-DMSO 300 MHz) * 7.28-7.60 (m, 5H), 7.19 (s, 1H), 7.10 (s, 1H), 5.18 (m, 2H), 3.63 (m, 1H), 3.27 (m, 2H), 2.7-3.0 (m, 3H), 2.45 (m, 1H), 1.18 (d, 3H) ppm. MS calculated for $C_{19}H_{20}ClNO+H$: 314, observed: 314.

Example 8

5-(2-Fluorobenzyloxy)-6-chloro-8-methyl-1,2,3,3a,8,8a-hexahydroindeno[1,2-c]pyrrole

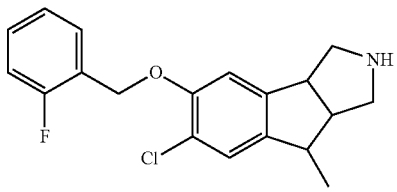 [SMILES: CC1c2cc(Cl)c(OCc3ccccc3F)cc2C2CNCC12]

Step A. N-Ethylcarbamate-5-(2-fluorobenzyloxy)-6-chloro-8-methyl-1,2,3,3a,8,8a-hexahydroindeno[1,2-c]pyrrole. (Scheme 1)

The subtitle compound was prepared by the method of Example 6, Step A utilizing N-ethylcarbamate-5-hydroxy-6-chloro-8-methyl-1,2,3,3a,8,8a-hexahydroindeno[1,2-c]pyrrole (from Example 5, Step A) and 2-fluorobenzyl bromide. The crude product was obtained without further purification. MS calculated for $C_{22}H_{23}ClFNO_3+H$: 404, observed: 404.

Step B. 5-(2-Fluorobenzyloxy)-6-chloro-8-methyl-1,2,3,3a,8,8a-hexahydroindeno[1,2-c]pyrrole.

The title compound was prepared by the method of Example 3, Step B utilizing N-ethylcarbamate-5-(2-fluorobenzyloxy)-6-chloro-8-methyl-1,2,3,3a,8,8a-hexahydroindeno[1,2-c]pyrrole. The crude product was purified by reverse-phase liquid chromatography to afford the title compound. $^1H$ NMR ($d_6$-DMSO 300 MHz) * 7.58 (m, 1H), 7.44 (m, 1H), 7.25 (m, 2H), 7.19 (s, 1H), 7.09 (s, 1H), 5.20 (m, 2H), 3.63 (m, 1H), 3.27 (m, 2H), 2.7-3.0 (m, 3H), 2.45 (m, 1H), 1.22 (d, 3H) ppm. MS calculated for $C_{19}H_{19}ClFNO+H$: 332, observed: 332.

Example 9

5-(3-Fluorobenzyloxy)-6-chloro-8-methyl-1,2,3,3a,8,8a-hexahydroindeno[1,2-c]pyrrole

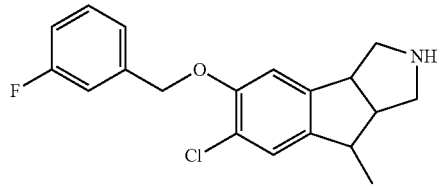 [SMILES: CC1c2cc(Cl)c(OCc3cccc(F)c3)cc2C2CNCC12]

Step A. N-Ethylcarbamate-5-(3-Fluorobenzyloxy)-6-chloro-8-methyl-1,2,3,3a,8,8a-hexahydroindeno[1,2-c]pyrrole. (Scheme 1)

The subtitle compound was prepared by the method of Example 6, Step A utilizing N-ethylcarbamate-5-hydroxy-6-chloro-8-methyl-1,2,3,3a,8,8a-hexahydroindeno[1,2-c]pyrrole (from Example 5 Step A) and 3-fluorobenzyl bromide. The crude product was obtained without further purification. MS calculated for $C_{22}H_{23}ClFNO_3+H$: 404, observed: 404.

Step B. 5-(3-Fluorobenzyloxy)-6-chloro-8-methyl-1,2,3,3a,8,8a-hexahydroindeno[1,2-c]pyrrole.

The title compound was prepared by the method of Example 3, Step B utilizing N-ethylcarbamate-5-(3-fluorobenzyloxy)-6-chloro-8-methyl-1,2,3,3a,8,8a-hexahydroindeno[1,2-c]pyrrole. The crude product was purified by reverse-phase liquid chromatography to afford the title compound. $^1H$ NMR ($d_6$-DMSO 300 MHz) * 7.38 (m, 1H), 7.23 (m, 2H), 7.14 (m, 2H), 7.02 (s, 1H), 5.16 (m, 2H), 3.58 (m, 1H), 3.24 (m, 2H), 2.7-3.0 (m, 3H), 2.45 (m, 1H), 1.14 (d, 3H) ppm. MS calculated for $C_{19}H_{19}ClFNO+H$: 332, observed: 332.

Example 10

1,2,3,3a,8,8a-Hexahydroindeno[1,2-c]pyrrole

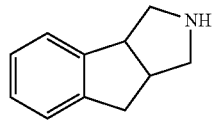 [SMILES: c1ccc2c(c1)CC1CNCC21]

Step A. 2,2a,7,7a-Tetrahydro-cyclobuta[a]inden-1-one. (Scheme 2)

To a suspension of indene (1.2 mL, 10.0 mmol) and activated zinc (1.6 g, 25.0 mmol) in ether (100 mL) was added a solution of trichloroacetyl chloride (3.4 mL, 30.0 mmol) in ether (40 mL). The resulting mixture was stirred for 4 hours at reflux. The reaction was cooled to room temperature, filtered through celite, and the celite washed with ether (2×100 mL). The organic filtrate was washed with H$_2$O (100 mL), dried over MgSO$_4$, and concentrated.

The organic residue was dissolved in MeOH (100 mL). To this solution was added slowly zinc (5.0 g) and NH$_4$Cl (4.0 g). The reaction mixture was stirred overnight at reflux. The reaction mixture was cooled to room temperature, filtered through celite, the celite washed with MeOH (200 mL), and concentrated. The crude product was purified by column chromatography (SiO$_2$) using a 0-35% ethyl acetate-hexanes gradient to afford 1.4 g (89%—two steps) of the subtitle compound. $^1$H NMR (CDCl$_3$ 300 MHz) * 7.24 (m, 4H), 4.06 (m, 2H), 3.63 (m, 1H), 3.29 (d, 1H), 3.10 (m, 1H), 2.88 (d, 1H) ppm.

Step B. 2,2a,7,7a-Tetrahydro-cyclobuta[a]inden-1-one oxime.

Sodium acetate (1.45 g, 17.7 mmol) and hydroxylamine hydrochloride (0.68 g, 9.75 mmol) were added to a solution of 2,2a,7,7a-tetrahydro-cyclobuta[a]inden-1-one (1.4 g, 8.86 mmol) in MeOH (18 mL), and stirred overnight at room temperature. The reaction solution was concentrated via rotary evaporation. The residue was dissolved in CH$_2$Cl$_2$ (100 mL), washed with H$_2$O (50 mL), dried over MgSO$_4$, and concentrated to give the subtitle compound, which was used without further purification. MS calculated for C$_{11}$H$_{11}$NO+H: 174, observed: 174.

Step C. 3,3a,8,8a-Tetrahydro-2H-2-aza-cyclopenta[a]inden-1-one. Thionyl chloride (1.9 mL, 26.4 mmol) was added to a solution of 2,2a,7,7a-tetrahydro-cyclobuta[a]inden-1-one oxime (1.5 g, 8.8 mmol) in 1,4-dioxane (44 mL), and stirred overnight at room temperature. The reaction was quenched with saturated aqueous NaHCO$_3$ (100 mL), and extracted with EtOAc (3×50 mL). The organic extracts were washed with brine, dried over MgSO$_4$, and concentrated to give the subtitle compound and its regioisomer, which were used without further purification. MS calculated for C$_{11}$H$_{11}$NO+H: 174, observed: 174.

Step D. 1,2,3,3a,8,8a-Hexahydroindeno[1,2-c]pyrrole.

A solution of 3,3a,8,8a-tetrahydro-2H-2-aza-cyclopenta[a]inden-1-one (1.5 g, 8.8 mmol) in THF (44 mL) was cannulated to a solution of LAH in THF (26.4 mL, 1.0 M solution in THF). The resulting solution was stirred for 4 hours at 70° C., then overnight at room temperature. The reaction was quenched via the stepwise addition of H$_2$O (1 mL), aqueous NaOH (1 mL, 2.0 M solution), and H$_2$O (3 mL). The resulting mixture was filtered through celite, the celite washed with warm MeOH (200 mL), and the filtrate concentrated to give the subtitle compound and its regioisomer, which were used without further purification. MS calculated for C$_{11}$H$_{13}$N+H: 160, observed: 160.

Step E. N-tert-Butylcarbamate-1,2,3,3a,8,8a-hexahydroindeno[1,2-c]pyrrole.

Di-tert-butyl dicarbonate (2.0 g, 9.4 mmol) and sodium hydrogen carbonate (4.0 g, 47 mmol) were added to a solution of 1,2,3,3a,8,8a-hexahydroindeno[1,2-c]pyrrole (1.5 g, 9.4 mmol) in H$_2$O/THF (46 mL, 1/1, v/v), and stirred overnight at room temperature. The reaction mixture was diluted with H$_2$O (50 mL), and extracted with EtOAc (3×100 mL). The combined organic extracts were dried over MgSO$_4$ and concentrated. The crude products (mixture of regioisomers) were purified and separated by column chromatography (SiO$_2$) using a 0-35% ethyl acetate-hexanes gradient to afford 110 mg (5% yield—5 steps) of the subtitle compound. MS calculated for C$_{16}$H$_{21}$NO$_2$+H: 260, observed: 260.

Step F. 1,2,3,3a,8,8a-Hexahydroindeno[1,2-c]pyrrole.

N-tert-Butylcarbamate-1,2,3,3a,8,8a-hexahydroindeno[1,2-c]pyrrole (110 mg, 0.42 mmol) was dissolved in a HCl solution (5 mL, 4.0 M solution in 1,4-dioxane) and stirred for 2 hours at room temperature. The reaction was concentrated by rotary evaporation. The crude product was purified by reverse-phase liquid chromatography to afford the title compound. $^1$H NMR (d$_6$-DMSO 300 MHz) * 7.16 (m, 4H), 3.71 (m, 1H), 3.25 (m, 1H), 3.0-3.18 (m, 2H), 2.79-3.00 (m, 2H), 2.72 (m, 1H), 2.45 (m, 1H) ppm. MS calculated for C$_{11}$H$_{13}$N+H: 160, observed: 160.

Example 11

6-Chloro-1,2,3,3a,8,8a-hexahydroindeno[1,2-c]pyrrole

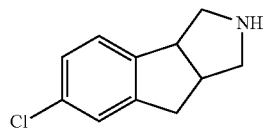 [SMILES: Clc1ccc2c(c1)CC1CNCC21]

Step A. 6-Chloro-1H-indene. (Scheme 2)

Sodium borohydride (2.3 g, 60.2 mmol) was added to a solution of 5-chloro-1-indanone (10.0 g, 60.2 mmol) in MeOH (300 mL), and stirred for 3 hours at room temperature. The reaction was quenched with H$_2$O (100 mL), and extracted with CH$_2$Cl$_2$ (3×100 mL). The combined extracts were dried over MgSO$_4$ and concentrated.

The organic residue was dissolved in toluene (300 mL) and treated with p-toluenesulfonic acid monohydrate (1.2 g, 6.02 mmol), which was stirred for 1 hour at 90° C. The reaction was cooled to room temperature, washed with brine (150 mL), dried over MgSO4, and concentrated to give 6.9 g (76%—two steps) of the subtitle compound, which was used without further purification.

Step B. 5-Chloro-2,2a,7,7a-tetrahydro-cyclobuta[a]inden-1-one.

The subtitle compound was prepared by the method of Example 10, Step A utilizing 6-chloro-1H-indene (3.4 g, 22.6 mmol). The crude product was obtained without further purification.

Step C. 5-Chloro-2,2a,7,7a-tetrahydro-cyclobuta[a]inden-1-one oxime.

The subtitle compound was prepared by the method of Example 10, Step B utilizing 5-chloro-2,2a,7,7a-tetrahydrocyclobuta[a]inden-1-one (2.0 g, 10.4 mmol). The crude product was obtained without further purification. MS calculated for C$_{11}$H$_{10}$ClNO+H: 208, observed: 208.

Step D. 6-Chloro-3,3a,8,8a-tetrahydro-2H-2-aza-cyclopenta[a]inden-1-one.

The subtitle compound was prepared by the method of Example 10, Step C utilizing 5-chloro-2,2a,7,7a-tetrahydrocyclobuta[a]inden-1-one (2.0 g, 10.4 mmol) The crude product was obtained without further purification. MS calculated for C$_{11}$H$_{10}$ClNO+H: 208, observed: 208.

Step E. 6-Chloro-1,2,3,3a,8,8a-hexahydroindeno[1,2-c]pyrrole.

The subtitle compound was prepared by the method of Example 10, Step D utilizing 6-chloro-3,3a,8,8a-tetrahydro-2H-2-aza-cyclopenta[a]inden-1-one (2.0 g, 10.4 mmol). The crude product was obtained without further purification. MS calculated for C$_{11}$H$_{12}$ClN+H: 194, observed: 194.

Step F. N-tert-Butylcarbamate-6-chloro-1,2,3,3a,8,8a-hexahydroindeno[1,2-c]pyrrole.

The subtitle compound was prepared by the method of Example 10, Step E utilizing 6-chloro-1,2,3,3a,8,8a-hexahydroindeno[1,2-c]pyrrole (2.0 g, 10.4 mmol). The crude product was obtained without further purification. MS calculated for $C_{16}H_{20}ClNO_2$+H: 294, observed: 294.

Step G. 6-Chloro-1,2,3,3a,8,8a-hexahydroindeno[1,2-c]pyrrole.

The title compound was prepared by the method of Example 10, Step F utilizing N-tert-butylcarbamate-6-chloro-1,2,3,3a,8,8a-hexahydroindeno[1,2-c]pyrrole. The crude product was purified by reverse-phase liquid chromatography to afford the title compound. $^1$H NMR (d$_6$-DMSO 300 MHz) δ 7.25 (m, 3H), 3.71 (m, 1H), 3.19 (m, 2H), 3.05 (m, 2H), 2.88 (m, 1H), 2.77 (m, 1H), 2.45 (m, 1H) ppm. MS calculated for $C_{11}H_{13}ClN$+H: 194, observed: 194.

Example 12

6-(2,6-Difluorophenyl)-1,2,3,3a,8,8a-hexahydroindeno[1,2-c]pyrrole

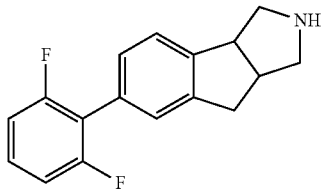 [SMILES: Fc1cccc(F)c1-c1ccc2c(c1)CC1CNCC21]

Step A. N-tert-Butylcarbamate-6-(2,6-difluorophenyl)-1,2,3,3a,8,8a-hexahydroindeno[1,2-c]pyrrole. (Scheme 2)

Triphenylphosphine (2 mg), palladium(II) acetate (1 mg), 2,6-difluorophenyl boronic acid (20 mg, 0.12 mmol), and aqueous sodium carbonate (0.15 mL, 0.3 mmol) were added to a solution of (N-tert-butylcarbamate-6-chloro-1,2,3,3a,8,8a-hexahydroindeno[1,2-c]pyrrole (from Example 11, Step F) (30 mg, 0.1 mmol) in acetonitrile (1 mL), and stirred for 24 h at 80° C. The reaction mixture was concentrated, diluted with EtOAc (5 mL) and washed with H$_2$O (5 mL). The organic extract was dried over MgSO$_4$ and concentrated to give the subtitle compound, which was used without further purification. MS calculated for $C_{22}H_{23}F_2NO_2$+H: 372, observed: 372.

Step B. 6-(2,6-Difluorophenyl)-1,2,3,3a,8,8a-hexahydroindeno[1,2-c]pyrrole.

The title compound was prepared by the method of Example 10, Step F. The crude product was purified by reverse-phase liquid chromatography to afford the title compound. MS calculated for $C_{17}H_{15}F_2N$+H: 272, observed: 272.

Example 13

5-Methyl-8-methyl-1,2,3,3a,8,8a-hexahydroindeno[1,2-c]pyrrole

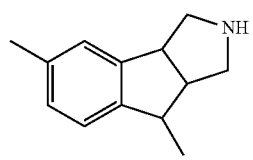

Step A. 3-m-Tolyl-acrylic acid ethyl ester. (Scheme 3) KHMDS (4.0 g, 20.0 mmol) was added to a solution of ethyl[bis(2,2,2-trifluoro-ethoxy)phosphinyl]acetate (4.7 mL, 20.0 mmol) and 18-crown-6 (10.6 g, 40.0 mmol) in THF (200 mL) at −78° C., and stirred for 30 minutes. m-Tolualdehyde (2.1 mL, 18 mmol) was added and the reaction mixture was stirred for 3 hours from −78° C. to room temperature. The reaction was quenched with aqueous hydrochloric acid (1M solution, 100 mL), and the product was extracted with EtOAc (3×100 mL). The organic extracts were washed with brine (100 mL), dried over MgSO$_4$, and concentrated to afford the subtitle compound, which was used without further purification. MS calculated for $C_{12}H_{14}O_2$+H: 191, observed: 191.

Step B. 1-Benzyl-4-m-tolyl-pyrrolidine-3-carboxylic acid ethyl ester.

The subtitle compound was prepared by the method of Example 1, Step C utilizing 3-m-tolyl-acrylic acid ethyl ester (18.0 mmol). The crude product was purified by column chromatography (SiO$_2$) using a 10-50% ethyl acetate-hexanes gradient to afford 4.7 g (81%—two steps) of the subtitle compound. MS calculated for $C_{21}H_{25}NO_2$+H: 324, observed: 324.

Step C. 1-Benzyl-4-m-tolyl-pyrrolidine-3-carboxylic acid.

1-Benzyl-4-m-tolyl-pyrrolidine-3-carboxylic acid ethyl ester (4.6 g, 14.5 mmol) was suspended in aqueous HCl (73 mL, 18.0 M), and stirred overnight at 80° C. The reaction mixture was concentrated via rotary evaporation and placed on the vacuum line. MS calculated for $C_{19}H_{21}NO_2$+H: 296, observed: 296.

Step D. 2-Benzyl-5-methyl-2,3,3a,8a-tetrahydro-1H-2-aza-cyclopenta[a]inden-8-one.

DMF (16 drops) and oxalyl chloride (4.1 mL, 43.5 mmol) were added to a solution of 1-benzyl-4-m-tolyl-pyrrolidine-3-carboxylic acid (4.3 g, 14.5 mmol) in CH$_2$Cl$_2$ (29 mL) at 0° C. The reaction mixture was stirred overnight at room temperature, then concentrated via rotary evaporation, and placed on the vacuum line without any purification.

A solution of the acid chloride intermediate in CH$_2$Cl$_2$ (29 mL) was added slowly to a solution of AlCl$_3$ (4.9 g, 43.5 mmol) in CH$_2$Cl$_2$ (29 mL) at 0° C. The reaction mixture was stirred for 3 hours from 0° C. to room temperature, then quenched via the slow addition of a saturated solution of sodium bicarbonate (290 mL). The product was extracted with CH$_2$Cl$_2$ (3×100 mL). The organic extracts were washed with brine, dried over MgSO$_4$, and concentrated. The crude product was purified by column chromatography (SiO$_2$) using a 10-50% ethyl acetate-hexanes gradient to afford 0.91 g (23%—two steps) of the subtitle compound and 0.12 g (3%—two steps) of the regioisomeric 2-benzyl-7-methyl-2,3,3a,8a-tetrahydro-1H-2-aza-cyclopenta[a]inden-8-one. MS calculated for $C_{19}H_{19}NO$+H: 278, observed: 278.

Step E. 2-Benzyl-5-methyl-8-methylene-1,2,3,3a,8,8a-hexahydro-2-aza-cyclopenta[a]indene.

The subtitle compound was prepared by the method of Example 1, Step D utilizing 2-benzyl-5-methyl-2,3,3a,8a-tetrahydro-1H-2-aza-cyclopenta[a]inden-8-one (3.2 mmol). The crude product was purified by silica plug eluting with ethyl acetate-hexanes (3/1, v/v) to afford 0.88 g (98%) of the subtitled compound. MS calculated for $C_{20}H_{21}N$+H: 276, observed: 276.

Step F. 5-Methyl-8-methyl-1,2,3,3a,8,8a-hexahydroindeno[1,2-c]pyrrole.

The title compound was prepared by the method of Example 1, Step E utilizing 2-benzyl-5-methyl-8-methylene-1,2,3,3a,8,8a-hexahydro-2-aza-cyclopenta[a]indene (3.2 mmol). An aliquot of the crude product was purified by reverse-phase liquid chromatography to afford the title compound. $^1$H NMR (d$_6$-DMSO 300 MHz) * 6.98 (m, 3H), 3.55

(m, 1H), 3.25 (m, 2H), 2.85 (m, 3H), 2.45 (m, 1H), 2.24 (s, 3H), 1.22 (d, 3H) ppm. MS calculated for $C_{13}H_{17}N+H$: 188, observed: 188.

Example 14

4-Methyl-8-methyl-1,2,3,3a,8,8a-hexahydroindeno [1,2-c]pyrrole

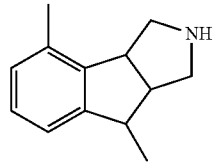

Step A. 3-o-Tolyl-acrylic acid ethyl ester. (Scheme 3)

The subtitle compound was prepared by the method of Example 13, Step A utilizing o-tolualdehyde (9.0 mmol). The crude product was obtained without further purification. MS calculated for $C_{12}H_{14}O_2+H$: 191, observed: 191.

Step B. 1-Benzyl-4-o-tolyl-pyrrolidine-3-carboxylic acid ethyl ester.

The subtitle compound was prepared by the method of Example 1, Step C utilizing 3-o-tolyl-acrylic acid ethyl ester (9.0 mmol). The crude product was purified by column chromatography ($SiO_2$) using a 10-50% ethyl acetate-hexanes gradient to afford 2.3 g (79%—two steps) of the subtitle compound. MS calculated for $C_{21}H_{25}NO_2+H$: 324, observed: 324.

Step C. 1-Benzyl-4-o-tolyl-pyrrolidine-3-carboxylic acid.

The subtitle compound was prepared by the method of Example 13, Step C utilizing 1-benzyl-4-o-tolyl-pyrrolidine-3-carboxylic acid ethyl ester (7.1 mmol). The crude product was obtained without further purification. MS calculated for $C_{19}H_{21}NO_2+H$: 296, observed: 296.

Step D. 2-Benzyl-4-methyl-2,3,3a,8a-tetrahydro-1H-2-aza-cyclopenta[a]inden-8-one.

The subtitle compound was prepared by the method of Example 13, Step D utilizing 1-benzyl-4-o-tolyl-pyrrolidine-3-carboxylic acid (7.1 mmol). The crude product was purified by column chromatography ($SiO_2$) using a 15-60% EtOAc-hexanes gradient to afford 0.73 g (37%—two steps) of the subtitle compound. MS calculated for $C_{19}H_{19}NO+H$: 278, observed: 278.

Step E. 2-Benzyl-4-methyl-8-methylene-1,2,3,3a,8,8a-hexahydro-2-aza-cyclopenta[a]indene.

The subtitle compound was prepared by the method of Example 1, Step D utilizing 2-benzyl-4-methyl-2,3,3a,8a-tetrahydro-1H-2-aza-cyclopenta[a]inden-8-one (2.6 mmol). The crude product was purified by silica plug eluting with EtOAc-hexanes (3/1, v/v) to afford the subtitled compound. MS calculated for $C_{20}H_{21}N+H$: 276, observed: 276.

Step F. 4-Methyl-8-methyl-1,2,3,3a,8,8a-hexahydroindeno[1,2-c]pyrrole.

The title compound was prepared by the method of Example 1, Step E utilizing 2-benzyl-4-methyl-8-methylene-1,2,3,3a,8,8a-hexahydro-2-aza-cyclopenta[a]indene (2.6 mmol). An aliquot of the crude product was purified by reverse-phase liquid chromatography to afford the title compound. $^1H$ NMR ($d_6$-DMSO 300 MHz) * 7.10 (m, 1H), 6.98 (m, 2H), 3.72 (m, 1H), 3.48 (m, 1H), 3.22 (m, 1H), 2.97 (m, 2H), 2.72 (m, 1H), 2.45 (m, 1H), 2.21 (s, 3H), 1.22 (d, 3H) ppm. MS calculated for $C_{13}H_{17}N+H$: 188, observed: 188.

Example 15

6-Methyl-8-methyl-1,2,3,3a,8,8a-hexahydroindeno [1,2-c]pyrrole

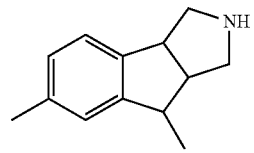

Step A. 3-p-Tolyl-acrylic acid ethyl ester. (Scheme 3)

The subtitle compound was prepared by the method of Example 13, Step A utilizing p-tolualdehyde (4.5 mmol). The crude product was obtained without further purification. MS calculated for $C_{12}H_{14}O_2+H$: 191, observed: 191.

Step B. 1-Benzyl-4-p-tolyl-pyrrolidine-3-carboxylic acid ethyl ester.

The subtitle compound was prepared by the method of Example 1, Step C utilizing 3-p-tolyl-acrylic acid ethyl ester (4.5 mmol). The crude product was purified by column chromatography ($SiO_2$) using a 10-60% EtOAc-hexanes gradient to afford 1.15 g (79%—two steps) of the subtitle compound. MS calculated for $C_{21}H_{25}NO_2+H$: 324, observed: 324.

Step C. 1-Benzyl-4-p-tolyl-pyrrolidine-3-carboxylic acid.

The subtitle compound was prepared by the method of Example 13, Step C utilizing 1-benzyl-4-p-tolyl-pyrrolidine-3-carboxylic acid ethyl ester (3.6 mmol). The crude product was obtained without further purification. MS calculated for $C_{19}H_{21}NO_2+H$: 296, observed: 296.

Step D. 2-Benzyl-6-methyl-2,3,3a,8a-tetrahydro-1H-2-aza-cyclopenta[a]inden-8-one.

The subtitle compound was prepared by the method of Example 13, Step D utilizing 1-benzyl-4-p-tolyl-pyrrolidine-3-carboxylic acid (3.6 mmol). The crude product was purified by column chromatography ($SiO_2$) using a 15-60% EtOAc-hexanes gradient to afford 0.50 g (50%—two steps) of the subtitle compound. MS calculated for $C_{19}H_{19}NO+H$: 278, observed: 278.

Step E. 2-Benzyl-6-methyl-8-methylene-1,2,3,3a,8,8a-hexahydro-2-aza-cyclopenta[a]indene.

The subtitle compound was prepared by the method of Example 1, Step D utilizing 2-benzyl-6-methyl-2,3,3a,8a-tetrahydro-1H-2-aza-cyclopenta[a]inden-8-one (1.8 mmol). The crude product was purified by silica plug eluting with EtOAc-hexanes (3/1, v/v) to afford the subtitle compound. MS calculated for $C_{20}H_{21}N+H$: 276, observed: 276.

Step F. 6-Methyl-8-methyl-1,2,3,3a,8,8a-hexahydroindeno[1,2-c]pyrrole.

The title compound was prepared by the method of Example 1, Step E utilizing 2-benzyl-6-methyl-8-methylene-1,2,3,3a,8,8a-hexahydro-2-aza-cyclopenta[a]indene (1.8 mmol). An aliquot of the crude product was purified by reverse-phase liquid chromatography to afford the title compound. $^1H$ NMR ($d_6$-DMSO 300 MHz) * 7.00 (m, 3H), 3.61

(m, 1H), 3.30 (m, 2H), 2.9 (m, 3H), 2.42 (m, 1H), 2.27 (s, 3H), 1.22 (d, 3H) ppm. MS calculated for $C_{13}H_{17}N+H$: 188, observed: 188.

Example 16

7-Methyl-8-methyl-1,2,3,3a,8,8a-hexahydroindeno[1,2-c]pyrrole

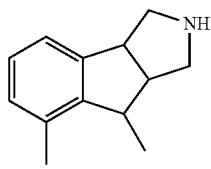

Step A. 2-Benzyl-7-methyl-8-methylene-1,2,3,3a,8,8a-hexahydro-2-aza-cyclopenta[a]indene. (Scheme 3)

The subtitle compound was prepared by the method of Example 1, Step D utilizing 2-benzyl-7-methyl-2,3,3a,8a-tetrahydro-1H-2-aza-cyclopenta[a]inden-8-one (from Example 13, Step D, regioisomer) (0.43 mmol). The crude product was purified by silica plug eluting with EtOAc-hexanes (3/1, v/v) to afford the subtitle compound. MS calculated for $C_{20}H_{21}N+H$: 276, observed: 276.

Step B. 7-Methyl-8-methyl-1,2,3,3a,8,8a-hexahydroindeno[1,2-c]pyrrole.

The title compound was prepared by the method of Example 1, Step E utilizing 2-benzyl-7-methyl-8-methylene-1,2,3,3a,8,8a-hexahydro-2-aza-cyclopenta[a]indene (0.43 mmol). An aliquot of the crude product was purified by reverse-phase liquid chromatography to afford the title compound. $^1$H NMR (d$_6$-DMSO 300 MHz) * 7.05 (m, 3H), 3.62 (m, 1H), 3.39 (m, 2H), 2.99 (m, 3H), 2.77 (m, 1H), 2.28 (s, 3H), 1.27 (d, 3H) ppm. MS calculated for $C_{13}H_{17}N+H$: 188, observed: 188.

Example 17

4-Fluoro-8-methyl-1,2,3,3a,8,8a-hexahydroindeno[1,2-c]pyrrole

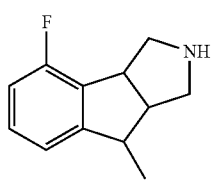

Step A. 3-o-Fluoro-acrylic acid ethyl ester. (Scheme 3)

The subtitle compound was prepared by the method of Example 13, Step A utilizing 2-fluorobenzaldehyde (9.0 mmol). The crude product was obtained without further purification. MS calculated for $C_{11}H_{11}FO_2+H$: 195, observed: 195.

Step B. 1-Benzyl-4-o-fluoro-pyrrolidine-3-carboxylic acid ethyl ester.

The subtitle compound was prepared by the method of Example 1, Step C utilizing 3-o-fluoro-acrylic acid ethyl ester (9.0 mmol). The crude product was purified by column chromatography (SiO$_2$) using a 10-50% EtOAc-hexanes gradient to afford the subtitle compound in quantitative yield. MS calculated for $C_{20}H_{22}FNO_2+H$: 328, observed: 328.

Step C. 1-Benzyl-4-o-fluoro-pyrrolidine-3-carboxylic acid.

The subtitle compound was prepared by the method of Example 13, Step C utilizing 1-benzyl-4-o-fluoro-pyrrolidine-3-carboxylic acid ethyl ester (9.0 mmol). The crude product was obtained without further purification. MS calculated for $C_{18}H_{18}FNO_2+H$: 300, observed: 300.

Step D. 2-Benzyl-4-fluoro-2,3,3a,8a-tetrahydro-1H-2-aza-cyclopenta[a]inden-8-one.

The subtitle compound was prepared by the method of Example 13, Step D utilizing 1-benzyl-4-o-fluoro-pyrrolidine-3-carboxylic acid (9.0 mmol). The crude product was purified by column chromatography (SiO$_2$) using a 0-50% EtOAc-hexanes gradient to afford 0.59 g (23%—four steps) of the subtitle compound. MS calculated for $C_{18}H_{16}FNO+H$: 282, observed: 282.

Step E. 2-Benzyl-4-fluoro-8-methylene-1,2,3,3a,8,8a-hexahydro-2-aza-cyclopenta[a]indene.

The subtitle compound was prepared by the method of Example 1, Step D utilizing 2-benzyl-4-fluoro-2,3,3a,8a-tetrahydro-1H-2-aza-cyclopenta[a]inden-8-one (2.1 mmol). The crude product was purified by silica plug eluting with EtOAc-hexanes (3/1, v/v) to afford the subtitle compound. MS calculated for $C_{29}H_{18}FN+H$: 280, observed: 280.

Step F. 4-Fluoro-8-methyl-1,2,3,3a,8,8a-hexahydroindeno[1,2-c]pyrrole.

The title compound was prepared by the method of Example 1, Step E utilizing 2-benzyl-4-fluoro-8-methylene-1,2,3,3a,8,8a-hexahydro-2-aza-cyclopenta[a]indene (2.1 mmol). An aliquot of the crude product was purified by reverse-phase liquid chromatography to afford the title compound. $^1$H NMR (d$_6$-DMSO 300 MHz) * 7.26 (m, 1H), 6.99 (m, 2H), 3.83 (m, 1H), 3.39 (m, 2H), 2.99 (m, 3H), 2.51 (m, 1H), 1.26 (d, 3H) ppm. MS calculated for $C_{12}H_{14}FN+H$: 192, observed: 192.

Example 18

5-Fluoro-8-methyl-1,2,3,3a,8,8a-hexahydroindeno[1,2-c]pyrrole

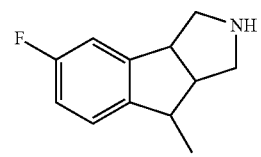

Step A. 3-m-Fluoro-acrylic acid ethyl ester. (Scheme 3)

The subtitle compound was prepared by the method of Example 13, Step A utilizing m-fluorobenzaldehyde (18.0 mmol). The crude product was obtained without further purification. MS calculated for $C_{11}H_{11}FO_2+H$: 195, observed: 195.

Step B. 1-Benzyl-4-m-fluoro-pyrrolidine-3-carboxylic acid ethyl ester.

The subtitle compound was prepared by the method of Example 1, Step C utilizing 3-m-fluoro-acrylic acid ethyl ester (18.0 mmol). The crude product was purified by column chromatography (SiO$_2$) using a 10-50% EtOAc-hexanes gradient to afford the subtitle compound in quantitative yield. MS calculated for $C_{20}H_{22}FNO_2+H$: 328, observed: 328.

Step C. 1-Benzyl-4-m-fluoro-pyrrolidine-3-carboxylic acid.

The subtitle compound was prepared by the method of Example 13, Step C utilizing 1-benzyl-4-m-fluoro-pyrrolidine-3-carboxylic acid ethyl ester (18.0 mmol). The crude product was obtained without further purification. MS calculated for $C_{18}H_{18}FNO_2$+H: 300, observed: 300.

Step D. 2-Benzyl-5-fluoro-2,3,3a,8a-tetrahydro-1H-2-aza-cyclopenta[a]inden-8-one.

The subtitle compound was prepared by the method of Example 13, Step D utilizing 1-benzyl-4-m-fluoro-pyrrolidine-3-carboxylic acid (18.0 mmol). The crude product was purified by column chromatography (SiO$_2$) using a 0-50% EtOAc-hexanes gradient to afford 2.7 g (53%—four steps) of the subtitle compound. MS calculated for $C_{18}H_{16}FNO$+H: 282, observed: 282.

Step E. 2-Benzyl-5-fluoro-8-methylene-1,2,3,3a,8,8a-hexahydro-2-aza-cyclopenta[a]indene.

The subtitle compound was prepared by the method of Example 1, Step D utilizing 2-benzyl-5-fluoro-2,3,3a,8a-tetrahydro-1H-2-aza-cyclopenta[a]inden-8-one (9.6 mmol). The crude product was purified by silica plug eluting with EtOAc-hexanes (3/1, v/v) to afford the subtitle compound. MS calculated for $C_{29}H_{18}FN$+H: 280, observed: 280.

Step F. 5-Fluoro-8-methyl-1,2,3,3a,8,8a-hexahydroindeno[1,2-c]pyrrole.

The title compound was prepared by the method of Example 1, Step E utilizing 2-benzyl-5-fluoro-8-methylene-1,2,3,3a,8,8a-hexahydro-2-aza-cyclopenta[a]indene (9.6 mmol). An aliquot of the crude product was purified by reverse-phase liquid chromatography to afford the title compound. $^1$H NMR (d$_6$-DMSO 300 MHz) * 7.18 (m, 1H), 7.02 (m, 2H), 3.68 (m, 1H), 3.33 (m, 2H), 2.98 (m, 3H), 2.45 (m, 1H), 1.21 (d, 3H) ppm. MS calculated for $C_{12}H_{14}FN$+H: 192, observed: 192.

Example 19

6-Fluoro-8-methyl-1,2,3,3a,8,8a-hexahydroindeno[1,2-c]pyrrole

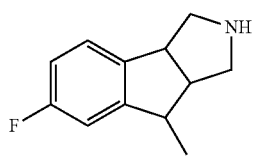

Step A. 3-p-Fluoro-acrylic acid ethyl ester. (Scheme 3)

The subtitle compound was prepared by the method of Example 13, Step A utilizing p-fluorobenzaldehyde (9.0 mmol). The crude product was obtained without further purification. MS calculated for $C_{11}H_{11}FO_2$+H: 195, observed: 195.

Step B. 1-Benzyl-4-p-fluoro-pyrrolidine-3-carboxylic acid ethyl ester.

The subtitle compound was prepared by the method of Example 1, Step C utilizing 3-p-fluoro-acrylic acid ethyl ester (9.0 mmol). The crude product was purified by column chromatography (SiO$_2$) using a 10-50% EtOAc-hexanes gradient to afford the subtitle compound in quantitative yield. MS calculated for $C_{20}H_{22}FNO_2$+H: 328, observed: 328.

Step C. 1-Benzyl-4-p-fluoro-pyrrolidine-3-carboxylic acid.

The subtitle compound was prepared by the method of Example 13, Step C utilizing 1-benzyl-4-p-fluoro-pyrrolidine-3-carboxylic acid ethyl ester (9.0 mmol). The crude product was obtained without further purification. MS calculated for $C_{18}H_{18}FNO_2$+H: 300, observed: 300.

Step D. 2-Benzyl-6-fluoro-2,3,3a,8a-tetrahydro-1H-2-aza-cyclopenta[a]inden-8-one.

The subtitle compound was prepared by the method of Example 13, Step D utilizing 1-benzyl-4-p-fluoro-pyrrolidine-3-carboxylic acid (9.0 mmol). The crude product was purified by column chromatography (SiO$_2$) using a 0-50% EtOAc-hexanes gradient to afford 1.12 g (44%—four steps) of the subtitle compound. MS calculated for $C_{18}H_{16}FNO$+H: 282, observed: 282.

Step E. 2-Benzyl-6-fluoro-8-methylene-1,2,3,3a,8,8a-hexahydro-2-aza-cyclopenta[a]indene.

The subtitle compound was prepared by the method of Example 1, Step D utilizing 2-benzyl-6-fluoro-2,3,3a,8a-tetrahydro-1H-2-aza-cyclopenta[a]inden-8-one (4.0 mmol). The crude product was purified by silica plug eluting with EtOAc-hexanes (3/1, v/v) to afford the subtitle compound. MS calculated for $C_{29}H_{18}FN$+H: 280, observed: 280.

Step F. 6-Fluoro-8-methyl-1,2,3,3a,8,8a-hexahydroindeno[1,2-c]pyrrole.

The title compound was prepared by the method of Example 1, Step E utilizing 2-benzyl-5-fluoro-8-methylene-1,2,3,3a,8,8a-hexahydro-2-aza-cyclopenta[a]indene (4.0 mmol). An aliquot of the crude product was purified by reverse-phase liquid chromatography to afford the title compound. $^1$H NMR (d$_6$-DMSO 300 MHz) * 7.18 (m, 1H), 6.99 (m, 2H), 3.62 (m, 1H), 3.29 (m, 2H), 2.87 (m, 3H), 2.45 (m, 1H), 1.22 (d, 3H) ppm. MS calculated for $C_{12}H_{14}FN$+H: 192, observed: 192.

Example 20

5-Chloro-8-methyl-1,2,3,3a,8,8a-hexahydroindeno[1,2-c]pyrrole

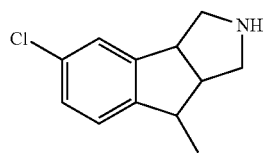

Step A. 3-m-Chloro-acrylic acid ethyl ester. (Scheme 3)

The subtitle compound was prepared by the method of Example 13, Step A utilizing 3-chlorobenzaldehyde (9.0 mmol). The crude product was obtained without further purification. MS calculated for $C_{11}H_{11}ClO_2$+H: 211, observed: 211.

Step B. 1-Benzyl-4-m-chloro-pyrrolidine-3-carboxylic acid ethyl ester.

The subtitle compound was prepared by the method of Example 1, Step C utilizing 3-m-chloro-acrylic acid ethyl ester (9.0 mmol). The crude product was purified by column chromatography (SiO$_2$) using a 10-50% EtOAc-hexanes gradient to afford the subtitle compound in quantitative yield. MS calculated for $C_{20}H_{22}ClNO_2$+H: 344, observed: 344.

Step C. 1-Benzyl-4-m-chloro-pyrrolidine-3-carboxylic acid.

The subtitle compound was prepared by the method of Example 13, Step C utilizing 1-benzyl-4-m-chloro-pyrrolidine-3-carboxylic acid ethyl ester (9.0 mmol). The crude product was obtained without further purification. MS calculated for $C_{18}H_{18}ClNO_2$+H: 316, observed: 316.

Step D. 2-Benzyl-5-chloro-2,3,3a,8a-tetrahydro-1H-2-aza-cyclopenta[a]inden-8-one.

The subtitle compound was prepared by the method of Example 13, Step D utilizing 1-benzyl-4-m-chloro-pyrrolidine-3-carboxylic acid (9.0 mmol). The crude product was purified by column chromatography ($SiO_2$) using a 0-50% EtOAc-hexanes gradient to afford 0.59 g (22%—four steps) of the subtitle compound and 0.20 g (8%—four steps) of the regioisomeric 2-benzyl-7-chloro-2,3,3a,8a-tetrahydro-1H-2-aza-cyclopenta[a]inden-8-one. MS calculated for $C_{18}H_{16}ClNO$+H: 298, observed: 298.

Step E. 2-Benzyl-5-chloro-8-methylene-1,2,3,3a,8,8a-hexahydro-2-aza-cyclopenta[a]indene.

The subtitle compound was prepared by the method of Example 1, Step D utilizing 2-benzyl-5-chloro-2,3,3a,8a-tetrahydro-1H-2-aza-cyclopenta[a]inden-8-one (2.0 mmol). The crude product was purified by silica plug eluting with EtOAc-hexanes (3/1, v/v) to afford the subtitle compound. MS calculated for $C_{19}H_{18}ClN$+H: 296, observed: 296.

Step F. 5-Chloro-8-methylene-1,2,3,3a,8,8a-hexahydro-2-aza-cyclopenta[a]indene.

ACE-Cl (1.08 mL, 9.9 mmol) and $K_2CO_3$ (1.4 g, 9.9 mmol) were added to a solution of 2-benzyl-5-chloro-8-methylene-1,2,3,3a,8,8a-hexahydro-2-aza-cyclopenta[a]indene (2.0 mmol) in DCE (10 mL) at 0° C. The reaction mixture was stirred for 30 minutes at 0° C., then overnight at 60° C. The reaction mixture was filtered through celite, the celite was washed with $CH_2Cl_2$, and the filtrate was concentrated.

The carbamate intermediate was dissolved in MeOH (10 mL) and stirred for 1 hour at 40° C. The solution was cooled to room temperature and concentrated via rotary evaporation. MS calculated for $C_{12}H_{12}ClN$+H: 206, observed: 206.

Step G. N-tert-Butyl carbamate-5-chloro-8-methylene-1,2,3,3a,8,8a-hexahydro-2-aza-cyclopenta[a]indene.

Di-tert-butyl dicarbonate (0.43 g, 2.00 mmol) and DIEA (1.0 mL, 6.0 mmol) were added to a solution of 5-chloro-8-methylene-1,2,3,3a,8,8a-hexahydro-2-aza-cyclopenta[a]indene (2.0 mmol) in $CH_2Cl_2$ (10 mL) at 0° C. The reaction mixture was stirred for 2 hours at from 0° C. to room temperature, then quenched with aqueous HCl (10 mL, 0.1 M). The organic extracts were washed with brine, dried over $MgSO_4$, and concentrated to afford the subtitle compound in quantitative yield. MS calculated for $C_{17}H_{20}ClNO_2$+H: 306, observed: 306.

Step H. N-tert-Butyl carbamate-5-chloro-8-methyl-1,2,3,3a,8,8a-hexahydro-2-aza-cyclopenta[a]indene.

N-tert-Butyl carbamate-5-chloro-8-methylene-1,2,3,3a,8,8a-hexahydro-2-aza-cyclopenta[a]indene (0.6 g, 2.0 mmol) was dissolved in EtOAc (10 mL) and purged with $N_2$. Palladium on carbon (0.2 g, 10 wt. %) was added and the flask was purged with $N_2$, and then charged with a balloon of $H_2$. The reaction mixture was stirred for 2 hours at room temperature then filtered through celite. The celite was washed with EtOAc, and the filtrate was concentrated to afford the subtitle compound in quantitative yield. MS calculated for $C_{17}H_{22}ClNO_2$+H: 308, observed: 308.

Step I. 5-Chloro-8-methyl-1,2,3,3a,8,8a-hexahydroindeno[1,2-c]pyrrole.

N-tert-Butyl carbamate-5-chloro-8-methyl-1,2,3,3a,8,8a-hexahydro-2-aza-cyclopenta[a]indene (10 mg, 0.03 mmol) was dissolved in an HCl solution (3 mL, 4 M in dioxane). The reaction was stirred for 2 hours at room temperature, and then concentrated to afford the title compound. An aliquot of the crude product was purified by reverse-phase liquid chromatography to afford the title compound. $^1$H NMR ($d_6$-DMSO 300 MHz) * 7.21 (m, 3H), 3.68 (m, 1H), 3.31 (m, 2H), 2.92 (m, 3H), 2.45 (m, 1H), 1.22 (d, 3H) ppm. MS calculated for $C_{12}H_{14}ClN$+H: 208, observed: 208.

Example 21

5-Methyl-6-chloro-8-methyl-1,2,3,3a,8,8a-hexahydroindeno[1,2-c]pyrrole

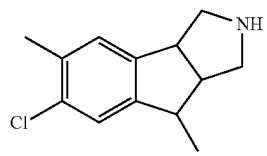

Step A. N-Ethylcarbamate-5-methyl-8-methyl-1,2,3,3a,8,8a-hexahydroindeno[1,2-c]pyrrole. (Scheme 3)

Ethyl chloroformate (0.29 mL, 3.0 mmol) and DIEA (1.6 mL, 9.0 mmol) were added to a solution of 5-methyl-8-methyl-1,2,3,3a,8,8a-hexahydroindeno[1,2-c]pyrrole (from Example 13, Step F) (0.56 g, 3.0 mmol) in $CH_2Cl_2$ (15 mL) at 0° C. The reaction was stirred for 2 hours from 0° C. to room temperature. The reaction was quenched with aqueous HCl (15 mL, 1M). The desired product was extracted with $CH_2Cl_2$ (3×15 mL). The organic extracts were washed with brine, dried over $MgSO_4$, and concentrated. The crude product was purified by column chromatography ($SiO_2$) using a 10-60% EtOAc-hexanes gradient to afford 0.36 g (46%) of the subtitle compound. MS calculated for $C_{16}H_{21}NO_2$+H: 260, observed: 260.

Step B. N-Ethylcarbamate-5-methyl-6-chloro-8-methyl-1,2,3,3a,8,8a-hexahydroindeno[1,2-c]pyrrole.

NCS (27 mg, 0.2 mmol) and acetic acid (1 mL) were added to a solution of N-Ethylcarbamate-5-methyl-8-methyl-1,2,3,3a,8,8a-hexahydroindeno[1,2-c]pyrrole (50 mg, 0.2 mmol) in DCE (1 mL). The reaction solution was stirred for 3 hours at 60° C. The reaction was diluted with $CH_2Cl_2$ (3 mL) and $H_2O$ (3 mL) and filtered through an Extrelut column. The column was washed with $CH_2Cl_2$ and the filtrate was concentrated. The crude product was purified by column chromatography ($SiO_2$) using a 0-60% ethyl acetate-hexanes gradient to afford the subtitle compound. MS calculated for $C_{16}H_{20}ClNO_2$+H: 294, observed: 294.

Step C. 5-Methyl-6-chloro-8-methyl-1,2,3,3a,8,8a-hexahydroindeno[1,2-c]pyrrole.

The title compound was prepared by the method of Example 3, Step B utilizing N-Ethylcarbamate-5-methyl-6-chloro-8-methyl-1,2,3,3a,8,8a-hexahydroindeno[1,2-c]pyrrole. The crude product was purified by reverse-phase liquid chromatography to afford the title compound. MS calculated for $C_{13}H_{16}ClN$+H: 222, observed: 222.

Example 22

5-Methyl-6-bromo-8-methyl-1,2,3,3a,8,8a-hexahydroindeno[1,2-c]pyrrole

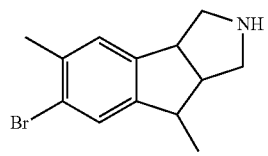

Step A. N-Ethylcarbamate-5-methyl-6-bromo-8-methyl-1,2,3,3a,8,8a-hexahydroindeno[1,2-c]pyrrole. (Scheme 3)

NBS (34 mg, 0.2 mmol) was added to a solution of N-Ethylcarbamate-5-methyl-8-methyl-1,2,3,3a,8,8a-hexahydroindeno[1,2-c]pyrrole (from Example 21, Step A) (50 mg, 0.2 mmol) in acetonitrile (1 mL), and stirred overnight at room temperature. The reaction was diluted with $CH_2Cl_2$ (3 mL) and $H_2O$ (3 mL) and filtered through an Extrelut column. The column was washed with $CH_2Cl_2$ and the filtrate was concentrated. The crude product was purified by column chromatography ($SiO_2$) using a 0-50% EtOAc-hexanes gradient to afford the subtitle compound. MS calculated for $C_{16}H_{20}BrNO_2$+H: 338, observed: 338.

Step C. 5-Methyl-6-bromo-8-methyl-1,2,3,3a,8,8a-hexahydroindeno[1,2-c]pyrrole.

The title compound was prepared by the method of Example 3, Step B utilizing N-Ethylcarbamate-5-methyl-6-bromo-8-methyl-1,2,3,3a,8,8a-hexahydroindeno[1,2-c]pyrrole. The crude product was purified by reverse-phase liquid chromatography to afford the title compound. $^1$H NMR ($d_6$-DMSO 300 MHz) * 7.29 (s, 1H), 7.12 (s, 1H), 3.70 (m, 3H), 2.92 (m, 3H), 2.45 (m, 1H), 2.29 (s, 3H), 1.22 (d, 3H) ppm. MS calculated for $C_{13}H_{16}BrN$+H: 266, observed: 266.

Example 23

5-Chloro-6-methyl-8-methyl-1,2,3,3a,8,8a-hexahydroindeno[1,2-c]pyrrole

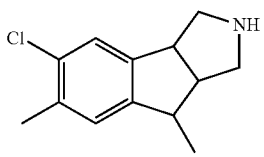

Step A. N-Ethylcarbamate-6-methyl-8-methyl-1,2,3,3a,8,8a-hexahydroindeno[1,2-c]pyrrole. (Scheme 3)

The subtitle compound was prepared by the method of Example 21, Step A utilizing 6-methyl-8-methyl-1,2,3,3a,8,8a-hexahydroindeno[1,2-c]pyrrole (from Example 15, Step F) (1.8 mmol). The crude product was purified by column chromatography ($SiO_2$) using a 10-60% EtOAc-hexanes gradient to afford 0.25 g (54%) of the subtitle compound. MS calculated for $C_{16}H_{21}NO_2$+H: 260, observed: 260.

Step B. N-Ethylcarbamate-5-chloro-6-methyl-8-methyl-1,2,3,3a,8,8a-hexahydroindeno[1,2-c]pyrrole.

The subtitle compound was prepared by the method of Example 21, Step B utilizing N-Ethylcarbamate-6-methyl-8-methyl-1,2,3,3a,8,8a-hexahydroindeno[1,2-c]pyrrole (0.2 mmol). The crude product was purified by column chromatography ($SiO_2$) using a 0-60 EtOAc-hexanes gradient to afford the subtitle compound. MS calculated for $C_{16}H_{20}ClNO_2$+H: 294, observed: 294.

Step C. 5-Chloro-6-methyl-8-methyl-1,2,3,3a,8,8a-hexahydroindeno[1,2-c]pyrrole.

The title compound was prepared by the method of Example 3, Step B utilizing N-Ethylcarbamate-5-chloro-6-methyl-8-methyl-1,2,3,3a,8,8a-hexahydroindeno[1,2-c]pyrrole. The crude product was purified by reverse-phase liquid chromatography to afford the title compound. $^1$H NMR ($d_6$-DMSO 300 MHz) * 7.21 (s, 1H), 7.10 (s, 1H), 3.61 (m, 1H), 3.29 (m, 2H), 2.88 (m, 3H), 2.45 (m, 1H), 2.29 (s, 3H), 1.22 (d, 3H) ppm. MS calculated for $C_{13}H_{16}ClN$+H: 222, observed: 222.

Example 24

5-Bromo-6-methyl-8-methyl-1,2,3,3a,8,8a-hexahydroindeno[1,2-c]pyrrole

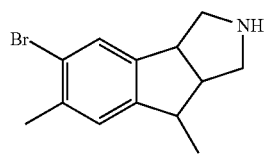

Step A. N-Ethylcarbamate-5-bromo-6-methyl-8-methyl-1,2,3,3a,8,8a-hexahydroindeno[1,2-c]pyrrole. (Scheme 3)

The subtitle compound was prepared by the method of Example 22, Step A utilizing N-Ethylcarbamate-6-methyl-8-methyl-1,2,3,3a,8,8a-hexahydroindeno[1,2-c]pyrrole (from Example 23, Step A) (0.2 mmol). The crude product was purified by column chromatography ($SiO_2$) using a 0-50% EtOAc-hexanes gradient to afford the subtitle compound. MS calculated for $C_{16}H_{20}BrNO_2$+H: 338, observed: 338.

Step B. 5-Bromo-6-methyl-8-methyl-1,2,3,3a,8,8a-hexahydroindeno[1,2-c]pyrrole.

The title compound was prepared by the method of Example 3, Step B utilizing N-Ethylcarbamate-5-bromo-6-methyl-8-methyl-1,2,3,3a,8,8a-hexahydroindeno[1,2-c]pyrrole. The crude product was purified by reverse-phase liquid chromatography to afford the title compound. MS calculated for $C_{13}H_{16}BrN$+H: 266, observed: 266.

Example 25

4-Chloro-5-methoxy-8-methyl-1,2,3,3a,8,8a-hexahydroindeno[1,2-c]pyrrole

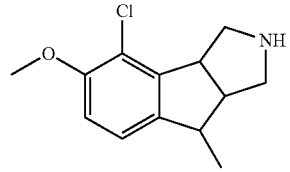 [SMILES: COc1ccc2c(c1Cl)C1CNCC1C2C]

Step A. N-Ethylcarbamate-4-chloro-5-methoxy-8-methyl-1,2,3,3a,8,8a-hexahydroindeno[1,2-c]pyrrole. (Scheme 1)

N-chlorosuccinimide (0.39 g, 2.9 mmol) and acetic acid (3 mL) were added to a solution of N-ethylcarbamate-5-methoxy-8-methyl-1,2,3,3a,8,8a-hexahydroindeno[1,2-c]pyrrole (from Example 2, Step A) (0.80 g, 2.9 mmol) in DCE (3 mL). The resulting solution was stirred for 3 hours at 60° C. The reaction mixture was cooled to room temperature, diluted with $CH_2Cl_2$ (50 mL), and washed with $H_2O$ (50 mL). The organic extract was dried over $MgSO_4$ and concentrated. The crude product was purified by column chromatography ($SiO_2$) using a 0-35% EtOAc-hexanes gradient to afford 50 mg (6%) of the subtitle compound (The major product is N-ethylcarbamate-5-methoxy-6-chloro-8-methyl-1,2,3,3a, 8,8a-hexahydroindeno[1,2-c]pyrrole, 78%). MS calculated for $C_{16}H_{20}ClNO_3$+H: 310, observed: 310.

Step B. 4-Chloro-5-methoxy-8-methyl-1,2,3,3a,8,8a-hexahydroindeno[1,2-c]pyrrole.

The title compound was prepared by the method of Example 3, Step B utilizing N-Ethylcarbamate-4-chloro-5-methoxy-8-methyl-1,2,3,3a,8,8a-hexahydroindeno[1,2-c] pyrrole (0.16 mmol). The crude product was purified by reverse-phase liquid chromatography to afford the title compound. $^1$H NMR (d$_6$-DMSO 300 MHz) * 7.08 (d, 1H), 6.98 (d, 1H), 3.81 (s, 3H), 3.64 (m, 1H), 3.47 (m, 1H), 3.29 (m, 1H), 2.91 (m, 3H), 2.45 (m, 1H), 1.21 (d, 3H) ppm. MS calculated for $C_{13}H_{16}ClNO$+H: 238, observed: 238.

Example 26

5,6-Dichloro-8-methyl-1,2,3,3a,8,8a-hexahydroindeno[1,2-c]pyrrole

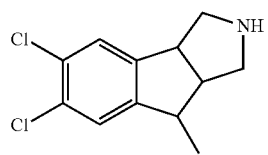

Step A. 3-(3,4-Dichloro-phenyl)-acrylic acid ethyl ester. (Scheme 3)

The subtitle compound was prepared by the method of Example 13, Step A utilizing 3,4-dichlorobenzaldehyde (9.0 mmol). The crude product was obtained without further purification. MS calculated for $C_{11}H_{10}Cl_2O_2$+H: 245, observed: 245.

Step B. 1-Benzyl-4-(3,4-dichloro-phenyl)-pyrrolidine-3-carboxylic acid ethyl ester.

The subtitle compound was prepared by the method of Example 1, Step C utilizing 3-(3,4-dichloro-phenyl)-acrylic acid ethyl ester (9.0 mmol). The crude product was purified by column chromatography (SiO$_2$) using a 10-50% EtOAc-hexanes gradient to afford the subtitle compound in quantitative yield. MS calculated for $C_{20}H_{22}Cl_2NO_2$+H: 378, observed: 378.

Step C. 1-Benzyl-4-(3,4-dichloro-phenyl)-pyrrolidine-3-carboxylic acid.

The subtitle compound was prepared by the method of Example 13, Step C utilizing 1-benzyl-4-(3,4-dichloro-phenyl)-pyrrolidine-3-carboxylic acid ethyl ester (9.0 mmol). The crude product was obtained without further purification. MS calculated for $C_{18}H_{18}Cl_2NO_2$+H: 350, observed: 350.

Step D. 2-Benzyl-5,6-dichloro-2,3,3a,8a-tetrahydro-1H-2-aza-cyclopenta[a]inden-8-one.

The subtitle compound was prepared by the method of Example 13, Step D utilizing 1-benzyl-4-(3,4-dichloro-phenyl)-pyrrolidine-3-carboxylic acid (9.0 mmol). The crude product was purified by column chromatography (SiO$_2$) using a 0-50% EtOAC-hexanes gradient to afford 0.59 g (20%—four steps) of the subtitle compound and 0.30 g (10%—four steps) of the regioisomeric 2-benzyl-6,7-dichloro-2,3,3a,8a-tetrahydro-1H-2-aza-cyclopenta[a]inden-8-one. MS calculated for $C_{18}H_{16}Cl_2NO$+H: 332, observed: 332.

Step E. 2-Benzyl-5,6-dichloro-8-methylene-1,2,3,3a,8,8a-hexahydro-2-aza-cyclopenta[a]indene.

The subtitle compound was prepared by the method of Example 1, Step D utilizing 2-benzyl-5,6-dichloro-2,3,3a,8a-tetrahydro-1H-2-aza-cyclopenta[a]inden-8-one (0.9 mmol). The crude product was purified by silica plug eluting with EtOAc-hexanes (3/1, v/v) to afford the subtitle compound. MS calculated for $C_{19}H_{18}Cl_2N$+H: 330, observed: 330.

Step F. 5,6-Dichloro-8-methylene-1,2,3,3a,8,8a-hexahydro-2-aza-cyclopenta[a]indene.

The subtitle compound was prepared by the method of Example 20, Step F utilizing 2-benzyl-5,6-dichloro-8-methylene-1,2,3,3a,8,8a-hexahydro-2-aza-cyclopenta[a]indene (0.9 mmol). The crude product was obtained without further purification. MS calculated for $C_{12}H_{12}Cl_2N$+H: 240, observed: 240.

Step G. N-tert-Butyl carbamate-5,6-dichloro-8-methylene-1,2,3,3a,8,8a-hexahydro-2-aza-cyclopenta[a]indene.

The subtitle compound was prepared by the method of Example 20, Step G utilizing 5,6-dichloro-8-methylene-1,2,3,3a,8,8a-hexahydro-2-aza-cyclopenta[a]indene (0.9 mmol). The crude product was obtained without further purification. MS calculated for $C_{17}H_{20}Cl_2NO_2$+H: 340, observed: 340.

Step H. N-tert-Butyl carbamate-5,6-dichloro-8-methyl-1,2,3,3a,8,8a-hexahydro-2-aza-cyclopenta[a]indene.

The subtitle compound was prepared by the method of Example 20, Step H utilizing N-tert-butyl carbamate-5,6-dichloro-8-methylene-1,2,3,3a,8,8a-hexahydro-2-aza-cyclopenta[a]indene (0.9 mmol). The crude product was obtained without further purification. MS calculated for $C_{17}H_{22}Cl_2NO_2$+H: 342, observed: 342.

Step I. 5,6-Dichloro-8-methyl-1,2,3,3a,8,8a-hexahydroindeno[1,2-c]pyrrole.

The subtitle compound was prepared by the method of Example 20, Step I utilizing N-tert-butyl carbamate-5,6-dichloro-8-methyl-1,2,3,3a,8,8a-hexahydro-2-aza-cyclopenta[a]indene. An aliquot of the crude product was purified by reverse-phase liquid chromatography to afford the title compound. MS calculated for $C_{12}H_{14}Cl_2N$+H: 242, observed: 242.

Example 27

6,7-Dichloro-8-methyl-1,2,3,3a,8,8a-hexahydroindeno[1,2-c]pyrrole

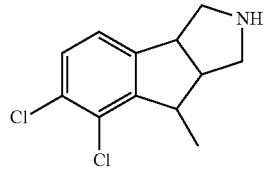

Step A. 2-Benzyl-6,7-dichloro-8-methylene-1,2,3,3a,8, 8a-hexahydro-2-aza-cyclopenta[a]indene. (Scheme 3)

The subtitle compound was prepared by the method of Example 1, Step D utilizing 2-benzyl-6,7-dichloro-2,3,3a,8a-tetrahydro-1H-2-aza-cyclopenta[a]inden-8-one (from Example 26, Step D, regioisomer) (1.8 mmol). The crude product was purified by silica plug eluting with EtOAc-hexanes (3/1, v/v) to afford the subtitle compound. MS calculated for $C_{19}H_{18}Cl_2N$+H: 330, observed: 330.

Step B. 6,7-Dichloro-8-methylene-1,2,3,3a,8,8a-hexahydro-2-aza-cyclopenta[a]indene.

The subtitle compound was prepared by the method of Example 20, Step F utilizing 2-benzyl-6,7-dichloro-8-methylene-1,2,3,3a,8,8a-hexahydro-2-aza-cyclopenta[a]indene (1.8 mmol). The crude product was obtained without further purification. MS calculated for $C_{12}H_{12}Cl_2N+H$: 240, observed: 240.

Step C. N-tert-Butyl carbamate-6,7-dichloro-8-methylene-1,2,3,3a,8,8a-hexahydro-2-aza-cyclopenta[a]indene.

The subtitle compound was prepared by the method of Example 20, Step G utilizing 6,7-dichloro-8-methylene-1,2,3,3a,8,8a-hexahydro-2-aza-cyclopenta[a]indene (0.9 mmol). The crude product was obtained without further purification. MS calculated for $C_{17}H_{20}Cl_2NO_2+H$: 340, observed: 340.

Step D. N-tert-Butyl carbamate-6,7-dichloro-8-methyl-1,2,3,3a,8,8a-hexahydro-2-aza-cyclopenta[a]indene.

The subtitle compound was prepared by the method of Example 20, Step H utilizing N-tert-butyl carbamate-6,7-dichloro-8-methylene-1,2,3,3a,8,8a-hexahydro-2-aza-cyclopenta[a]indene (1.8 mmol). The crude product was obtained without further purification. MS calculated for $C_{17}H_{22}Cl_2NO_2+H$: 342, observed: 342.

Step E. 6,7-Dichloro-8-methyl-1,2,3,3a,8,8a-hexahydroindeno[1,2-c]pyrrole.

The title compound was prepared by the method of Example 20, Step I utilizing N-tert-butyl carbamate-6,7-dichloro-8-methyl-1,2,3,3a,8,8a-hexahydro-2-aza-cyclopenta[a]indene. An aliquot of the crude product was purified by reverse-phase liquid chromatography to afford the title compound. $^1$H NMR (d$_6$-DMSO 300 MHz) * 7.46 (d, 1H), 7.20 (d, 1H), 3.68 (m, 1H), 3.51 (m, 1H), 3.23 (m, 1H), 3.08 (m, 1H), 3.88 (m, 3H), 1.37 (d, 3H) ppm. MS calculated for $C_{12}H_{14}Cl_2N+H$: 242, observed: 242.

Example 28

4,6-Dichloro-8-methyl-1,2,3,3a,8,8a-hexahydroindeno[1,2-c]pyrrole

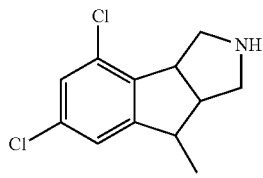

Step A. 3-(2,4-Dichloro-phenyl)-acrylic acid ethyl ester. (Scheme 3)

The subtitle compound was prepared by the method of Example 13, Step A utilizing 3,4-dichlorobenzaldehyde (18.0 mmol). The crude product was obtained without further purification. MS calculated for $C_{11}H_{10}Cl_2O_2+H$: 245, observed: 245.

Step B. 1-Benzyl-4-(2,4-dichloro-phenyl)-pyrrolidine-3-carboxylic acid ethyl ester.

The subtitle compound was prepared by the method of Example 1, Step C utilizing 3-(2,4-dichloro-phenyl)-acrylic acid ethyl ester (18.0 mmol). The crude product was purified by column chromatography (SiO$_2$) using a 10-50% EtOAc-hexanes gradient to afford the subtitle compound in quantitative yield. MS calculated for $C_{20}H_{22}Cl_2NO_2+H$: 378, observed: 378.

Step C. 1-Benzyl-4-(2,4-dichloro-phenyl)-pyrrolidine-3-carboxylic acid.

The subtitle compound was prepared by the method of Example 13, Step C utilizing 1-benzyl-4-(2,4-dichloro-phenyl)-pyrrolidine-3-carboxylic acid ethyl ester (18.0 mmol). The crude product was obtained without further purification. MS calculated for $C_{18}H_{18}Cl_2NO_2+H$: 350, observed: 350.

Step D. 2-Benzyl-4,6-dichloro-2,3,3a,8a-tetrahydro-1H-2-aza-cyclopenta[a]inden-8-one.

The subtitle compound was prepared by the method of Example 13, Step D utilizing 1-benzyl-4-(2,4-dichloro-phenyl)-pyrrolidine-3-carboxylic acid (18.0 mmol). The crude product was purified by column chromatography (SiO$_2$) using a 0-50% EtOAc-hexanes gradient to afford 1.5 g (25%—four steps) of the subtitle compound. MS calculated for $C_{18}H_{16}Cl_2NO+H$: 332, observed: 332.

Step E. 2-Benzyl-4,6-dichloro-8-methylene-1,2,3,3a,8,8a-hexahydro-2-aza-cyclopenta[a]indene.

The subtitle compound was prepared by the method of Example 1, Step D utilizing 2-benzyl-4,6-dichloro-2,3,3a,8a-tetrahydro-1H-2-aza-cyclopenta[a]inden-8-one (4.5 mmol). The crude product was purified by silica plug eluting with EtOAc-hexanes (3/1, v/v) to afford the subtitle compound. MS calculated for $C_{19}H_{18}Cl_2N+H$: 330, observed: 330.

Step F. 4,6-Dichloro-8-methylene-1,2,3,3a,8,8a-hexahydro-2-aza-cyclopenta[a]indene.

The subtitle compound was prepared by the method of Example 20, Step F utilizing 2-benzyl-4,6-dichloro-8-methylene-1,2,3,3a,8,8a-hexahydro-2-aza-cyclopenta[a]indene (4.5 mmol). The crude product was obtained without further purification. MS calculated for $C_{12}H_{12}Cl_2N+H$: 240, observed: 240.

Step G. N-tert-Butyl carbamate-4,6-dichloro-8-methylene-1,2,3,3a,8,8a-hexahydro-2-aza-cyclopenta[a]indene.

The subtitle compound was prepared by the method of Example 20, Step G utilizing 4,6-dichloro-8-methylene-1,2,3a,8,8a-hexahydro-2-aza-cyclopenta[a]indene (4.5 mmol). The crude product was obtained without further purification. MS calculated for $C_{17}H_{20}Cl_2NO_2+H$: 340, observed: 340.

Step H. N-tert-Butyl carbamate-4,6-dichloro-8-methyl-1,2,3,3a,8,8a-hexahydro-2-aza-cyclopenta[a]indene.

The subtitle compound was prepared by the method of Example 20, Step H utilizing N-tert-butyl carbamate-4,6-dichloro-8-methylene-1,2,3,3a,8,8a-hexahydro-2-aza-cyclopenta[a]indene (0.9 mmol) to afford 0.33 g (22%-4 steps) of the subtitle compound. MS calculated for $C_{17}H_{22}Cl_2NO_2+H$: 342, observed: 342.

Step I. 4,6-Dichloro-8-methyl-1,2,3,3a,8,8a-hexahydroindeno[1,2-c]pyrrole.

The title compound was prepared by the method of Example 20, Step I utilizing N-tert-butyl carbamate-4,6-dichloro-8-methyl-1,2,3,3a,8,8a-hexahydro-2-aza-cyclopenta[a]indene. An aliquot of the crude product was purified by reverse-phase liquid chromatography to afford the title compound. MS calculated for $C_{12}H_{14}Cl_2N+H$: 242, observed: 242.

Example 29

5-Ethoxy-6-chloro-8-methyl-1,2,3,3a,8,8a-hexahydroindeno[1,2-c]pyrrole

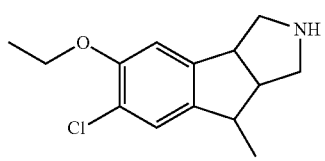 [SMILES: CCOc1cc2c(cc1Cl)C(C)C1CNCC21]

Step A. N-Ethylcarbamate-5-hydroxy-6-chloro-8-methyl-1,2,3,3a,8,8a-hexahydroindeno[1,2-c]pyrrole. (Scheme 1)

BBr$_3$ (0.3 mL, 0.30 mmol, 1 M in CH$_2$Cl$_2$) was added to a solution of N-Ethylcarbamate-5-methoxy-6-chloro-8-methyl-1,2,3,3a,8,8a-hexahydroindeno[1,2-c]pyrrole (from Example 3, Step A) (46 mg, 0.15 mmol) at 0° C., and stirred overnight at room temperature. The reaction solution was quenched with H$_2$O and filtered through an Extrelut column. The column was washed with CH$_2$Cl$_2$, and the filtrate was concentrated. The crude product was obtained without further purification. MS calculated for C$_{16}$H$_{18}$ClNO$_3$+H: 296, observed: 296.

Step B. N-Ethylcarbamate-5-ethoxy-6-chloro-8-methyl-1,2,3,3a,8,8a-hexahydroindeno[1,2-c]pyrrole.

Bromoethane (17 mL, 0.23 mmol) and K$_2$CO$_3$ (105 mg, 0.75 mmol) were added to a solution of N-ethylcarbamate-5-hydroxy-6-chloro-8-methyl-1,2,3,3a,8,8a-hexahydroindeno[1,2-c]pyrrole (44 mg, 0.15 mmol) in CH$_3$CN (1.5 mL). The reaction was stirred overnight at 70° C., diluted with H$_2$O and CH$_2$Cl$_2$, and filtered through an Extrelut column. The column was washed with CH$_2$Cl$_2$ and the filtrate was concentrated. The crude product was obtained without further purification. MS calculated for C$_{17}$H$_{22}$ClNO$_3$+H: 324, observed: 324.

Step C. 5-Ethoxy-6-chloro-8-methyl-1,2,3,3a,8,8a-hexahydroindeno[1,2-c]pyrrole.

The title compound was prepared by the method of Example 3, Step B utilizing N-ethylcarbamate-5-ethoxy-6-chloro-8-methyl-1,2,3,3a,8,8a-hexahydroindeno[1,2-c]pyrrole (0.15 mmol). The crude product was purified by reverse-phase liquid chromatography to afford the title compound. $^1$H NMR (d$_6$-DMSO 300 MHz) * 7.18 (s, 1H), 7.00 (s, 1H), 4.09 (m, 2H), 3.68 (m, 1H), 3.31 (m, 2H), 2.99 (m, 3H), 2.45 (m, 1H), 1.33 (t, 3H), 1.21 (d, 3H) ppm. MS calculated for C$_{14}$H$_{18}$ClNO+H: 252, observed: 252.

Example 30

5-Methoxy-6-bromo-8-methyl-1,2,3,3a,8,8a-hexahydroindeno[1,2-c]pyrrole

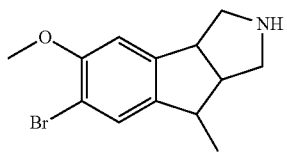 [SMILES: COc1cc2c(cc1Br)C(C)C1CNCC21]

Step A. N-Ethylcarbamate-5-methoxy-6-bromo-8-methyl-1,2,3,3a,8,8a-hexahydroindeno[1,2-c]pyrrole. (Scheme 1)

NBS (70 mg, 0.4 mmol) was added to a solution of N-methylcarbamate-5-methoxy-8-methyl-1,2,3,3a,8,8a-hexahydroindeno[1,2-c]pyrrole (from Example 2, step A) (0.1 g, 0.36 mmol) in CH$_3$CN (3.6 mL), and stirred overnight at room temperature. The reaction was diluted with H$_2$O and EtOAc and filtered through an Extrelut column. The column was washed with EtOAc and the filtrate was concentrated to afford 120 mg (94%) of the subtitle compound. MS calculated for C$_{16}$H$_{20}$BrNO$_3$+H: 342, observed: 342.

Step B. 5-Methoxy-6-bromo-8-methyl-1,2,3,3a,8,8a-hexahydroindeno[1,2-c]pyrrole.

The title compound was prepared by the method of Example 3, Step B utilizing N-ethylcarbamate-5-methoxy-6-bromo-8-methyl-1,2,3,3a,8,8a-hexahydroindeno[1,2-c]pyrrole (0.17 mmol). The crude product was purified by reverse-phase liquid chromatography to afford the title compound. $^1$H NMR (d$_6$-DMSO 300 MHz) * 7.29 (s, 1H), 6.93 (s, 1H), 3.81 (s, 3H), 3.61 (m, 1H), 3.28 (m, 2H), 2.98 (m, 1H), 2.83 (m, 2H), 2.45 (m, 1H), 1.33 (t, 3H), 1.21 (d, 3H) ppm. MS calculated for C$_{13}$H$_{16}$BrNO+H: 282, observed: 282.

Example 31

5-Hydroxy-6-bromo-8-methyl-1,2,3,3a,8,8a-hexahydroindeno[1,2-c]pyrrole

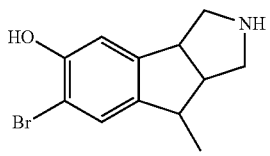

Step A. N-Ethylcarbamate-5-hydroxy-6-bromo-8-methyl-1,2,3,3a,8,8a-hexahydroindeno[1,2-c]pyrrole. (Scheme 1)

The subtitle compound was prepared by the method of Example 29, Step A utilizing N-ethylcarbamate-5-methoxy-6-bromo-8-methyl-1,2,3,3a,8,8a-hexahydroindeno[1,2-c]pyrrole (from Example 30, Step A) (0.09 mmol). The crude product was obtained without further purification. MS calculated for C$_{15}$H$_{18}$BrNO$_3$+H: 340, observed: 340.

Step B. 5-Hydroxy-6-bromo-8-methyl-1,2,3,3a,8,8a-hexahydroindeno[1,2-c]pyrrole.

The title compound was prepared by the method of Example 3, Step B utilizing N-ethylcarbamate-5-hydroxy-6-bromo-8-methyl-1,2,3,3a,8,8a-hexahydroindeno[1,2-c]pyrrole (0.09 mmol). The crude product was purified by reverse-phase liquid chromatography to afford the title compound. MS calculated for C$_{12}$H$_{14}$BrNO+H: 268, observed: 268.

Example 32

5-Methoxy-6-(2-thienyl)-8-methyl-1,2,3,3a,8,8a-hexahydroindeno[1,2-c]pyrrole

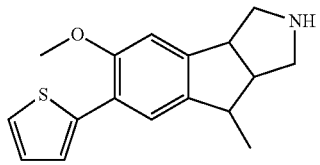 [SMILES: COc1cc2c(cc1-c1cccs1)C(C)C1CNCC21]

Step A. N-Ethylcarbamate-5-methoxy-6-(2-thienyl)-8-methyl-1,2,3,3a,8,8a-hexahydroindeno[1,2-c]pyrrole. (Scheme 1)

Thiophene-2-boronic acid (44 mg, 0.34 mmol), Pd(PPh$_3$)$_4$ (19 mg, 0.02 mmol), K$_2$CO$_3$ (71 mg, 0.51 mmol), and H$_2$O (0.17 mL) were added to a solution of N-ethylcarbamate-5-methoxy-6-bromo-8-methyl-1,2,3,3a,8,8a-hexahydroindeno[1,2-c]pyrrole (from Example 30, Step A) (60 mg, 0.17 mmol) in dioxane (3 mL) and stirred overnight at 100° C. The reaction mixture was diluted with EtOAC and H$_2$O, and filtered through an Extrelut column. The column was washed with EtOAc, and the filtrate was concentrated. The crude product was purified via a silica plug eluting with Hexanes/EtOAc (2/1, v/v). MS calculated for C$_{20}$H$_{25}$NO$_3$S+H: 358, observed: 358.

Step B. 5-Methoxy-6-(2-thienyl)-8-methyl-1,2,3,3a,8,8a-hexahydroindeno[1,2-c]pyrrole.

The title compound was prepared by the method of Example 3, Step B utilizing N-ethylcarbamate-5-methoxy-6-(2-thienyl)-8-methyl-1,2,3,3a,8,8a-hexahydroindeno[1,2-c]pyrrole (0.17 mmol). The crude product was purified by reverse-phase liquid chromatography to afford the title compound. $^1$H NMR (d$_6$-DMSO 300 MHz) *7.52 (d, 1H), 7.49 (d, 1H), 7.41 (s, 1H), 7.10 (t, 1H), 6.97 (s, 1H), 3.88 (s, 3H), 3.66 (m, 1H), 3.31 (m, 2H), 3.00 (m, 1H), 2.88 (m, 2H), 2.45 (m, 1H), 1.29 (d, 3H) ppm. MS calculated for $C_{17}H_{19}NOS$+H: 286, observed: 286.

Example 33

5-Methoxy-6-cyano-8-methyl-1,2,3,3a,8,8a-hexahydroindeno[1,2-c]pyrrole

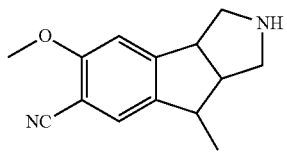 [SMILES: COc1cc2c(cc1C#N)C(C)C1CNCC21]

Step A. N-Ethylcarbamate-5-methoxy-6-cyano-8-methyl-1,2,3,3a,8,8a-hexahydroindeno[1,2-c]pyrrole. (Scheme 1)

CuCN (68 mg, 0.85 mmol) was added to a solution of N-ethylcarbamate-5-methoxy-6-bromo-8-methyl-1,2,3,3a,8,8a-hexahydroindeno[1,2-c]pyrrole (from Example 30, Step A) (60 mg, 0.17 mmol) in DMF (1.7 mL), and stirred overnight at 100° C. The reaction mixture was diluted with EtOAC and H$_2$O, and filtered through an Extrelut column. The column was washed with EtOAc, and the filtrate was concentrated. The crude product was purified via a silica plug eluting with Hexanes/EtOAc (2/1, v/v). MS calculated for $C_{17}H_{20}N_2O_3$+H: 301, observed: 301.

Step B. 5-Methoxy-6-cyano-8-methyl-1,2,3,3a,8,8a-hexahydroindeno[1,2-c]pyrrole.

The title compound was prepared by the method of Example 3, Step B utilizing N-ethylcarbamate-5-methoxy-6-cyano-8-methyl-1,2,3,3a,8,8a-hexahydroindeno[1,2-c]pyrrole (0.17 mmol). The crude product was purified by reverse-phase liquid chromatography to afford the title compound. $^1$H NMR (d$_6$-DMSO 300 MHz) * 7.44 (s, 1H), 7.04 (s, 1H), 3.88 (s, 3H), 3.65 (m, 1H), 3.23 (m, 2H), 2.88 (m, 1H), 2.78 (m, 2H), 2.40 (m, 1H), 1.21 (d, 3H) ppm. MS calculated for $C_{14}H_{16}N_2O$+H: 229, observed: 229.

Example 34

4,5-Dimethoxy-8-methyl-1,2,3,3a,8,8a-hexahydroindeno[1,2-c]pyrrole

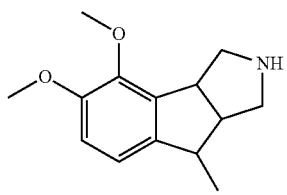 [SMILES: COc1ccc2c(c1OC)C1CNCC1C2C]

Step A. 3-Bromo-4,5-dimethoxy-1-indanone. (Scheme 3)

The subtitle compound was prepared by the method of Example 1, Step A utilizing 4,5-dimethoxy-1-indanone (26.0 mmol). The crude product was obtained without further purification. MS calculated for $C_{11}H_{11}BrO_3$+H: 271, observed: 271.

Step B. 4,5-Dimethoxy-inden-1-one.

The subtitle compound was prepared by the method of Example 1, Step B utilizing 3-bromo-4,5-dimethoxy-1-indanone (26.0 mmol). The crude product was obtained without further purification. MS calculated for $C_{11}H_{10}O_3$+H: 191, observed: 191.

Step C. 2-Benzyl-4,5-dimethoxy-2,3,3a,8a-tetrahydro-1H-2-aza-cyclopenta[a]inden-8-one.

The subtitle compound was prepared by the method of Example 1, Step C utilizing 4,5-dimethoxy-inden-1-one (26.0 mmol). The crude product was purified by silica plug eluting with hexanes/EtOAc (3/1, v/v) to afford 4.2 g (50%—3 steps) of the subtitle compound. MS calculated for $C_{20}H_{21}NO_3$+H: 324, observed: 324.

Step D. 2-Benzyl-4,5-dimethoxy-8-methylene-1,2,3,3a,8,8a-hexahydroindeno[1,2-c]pyrrole.

The subtitle compound was prepared by the method of Example 1, Step D utilizing 2-benzyl-4,5-dimethoxy-2,3,3a,8a-tetrahydro-1H-2-aza-cyclopenta[a]inden-8-one (13.0 mmol). The crude product was purified by silica plug eluting with hexanes/EtOAc (3/1, v/v) to afford the subtitle compound in quantitative yield. MS calculated for $C_{21}H_{23}NO_2$+H: 322, observed: 322.

Step E. 4,5-Dimethoxy-8-methyl-1,2,3,3a,8,8a-hexahydroindeno[1,2-c]pyrrole.

The subtitle compound was prepared by the method of Example 1, Step E utilizing 2-benzyl-4,5-dimethoxy-8-methylene-1,2,3,3a,8,8a-hexahydroindeno[1,2-c]pyrrole (13.0 mmol). The crude product was obtained without further purification. MS calculated for $C_{14}H_{19}NO_2$+H: 234, observed: 234.

Step F. N-Ethylcarbamate-4,5-dimethoxy-8-methyl-1,2,3,3a,8,8a-hexahydroindeno[1,2-c]pyrrole.

The subtitle compound was prepared by the method of Example 2, Step A utilizing 4,5-dimethoxy-8-methyl-1,2,3,3a,8,8a-hexahydroindeno[1,2-c]pyrrole (13.0 mmol). The crude product was purified by column chromatography (SiO$_2$) using a 0-50% EtOAc-hexanes gradient to afford the subtitle compound. MS calculated for $C_{17}H_{23}NO_4$+H: 306, observed: 306.

Step G. 4,5-Dimethoxy-8-methyl-1,2,3,3a,8,8a-hexahydroindeno[1,2-c]pyrrole.

The title compound was prepared by the method of Example 3, Step B utilizing N-ethylcarbamate-4,5-dimethoxy-8-methyl-1,2,3,3a,8,8a-hexahydroindeno[1,2-c]pyrrole (0.03 mmol). The crude product was purified by reverse-phase liquid chromatography to afford the title compound. $^1$H NMR (d$_6$-DMSO 300 MHz) * 6.88 (d, 1H), 6.79 (d, 1H), 3.72 (m, 7H), 3.32 (m, 1H), 3.21 (m, 2H), 2.84 (m, 3H), 2.40 (m, 1H), 1.19 (d, 3H) ppm. MS calculated for $C_{14}H_{19}NO_2$+H: 234, observed: 234.

Example 35

4,5-Dimethoxy-6-chloro-8-methyl-1,2,3,3a,8,8a-hexahydroindeno[1,2-c]pyrrole

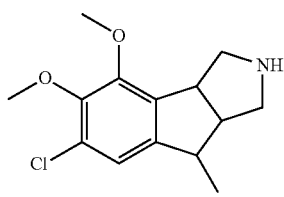 [SMILES: COc1c(Cl)cc2c(c1OC)C1CNCC1C2C]

Step A. N-Ethylcarbamate-4,5-dimethoxy-6-chloro-8-methyl-1,2,3,3a,8,8a-hexahydroindeno[1,2-c]pyrrole. (Scheme 3)

The subtitle compound was prepared by the method of Example 3, Step A utilizing N-ethylcarbamate-4,5-dimethoxy-8-methyl-1,2,3,3a,8,8a-hexahydroindeno[1,2-c]pyrrole (from Example 34, Step F) (0.58 mmol). The crude product was obtained without further purification. MS calculated for $C_{17}H_{22}ClNO_4$+H: 340, observed: 340.

Step B. 5-Methoxy-6-chloro-8-methyl-1,2,3,3a,8,8a-hexahydroindeno[1,2-c]pyrrole.

The title compound was prepared by the method of Example 3, Step B utilizing N-ethylcarbamate-4,5-dimethoxy-6-chloro-8-methyl-1,2,3,3a,8,8a-hexahydroindeno[1,2-c]pyrrole (0.12 mmol). The crude product was purified by reverse-phase liquid chromatography to afford the title compound. $^1$H NMR ($d_6$-DMSO 300 MHz) * 6.88 (d, 1H), 6.79 (d, 1H), 3.72 (m, 7H), 3.32 (m, 1H), 3.21 (m, 1H), 2.84 (m, 3H), 2.40 (m, 1H), 1.19 (d, 3H) ppm. MS calculated for $C_{14}H_{18}ClNO_2$+H: 268, observed: 268.

Example 36

4,5-Dimethoxy-8-methyl-1,2,3,3a,8,8a-hexahydroindeno[1,2-c]pyrrole

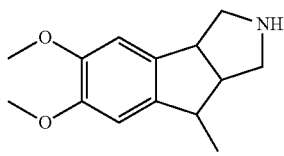 [SMILES: COc1cc2c(cc1OC)C1CNCC1C2C]

Step A. 3-Bromo-5,6-dimethoxy-1-indanone. (Scheme 3)

The subtitle compound was prepared by the method of Example 1, Step A utilizing 5,6-dimethoxy-1-indanone (52.0 mmol). The crude product was obtained without further purification. MS calculated for $C_{11}H_{11}BrO_3$+H: 271, observed: 271.

Step B. 5,6-Dimethoxy-inden-1-one.

The subtitle compound was prepared by the method of Example 1, Step B utilizing 3-bromo-5,6-dimethoxy-1-indanone (52.0 mmol). The crude product was obtained without further purification. MS calculated for $C_{11}H_{10}O_3$+H: 191, observed: 191.

Step C. 2-Benzyl-5,6-dimethoxy-2,3,3a,8a-tetrahydro-1H-2-aza-cyclopenta[a]inden-8-one.

The subtitle compound was prepared by the method of Example 1, Step C utilizing 5,6-dimethoxy-inden-1-one (52.0 mmol). The crude product was purified by silica plug eluting with hexanes/EtOAc (3/1, v/v) to afford the subtitle compound. MS calculated for $C_{20}H_{21}NO_3$+H: 324, observed: 324.

Step D. 2-Benzyl-5,6-dimethoxy-8-methylene-1,2,3,3a,8,8a-hexahydroindeno[1,2-c]pyrrole.

The subtitle compound was prepared by the method of Example 1, Step D utilizing 2-benzyl-5,6-dimethoxy-2,3,3a,8a-tetrahydro-1H-2-aza-cyclopenta[a]inden-8-one (3.1 mmol). The crude product was purified by silica plug eluting with hexanes/EtOAc (3/1, v/v) to afford the subtitle compound in quantitative yield. MS calculated for $C_{21}H_{23}NO_2$+H: 322, observed: 322.

Step E. 5,6-Dimethoxy-8-methyl-1,2,3,3a,8,8a-hexahydroindeno[1,2-c]pyrrole.

The subtitle compound was prepared by the method of Example 1, Step E utilizing 2-benzyl-5,6-dimethoxy-8-methylene-1,2,3,3a,8,8a-hexahydroindeno[1,2-c]pyrrole (3.1 mmol). The crude product was obtained without further purification. MS calculated for $C_{14}H_{19}NO_2$+H: 234, observed: 234.

Step F. N-tert-Butylcarbamate-4,5-dimethoxy-8-methyl-1,2,3,3a,8,8a-hexahydroindeno[1,2-c]pyrrole.

The subtitle compound was prepared by the method of Example 20, Step G utilizing 5,6-dimethoxy-8-methyl-1,2,3,3a,8,8a-hexahydroindeno[1,2-c]pyrrole (3.1 mmol). The crude product was purified by column chromatography (SiO$_2$) using a 0-50% EtOAc-hexanes gradient to afford the subtitle compound. MS calculated for $C_{19}H_{27}NO_4$+H: 334, observed: 334.

Step G. 4,5-Dimethoxy-8-methyl-1,2,3,3a,8,8a-hexahydroindeno[1,2-c]pyrrole.

The title compound was prepared by the method of Example 20, Step H utilizing N-tert-butylcarbamate-5,6-dimethoxy-8-methyl-1,2,3,3a,8,8a-hexahydroindeno[1,2-c]pyrrole (0.15 mmol). The crude product was purified by reverse-phase liquid chromatography to afford the title compound. $^1$H NMR ($d_6$-DMSO 300 MHz) * 6.92 (s, 1H), 6.80 (s, 1H), 3.72 (m, 7H), 3.55 (m, 1H), 3.21 (m, 4H), 2.65 (m, 1H), 1.26 (d, 3H) ppm. MS calculated for $C_{14}H_{19}NO_2$+H: 234, observed: 234.

Example 37

5-Methoxy-6-chloro-1,2,3,3a,8,8a-hexahydroindeno[1,2-c]pyrrole

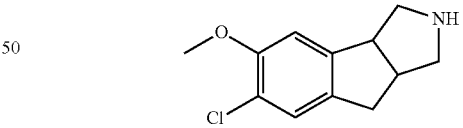

Step A. 2-Benzyl-5-methoxy-1,2,3,3a,8,8a-hexahydro-2-aza-cyclopenta[a]inden-8-ol. (Scheme 1)

NaBH$_4$ (0.27 g, 6.8 mmol) was added to a solution of 2-benzyl-5-methoxy-2,3,3a,8a-tetrahydro-1H-2-aza-cyclopenta[a]inden-8-one (from Example 1, Step C) (1.0 g, 3.4 mmol) in MeOH (17 mL), and stirred for 2 hours at room temperature. The reaction solution was concentrated via rotary evaporation and the residue dissolved in EtOAc. The organic solution was washed with a saturated aqueous NaHCO$_3$ solution and brine, dried over MgSO$_4$, and concentrated. The crude product was obtained without further purification. MS calculated for $C_{19}H_{21}NO_2$+H: 296, observed: 296.

Step B. 2-Benzyl-5-methoxy-1,2,3,3a,8,8a-hexahydroindeno[1,2-c]pyrrole.

InCl$_3$ (0.38 g, 1.7 mmol) and chlorodiphenylsilane (1.3 mL, 6.8 mmol) were added to a solution of 2-benzyl-5-methoxy-1,2,3,3a,8,8a-hexahydro-2-aza-cyclopenta[a]inden-8-ol (3.4 mmol) in DCE (17 mL), and stirred overnight at 60° C. The reaction mixture was washed with H$_2$O, a saturated aqueous NaHCO$_3$ solution and brine. The organic extracts were dried over MgSO$_4$ and concentrated. The crude product was obtained without further purification. MS calculated for C$_{19}$H$_{21}$NO+H: 280, observed: 280.

Step C. 5-Methoxy-1,2,3,3a,8,8a-hexahydroindeno[1,2-c]pyrrole.

The subtitle compound was prepared by the method of Example 1, Step E utilizing 2-benzyl-5-methoxy-1,2,3,3a,8,8a-hexahydroindeno[1,2-c]pyrrole (3.4 mmol). The crude product was obtained without further purification. MS calculated for C$_{12}$H$_{15}$NO+H: 190, observed: 190.

Step D. N-Ethylcarbamate-5-methoxy-1,2,3,3a,8,8a-hexahydroindeno[1,2-c]pyrrole.

The subtitle compound was prepared by the method of Example 2, Step A utilizing 5-methoxy-1,2,3,3a,8,8a-hexahydroindeno[1,2-c]pyrrole (3.4 mmol). The crude product was purified by column chromatography (SiO$_2$) using a 0-50% EtOAc-hexanes gradient to afford the subtitle compound. MS calculated for C$_{15}$H$_{19}$NO$_3$+H: 262, observed: 262.

Step E. N-Ethylcarbamate-5-methoxy-6-chloro-1,2,3,3a,8,8a-hexahydroindeno[1,2-c]pyrrole.

The subtitle compound was prepared by the method of Example 3, Step A utilizing N-ethylcarbamate-5-methoxy-1,2,3,3a,8,8a-hexahydroindeno[1,2-c]pyrrole (0.19 mmol). The crude product was obtained without further purification. MS calculated for C$_{15}$H$_{18}$ClNO$_3$+H: 296, observed: 296.

Step F. 5-Methoxy-6-chloro-1,2,3,3a,8,8a-hexahydroindeno[1,2-c]pyrrole.

The title compound was prepared by the method of Example 3, Step B utilizing N-ethylcarbamate-5-methoxy-6-chloro-8-1,2,3,3a,8,8a-hexahydroindeno[1,2-c]pyrrole (0.19 mmol). The crude product was purified by reverse-phase liquid chromatography to afford the title compound. $^1$H NMR (d$_6$-DMSO 300 MHz) * 7.17 (s, 1H), 6.97 (s, 1H), 3.81 (s, 3H), 3.62 (m, 1H), 3.00 (m, 5H), 2.60 (m, 2H) ppm. MS calculated for C$_{12}$H$_{14}$ClNO+H: 224, observed: 224.

Example 38

4,6-Dichloro-5-Methoxy-8-methyl-1,2,3,3a,8,8a-hexahydroindeno[1,2-c]pyrrole

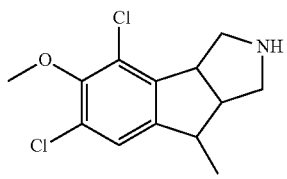 [SMILES: COc1c(Cl)cc2c(c1Cl)C1CNCC1C2C]

Step A. N-Ethylcarbamate-4,6-dichloro-5-methoxy-8-methyl-1,2,3,3a,8,8a-hexahydroindeno[1,2-c]pyrrole. (Scheme 1)

NCS (63 mg, 0.47 mmol) and acetic acid (1 mL) were added to a solution of N-ethylcarbamate-5-methoxy-8-methyl-1,2,3,3a,8,8a-hexahydroindeno[1,2-c]pyrrole (from Example 2, Step A) (43 mg, 0.16 mmol) in DCE (1 mL), and the reaction solution was stirred for 3 hours at 70° C. The reaction was quenched with H$_2$O and the solution filtered through an Extrelut column. The column was washed with CH$_2$Cl$_2$, and the filtrate was concentrated. The subtitle compound was obtained without further purification. MS calculated for C$_{16}$H$_{19}$Cl$_2$NO$_3$+H: 344, observed: 344.

Step B. 4,6-Dichloro-5-methoxy-8-methyl-1,2,3,3a,8,8a-hexahydroindeno[1,2-c]pyrrole.

The title compound was prepared by the method of Example 3, Step B utilizing N-Ethylcarbamate-4,6-dichloro-5-methoxy-8-methyl-1,2,3,3a,8,8a-hexahydroindeno[1,2-c]pyrrole (0.16 mmol). The crude product was purified by reverse-phase liquid chromatography to afford the title compound. $^1$H NMR (d$_6$-DMSO 300 MHz) * 7.28 (s, 1H), 3.78 (s, 3H), 3.71 (m, 1H), 3.29 (m, 2H), 2.84 (m, 3H), 2.60 (m, 1H), 1.21 (d, 3H) ppm. MS calculated for C$_{13}$H$_{16}$Cl$_2$NO+H: 272, observed: 272.

Example 39

5-Cyclopropylmethoxy-6-chloro-8-methyl-1,2,3,3a,8,8a-hexahydroindeno[1,2-c]pyrrole

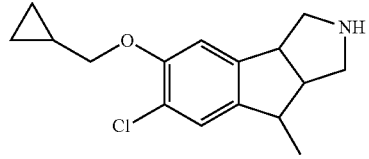 [SMILES: CC1c2cc(Cl)c(OCC3CC3)cc2C2CNCC12]

Step A. N-Ethylcarbamate-5-hydroxy-8-methyl-1,2,3,3a,8,8a-hexahydroindeno[1,2-c]pyrrole. (Scheme 1)

BBr$_3$ (1.1 mL, 1.0 M in dichloromethane) was added to a solution of N-ethylcarbamate-5-methoxy-8-methyl-1,2,3,3a,8,8a-hexahydroindeno[1,2-c]pyrrole (from Example 2, step A) (0.31 g, 1.1 mmol) in CH$_2$Cl$_2$ (10 mL) at 0° C., and stirred overnight. The excess BBr$_3$ was quenched with the dropwise addition of water (2 mL), and washed with saturated aqueous NaHCO$_3$ (10 mL) and brine (10 mL). The organic extract was dried over MgSO$_4$ and concentrated. The subtitle compound was obtained without further purification. MS calculated for C$_{15}$H$_{19}$NO$_3$+H: 262, observed: 262.

Step B. N-Ethylcarbamate-5-cyclopropylmethoxy-8-methyl-1,2,3,3a,8,8a-hexahydroindeno[1,2-c]pyrrole.

(Bromomethyl)cyclopropane (13 mg, 0.09 mmol) and K$_2$CO$_3$ (24 mg, 0.17 mmol) were added to a solution of N-ethylcarbamate-5-hydroxy-8-methyl-1,2,3,3a,8,8a-hexahydroindeno[1,2-c]pyrrole (23 mg, 0.09 mmol) in CH$_3$CN, and stirred overnight at 80° C. The reaction mixture was diluted with H$_2$O and CH$_2$Cl$_2$, and filtered through an Extrelut column. The column was washed with CH$_2$Cl$_2$, and the filtrate was concentrated. The subtitle compound was obtained without further purification. MS calculated for C$_{19}$H$_{25}$NO$_3$+H: 316, observed: 316.

Step C. N-Ethylcarbamate-5-cyclopropylmethoxy-6-chloro-8-methyl-1,2,3,3a,8,8a-hexahydroindeno[1,2-c]pyrrole.

NCS (38 mg, 0.28 mmol) and acetic acid (1 mL) were added to a solution of N-ethylcarbamate-5-cyclopropylmethoxy-8-methyl-1,2,3,3a,8,8a-hexahydroindeno[1,2-c]pyrrole (89 mg, 0.28 mmol) in DCE (2 mL), and the reaction solution was stirred for 3 hours at 70° C. The reaction was quenched with H$_2$O and the solution filtered through an Extrelut column. The column was washed with CH$_2$Cl$_2$, and the filtrate was concentrated. The subtitle compound was obtained without further purification. MS calculated for $C_{19}H_{24}ClNO_3+H$: 350, observed: 350.

Step D. 5-Cyclopropylmethoxy-6-chloro-8-methyl-1,2,3,3a,8,8a-hexahydroindeno[1,2-c]pyrrole.

The title compound was prepared by the method of Example 3, Step B utilizing N-ethylcarbamate-5-cyclopropylmethoxy-6-chloro-8-methyl-1,2,3,3a,8,8a-hexahydroindeno[1,2-c]pyrrole (0.32 mmol). The crude product was purified by reverse-phase liquid chromatography to afford the title compound. $^1$H NMR (d$_6$-DMSO 300 MHz) * 7.14 (s, 1H), 6.9 (s, 1H), 3.88 (d, 2H), 3.24 (m, 3H), 2.84 (m, 3H), 2.45 (m, 1H), 1.21 (m, 4H), 0.58 (d, 2H), 0.32 (d, 2H) ppm. MS calculated for $C_{16}H_{20}ClNO+H$: 278, observed: 278.

Example 40

5-Trifluoromethoxy-8-methyl-1,2,3,3a,8,8a-hexahydroindeno[1,2-c]pyrrole

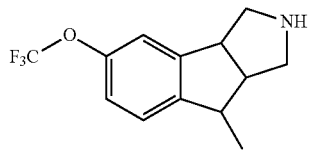 [SMILES: CC1c2ccc(OC(F)(F)F)cc2C2CNCC12]

Step A. 3-(3-Trifluoromethoxy-phenyl)-acrylic acid ethyl ester. (Scheme 3)

The subtitle compound was prepared by the method of Example 13, Step A utilizing 3-(trifluoromethyl)benzaldehyde (12.5 mmol). The crude product was obtained without further purification. MS calculated for $C_{12}H_{11}F_3O_3+H$: 261, observed: 261.

Step B. 1-Benzyl-4-(3-trifluoromethoxy-phenyl)-pyrrolidine-3-carboxylic acid ethyl ester.

The subtitle compound was prepared by the method of Example 1, Step C utilizing 3-(3-trifluoromethoxy-phenyl)-acrylic acid ethyl ester (12.5.0 mmol). The crude product was purified by column chromatography (SiO$_2$) using a 10-50% EtOAc-hexanes gradient to afford 3.5 g (72%—two steps) of the subtitle compound. MS calculated for $C_{21}H_{22}F_3NO_3+H$: 394, observed: 394.

Step C. 1-Benzyl-4-(3-trifluoromethoxy-phenyl)-pyrrolidine-3-carboxylic acid.

The subtitle compound was prepared by the method of Example 13, Step C utilizing 1-benzyl-4-(3-trifluoromethoxy-phenyl)-pyrrolidine-3-carboxylic acid ethyl ester (8.9 mmol). The crude product was obtained without further purification. MS calculated for $C_{19}H_{18}F_3NO_3+H$: 366, observed: 366.

Step D. 2-Benzyl-5-trifluoromethoxy-2,3,3a,8a-tetrahydro-1H-2-aza-cyclopenta[a]inden-8-one.

The subtitle compound was prepared by the method of Example 13, Step D utilizing 1-benzyl-4-(3-trifluoromethoxy-phenyl)-pyrrolidine-3-carboxylic acid (8.9 mmol). The crude product was purified by column chromatography (SiO$_2$) using a 15-60% EtOAc-hexanes gradient to afford 0.50 g (16%—two steps) of the subtitle compound. MS calculated for $C_{19}H_{16}F_3NO_2+H$: 348, observed: 348.

Step E. 2-Benzyl-5-trifluoromethoxy-8-methylene-1,2,3,3a,8,8a-hexahydro-2-aza-cyclopenta[a]indene.

The subtitle compound was prepared by the method of Example 1, Step D utilizing 2-benzyl-5-trifluoromethoxy-2,3,3a,8a-tetrahydro-1H-2-aza-cyclopenta[a]inden-8-one (0.5 mmol). The crude product was purified by silica plug eluting with EtOAc-hexanes (3/1, v/v) to afford the subtitled compound. MS calculated for $C_{20}H_{18}F_3NO+H$: 346, observed: 346.

Step F. 5-Trifluoromethoxy-8-methyl-1,2,3,3a,8,8a-hexahydroindeno[1,2-c]pyrrole.

The title compound was prepared by the method of Example 1, Step E utilizing 2-benzyl-5-trifluoromethoxy-8-methylene-1,2,3,3a,8,8a-hexahydro-2-aza-cyclopenta[a]indene (0.5 mmol). An aliquot of the crude product was purified by reverse-phase liquid chromatography to afford the title compound. $^1$H NMR (d$_6$-DMSO 300 MHz) * 7.19 (m, 3H), 3.65 (m, 1H), 3.28 (m, 2H), 2.83 (m, 3H), 2.45 (m, 1H), 1.25 (d, 3H) ppm. MS calculated for $C_{13}H_{14}F_3NO+H$: 258, observed: 258.

Example 41

4,5-Dichloro-8-methyl-1,2,3,3a,8,8a-hexahydroindeno[1,2-c]pyrrole

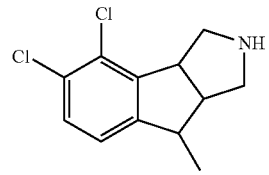

Step A. 3-(2,3-Dichloro-phenyl)-acrylic acid ethyl ester.

The subtitle compound was prepared by the method of Example 13, Step A utilizing 3,4-dichlorobenzaldehyde (29.0 mmol). The crude product was obtained without further purification. MS calculated for $C_{11}H_{10}Cl_2O_2+H$: 245, observed: 245.

Step B. 1-Benzyl-4-(2,3-dichloro-phenyl)-pyrrolidine-3-carboxylic acid ethyl ester.

The subtitle compound was prepared by the method of Example 1, Step C utilizing 3-(2,3-dichloro-phenyl)-acrylic acid ethyl ester (29.0 mmol). The crude product was purified by column chromatography (SiO$_2$) using a 0-70% EtOAc-hexanes gradient to afford 5.3 g (49%—two steps) of the subtitle compound. MS calculated for $C_{20}H_{22}Cl_2NO_2+H$: 378, observed: 378.

Step C. 1-Benzyl-4-(2,3-dichloro-phenyl)-pyrrolidine-3-carboxylic acid.

The subtitle compound was prepared by the method of Example 13, Step C utilizing 1-benzyl-4-(2,3-dichloro-phenyl)-pyrrolidine-3-carboxylic acid ethyl ester (14.0 mmol). The crude product was obtained without further purification. MS calculated for $C_{18}H_{18}Cl_2NO_2+H$: 350, observed: 350.

Step D. 2-Benzyl-4,5-dichloro-2,3,3a,8a-tetrahydro-1H-2-aza-cyclopenta[a]inden-8-one.

The subtitle compound was prepared by the method of Example 13, Step D utilizing 1-benzyl-4-(2,3-dichloro-phenyl)-pyrrolidine-3-carboxylic acid (14.0 mmol). The crude product was purified by column chromatography (SiO$_2$) using a 0-50% EtOAc-hexanes gradient to afford the subtitle compound. MS calculated for $C_{18}H_{16}Cl_2NO+H$: 332, observed: 332.

Step E. 2-Benzyl-4,5-dichloro-8-methylene-1,2,3,3a,8,8a-hexahydro-2-aza-cyclopenta[a]indene.

The subtitle compound was prepared by the method of Example 1, Step D utilizing 2-benzyl-4,5-dichloro-2,3,3a,8a-tetrahydro-1H-2-aza-cyclopenta[a]inden-8-one (14.0 mmol). The crude product was purified by silica plug eluting with EtOAc-hexanes (3/1, v/v) to afford 1.7 g (35%—three steps) of the subtitle compound. MS calculated for $C_{19}H_{18}Cl_2N+H$: 330, observed: 330.

Step F. 4,5-Dichloro-8-methylene-1,2,3,3a,8,8a-hexahydro-2-aza-cyclopenta[a]indene.

The subtitle compound was prepared by the method of Example 20, Step F utilizing 2-benzyl-4,5-dichloro-8-methylene-1,2,3,3a,8,8a-hexahydro-2-aza-cyclopenta[a]indene (4.9 mmol). The crude product was obtained without further purification. MS calculated for $C_{12}H_{12}Cl_2N+H$: 240, observed: 240.

Step G. N-Ethyl carbamate-4,5-dichloro-8-methylene-1,2,3,3a,8,8a-hexahydro-2-aza-cyclopenta[a]indene.

The subtitle compound was prepared by the method of Example 2, Step A utilizing 4,5-dichloro-8-methylene-1,2,3,3a,8,8a-hexahydro-2-aza-cyclopenta[a]indene (4.9 mmol). The crude product was purified by column chromatography (SiO$_2$) using a 0-60% EtOAc-hexanes gradient to afford 0.32 g (21%—two steps) of the subtitle compound. MS calculated for $C_{15}H_{15}Cl_2NO_2+H$: 312, observed: 312.

Step H. N-Ethyl carbamate-4,5-dichloro-8-methyl-1,2,3,3a,8,8a-hexahydro-2-aza-cyclopenta[a]indene.

The subtitle compound was prepared by the method of Example 20, Step H utilizing N-ethyl carbamate-4,5-dichloro-8-methylene-1,2,3,3a,8,8a-hexahydro-2-aza-cyclopenta[a]indene (1.0 mmol). The crude product was purified by column chromatography (SiO$_2$) using a 0-60% EtOAc-hexanes gradient to afford 0.10 g (32%) of the subtitle compound. MS calculated for $C_{15}H_{17}Cl_2NO_2+H$: 314, observed: 314.

Step I. 4,5-Dichloro-8-methyl-1,2,3,3a,8,8a-hexahydroindeno[1,2-c]pyrrole.

The title compound was prepared by the method of Example 3, Step B utilizing N-ethyl carbamate-4,5-dichloro-8-methyl-1,2,3,3a,8,8a-hexahydro-2-aza-cyclopenta[a]indene (0.06 mmol). An aliquot of the crude product was purified by reverse-phase liquid chromatography to afford the title compound. $^1$H NMR (d$_6$-DMSO 300 MHz) * 7.46 (d, 1H), 7.16 (d, 1H), 3.76 (m, 1H), 3.36 (m, 2H), 2.85 (m, 3H), 2.45 (m, 1H), 1.23 (d, 3H) ppm. MS calculated for $C_{12}H_{13}Cl_2N+H$: 242, observed: 242.

Example 42

6-Chloro-7-fluoro-8-methyl-1,2,3,3a,8,8a-hexahydroindeno[1,2-c]pyrrole

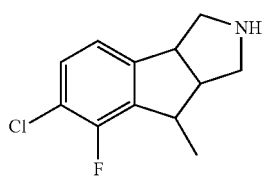

Step A. 3-(3-Fluoro-4-chloro-phenyl)-acrylic acid methyl ester. (Scheme 3)

The subtitle compound was prepared by the method of Example 13, Step A utilizing 3,4-dichlorobenzaldehyde (34.0 mmol). The crude product was obtained without further purification. MS calculated for $C_{10}H_8ClFO_2+H$: 215, observed: 215.

Step B. 1-Benzyl-4-(3-fluoro-4-chloro-phenyl)-pyrrolidine-3-carboxylic acid methyl ester.

The subtitle compound was prepared by the method of Example 1, Step C utilizing 3-(3-fluoro-4-chloro-phenyl)-acrylic acid methyl ester (34.0 mmol). The crude product was purified by column chromatography (SiO$_2$) using a 0-45% EtOAc-hexanes gradient to afford 6.3 g (53%—two steps) of the subtitle compound. MS calculated for $C_{19}H_{19}ClFNO_2+H$: 348, observed: 348.

Step C. 1-Benzyl-4-(3-fluoro-4-chloro-phenyl)-pyrrolidine-3-carboxylic acid.

The subtitle compound was prepared by the method of Example 13, Step C utilizing 1-benzyl-4-(2,3-dichloro-phenyl)-pyrrolidine-3-carboxylic acid ethyl ester (18.1 mmol). The crude product was obtained without further purification. MS calculated for $C_{18}H_{17}ClFNO_2+H$: 334, observed: 334.

Step D. 2-Benzyl-6-chloro-7-fluoro-2,3,3a,8a-tetrahydro-1H-2-aza-cyclopenta[a]inden-8-one.

The subtitle compound was prepared by the method of Example 13, Step D utilizing 1-benzyl-4-(3-fluoro-4-chloro-phenyl)-pyrrolidine-3-carboxylic acid (18.1 mmol). The crude product was purified by column chromatography (SiO$_2$) using a 0-50% EtOAc-hexanes gradient to afford the subtitle compound. MS calculated for $C_{18}H_{15}ClFNO+H$: 316, observed: 316.

Step E. 6-Chloro-7-fluoro-2,3,3a,8a-tetrahydro-1H-2-aza-cyclopenta[a]inden-8-one.

The subtitle compound was prepared by the method of Example 20, Step F utilizing 2-benzyl-6-chloro-7-fluoro-2,3,3a,8a-tetrahydro-1H-2-aza-cyclopenta[a]inden-8-one (2.1 mmol). The crude product was obtained without further purification. MS calculated for $C_{11}H_9ClFNO+H$: 226, observed: 226.

Step F. N-Ethyl carbamate-6-chloro-7-fluoro-2,3,3a,8a-tetrahydro-1H-2-aza-cyclopenta[a]inden-8-one.

The subtitle compound was prepared by the method of Example 2, Step A utilizing 6-chloro-7-fluoro-2,3,3a,8a-tetrahydro-1H-2-aza-cyclopenta[a]inden-8-one (2.2 mmol). The crude product was purified by column chromatography (SiO$_2$) using a 0-55 EtOAc-hexanes gradient to afford the subtitle compound in quantitative yield. MS calculated for $C_{14}H_{13}ClFNO_3+H$: 298, observed: 298.

Step G. N-Ethyl carbamate-6-chloro-7-fluoro-8-methylene-1,2,3,3a,8,8a-hexahydro-2-aza-cyclopenta[a]indene.

The subtitle compound was prepared by the method of Example 2, Step A utilizing 4,5-dichloro-8-methylene-1,2,3,3a,8,8a-hexahydro-2-aza-cyclopenta[a]indene (1.5 mmol). The crude product was purified by column chromatography (SiO$_2$) using a 10-55% EtOAc-hexanes gradient to afford 0.43 g (66%—two steps) of the subtitle compound in quantitative yield. MS calculated for $C_{15}H_{15}ClFNO_2+H$: 296, observed: 296.

Step H. N-Ethyl carbamate-6-chloro-7-fluoro-8-methyl-1,2,3,3a,8,8a-hexahydro-2-aza-cyclopenta[a]indene.

The subtitle compound was prepared by the method of Example 20, Step H utilizing N-ethyl carbamate-6-chloro-7-fluoro-8-methylene-1,2,3,3a,8,8a-hexahydro-2-aza-cyclopenta[a]indene (0.2 mmol). The crude product was purified by column chromatography (SiO$_2$) using a 0-60% EtOAc-hexanes gradient to afford the subtitle compound in quantitative yield. MS calculated for $C_{15}H_{17}ClFNO_2+H$: 298, observed: 298.

Step I. 6-Chloro-7-fluoro-8-methyl-1,2,3,3a,8,8a-hexahydroindeno[1,2-c]pyrrole.

The title compound was prepared by the method of Example 3, Step B utilizing N-ethyl carbamate-6-chloro-7-fluoro-8-methyl-1,2,3,3a,8,8a-hexahydro-2-aza-cyclopenta[a]indene (0.06 mmol). An aliquot of the crude product was purified by reverse-phase liquid chromatography to afford the title compound. $^1$H NMR (d$_6$-DMSO 300 MHz) * 7.30 (d, 1H), 7.19 (d, 1H), 3.92 (m, 1H), 3.65 (m, 1H), 3.44 (m, 2H), 3.30 (m, 2H), 2.88 (m, 1H), 1.33 (d, 3H) ppm. MS calculated for C$_{12}$H$_{13}$ClFN+H: 226, observed: 226.

Example 43

5-Benzyloxy-8-methyl-1,2,3,3a,8,8a-hexahydroindeno[1,2-c]pyrrole

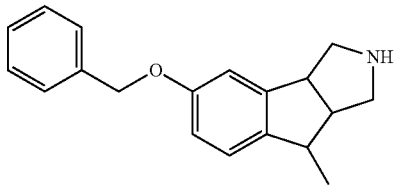 [SMILES: CC1c2ccc(OCc3ccccc3)cc2C2CNCC12]

Step A. N-Ethylcarbamate-5-hydroxy-8-methyl-1,2,3,3a,8,8a-hexahydroindeno[1,2-c]pyrrole. (Scheme 1)

BBr$_3$ in CH$_2$Cl$_2$ (1.1 mL, 1.1 mmol, 1 M) was added to a solution of N-Ethylcarbamate-5-methoxy-8-methyl-1,2,3,3a,8,8a-hexahydroindeno[1,2-c]pyrrole (from Example 2, Step A) (100 mg, 0.36 mmol) at 0° C. The reaction mixture was stirred overnight from 0° C. to room temperature and quenched with H$_2$O. The solution was filtered through an Extrelut column, the column was washed with CH$_2$Cl$_2$, and the filtrate was concentrated. The crude product was obtained without further purification. MS calculated for C$_{15}$H$_{19}$NO$_3$+H: 262, observed: 262.

Step B. N-Ethylcarbamate-5-benzyloxy-8-methyl-1,2,3,3a,8,8a-hexahydroindeno[1,2-c]pyrrole.

Benzyl bromide (15 µL, 0.12 mmol) and K$_2$CO$_3$ (70 mg, 0.5 mmol) were added to a solution of N-ethylcarbamate-5-hydroxy-8-methyl-1,2,3,3a,8,8a-hexahydro indeno[1,2-c]pyrrole (26 mg, 0.1 mmol) in CH$_3$CN (2 mL). The resulting mixture was stirred overnight at 80° C. The reaction was cooled to room temperature, concentrated by rotary evaporation and taken up in H$_2$O (2.5 mL). The product was extracted with ethyl acetate (3×5 mL). The combined organic extracts were dried over MgSO$_4$ and concentrated to afford the subtitle compound, which was used without further purification. MS calculated for C$_{22}$H$_{25}$NO$_3$+H: 352, observed: 352.

Step C. 5-Benzyloxy-8-methyl-1,2,3,3a,8,8a-hexahydroindeno[1,2-c]pyrrole.

The title compound was prepared by the method of Example 3, Step B utilizing N-ethylcarbamate-5-benzyloxy-8-methyl-1,2,3,3a,8,8a-hexahydroindeno[1,2-c]pyrrole (0.1 mmol). The crude product was purified by reverse-phase liquid chromatography to afford the title compound. MS calculated for C$_{19}$H$_{21}$NO+H: 280, observed: 280.

Example 44

5-(2-Fluorobenzyloxy)-8-methyl-1,2,3,3a,8,8a-hexahydroindeno[1,2-c]pyrrole

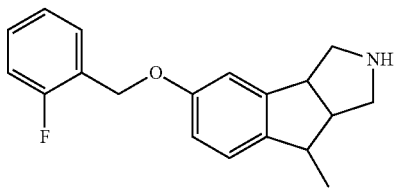 [SMILES: CC1c2ccc(OCc3ccccc3F)cc2C2CNCC12]

Step A. N-Ethylcarbamate-5-(2-fluorobenzyloxy)-8-methyl-1,2,3,3a,8,8a-hexahydroindeno[1,2-c]pyrrole. (Scheme 1)

The subtitle compound was prepared by the method of Example 43, Step B utilizing N-ethylcarbamate-5-hydroxy-8-methyl-1,2,3,3a,8,8a-hexahydroindeno[1,2-c]pyrrole (from Example 43, Step A) (0.1 mmol) and 2-fluorobenzyl bromide. The crude product was obtained without further purification. MS calculated for C$_{22}$H$_{24}$FNO$_3$+H: 370, observed: 370.

Step B. 5-(2-Fluorobenzyloxy)-8-methyl-1,2,3,3a,8,8a-hexahydroindeno[1,2-c]pyrrole.

The title compound was prepared by the method of Example 3, Step B utilizing N-ethylcarbamate-5-(2-fluorobenzyloxy)-8-methyl-1,2,3,3a,8,8a-hexahydroindeno[1,2-c]pyrrole (0.1 mmol). The crude product was purified by reverse-phase liquid chromatography to afford the title compound. MS calculated for C$_{19}$H$_{20}$FNO+H: 298, observed: 298.

Example 45

5-(3-Fluorobenzyloxy)-8-methyl-1,2,3,3a,8,8a-hexahydroindeno[1,2-c]pyrrole

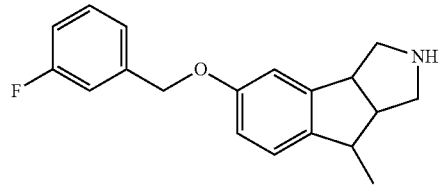 [SMILES: CC1c2ccc(OCc3cccc(F)c3)cc2C2CNCC12]

Step A. N-Ethylcarbamate-5-(3-fluorobenzyloxy)-8-methyl-1,2,3,3a,8,8a-hexahydroindeno[1,2-c]pyrrole. (Scheme 1)

The subtitle compound was prepared by the method of Example 43, Step B utilizing N-ethylcarbamate-5-hydroxy-8-methyl-1,2,3,3a,8,8a-hexahydroindeno[1,2-c]pyrrole (from Example 43, Step A) (0.1 mmol) and 3-fluorobenzyl bromide. The crude product was obtained without further purification. MS calculated for C$_{22}$H$_{24}$FNO$_3$+H: 370, observed: 370.

Step B. 5-(3-Fluorobenzyloxy)-8-methyl-1,2,3,3a,8,8a-hexahydroindeno[1,2-c]pyrrole.

The title compound was prepared by the method of Example 3, Step B utilizing N-ethylcarbamate-5-(3-fluorobenzyloxy)-8-methyl-1,2,3,3a,8,8a-hexahydroindeno[1,2-c]pyrrole (0.1 mmol). The crude product was purified by reverse-phase liquid chromatography to afford the title compound. MS calculated for C$_{19}$H$_{20}$FNO+H: 298, observed: 298.

Example 46

5-(4-Fluorobenzyloxy)-8-methyl-1,2,3,3a,8,8a-hexahydroindeno[1,2-c]pyrrole

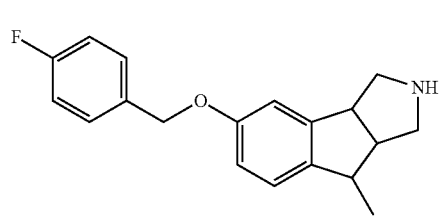 [SMILES: CC1c2ccc(OCc3ccc(F)cc3)cc2C2CNCC12]

Step A. N-Ethylcarbamate-5-(4-fluorobenzyloxy)-8-methyl-1,2,3,3a,8,8a-hexahydroindeno[1,2-c]pyrrole. (Scheme 1)

The subtitle compound was prepared by the method of Example 43, Step B utilizing N-ethylcarbamate-5-hydroxy-8-methyl-1,2,3,3a,8,8a-hexahydroindeno[1,2-c]pyrrole (from Example 43, Step A) (0.1 mmol) and 4-fluorobenzyl bromide. The crude product was obtained without further purification. MS calculated for $C_{22}H_{24}FNO_3+H$: 370, observed: 370.

Step B. 5-(4-Fluorobenzyloxy)-8-methyl-1,2,3,3a,8,8a-hexahydroindeno[1,2-c]pyrrole.

The title compound was prepared by the method of Example 3, Step B utilizing N-ethylcarbamate-5-(4-fluorobenzyloxy)-8-methyl-1,2,3,3a,8,8a-hexahydroindeno[1,2-c]pyrrole (0.1 mmol). The crude product was purified by reverse-phase liquid chromatography to afford the title compound. MS calculated for $C_{19}H_{20}FNO+H$: 298, observed: 298.

Example 47

5-(2,6-Difluorophenyl)-8-methyl-1,2,3,3a,8,8a-hexahydroindeno[1,2-c]pyrrole

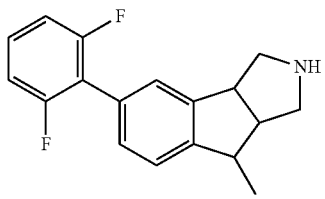 [SMILES: CC1c2ccc(-c3c(F)cccc3F)cc2C2CNCC12]

Step A. N-Ethylcarbamate-5-triflate-8-methyl-1,2,3,3a,8,8a-hexahydroindeno[1,2-c]pyrrole. (Scheme 1)

Pyridine (0.9 mL, 1.08 mmol) and trifluoromethanesulfonic anhydride (0.12 mL, 0.72 mmol) were added to a solution of N-ethylcarbamate-5-hydroxy-8-methyl-1,2,3,3a,8,8a-hexahydroindeno[1,2-c]pyrrole (from Example 43, Step A) (94 mg, 0.36 mmol) in $CH_2Cl_2$ (4 mL) at 0° C. The reaction solution was stirred for 2 hours from 0° C. to room temperature, then diluted with $CH_2Cl_2$. The crude product was washed with aqueous HCl (1 M), saturated aqueous $NaHCO_3$, and brine. The organic extracts were dried over $MgSO_4$ and concentrated to afford 52 mg (58%) of the subtitle compound. MS calculated for $C_{16}H_{18}F_3NO_5S+H$: 394, observed: 394.

Step B. N-Ethylcarbamate-5-(2,6-difluorophenyl)-8-methyl-1,2,3,3a,8,8a-hexahydroindeno[1,2-c]pyrrole.

2,6-Difluorophenylboronic acid (41 mg, 0.26 mmol), Pd(dppf) (5 mg), and $Et_3N$ (0.2 mL) were added to a solution of N-ethylcarbamate-5-triflate-8-methyl-1,2,3,3a,8,8a-hexahydroindeno[1,2-c]pyrrole (52 mg, 0.13 mmol) in DME (2.6 mL), and stirred overnight at 90° C. The solution was cooled to room temperature, partitioned between $CH_2Cl_2$ and $H_2O$, and filtered through an Extrelut column. The column was washed with $CH_2Cl_2$, and the filtrate was concentrated. The crude product was obtained without further purification. MS calculated for $C_{21}H_{21}F_2NO_2+H$: 358, observed: 358.

Step C. 5-(2,6-Difluorophenyl)-8-methyl-1,2,3,3a,8,8a-hexahydroindeno[1,2-c]pyrrole.

The title compound was prepared by the method of Example 2, Step B utilizing N-ethylcarbamate-5-(2,6-difluorophenyl)-8-methyl-1,2,3,3a,8,8a-hexahydroindeno[1,2-c]pyrrole (0.1 mmol). The crude product was purified by reverse-phase liquid chromatography to afford the title compound. MS calculated for $C_{18}H_{17}F_2N+H$: 286, observed: 286.

Example 48

5-Methoxy-8-ethyl-1,2,3,3a,8,8a-hexahydroindeno[1,2-c]pyrrole

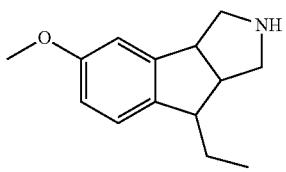 [SMILES: CCC1c2ccc(OC)cc2C2CNCC12]

Step A. 2-Benzyl-5-methoxy-8-ethylene-1,2,3,3a,8,8a-hexahydroindeno[1,2-c]pyrrole. (Scheme 1)

Ethyltriphenylphosphonium bromide (0.6 g, 1.6 mmol) and potassium tert-butoxide (0.18 g, 1.6 mmol) were added to a solution of 2-benzyl-5-methoxy-2,3,3a,8a-tetrahydro-1H-2-aza-cyclopenta[a]inden-8-one (from Example 1, Step C) (0.32 g, 1.1 mmol) in anhydrous ether (2.2 mL). The reaction mixture was stirred for 1 hour at room temperature then filtered through celite. The celite was washed with ether (10 mL), and the filtrate was concentrated. The crude product was purified by column chromatography ($SiO_2$) using a 0-35% EtOAc-hexanes gradient to afford the subtitle compound in quantitative yield. MS calculated for $C_{21}H_{23}NO+H$: 306, observed: 306.

Step B. 5-Methoxy-8-ethyl-1,2,3,3a,8,8a-hexahydroindeno[1,2-c]pyrrole.

Ammonium formate (0.3 g) and palladium (10 wt. % on activated carbon, 0.3 g) were added to a solution of 2-benzyl-5-methoxy-8-ethylene-1,2,3,3a,8,8a-hexahydroindeno[1,2-c]pyrrole (0.34 g, 1.1 mmol) in MeOH (5 mL). The reaction mixture was stirred for 4 hours at 60° C. and then filtered through celite. The celite was washed with MeOH (20 mL) and the filtrate was concentrated. The crude product was purified by reverse-phase liquid chromatography to afford the title compound. $^1H$ NMR ($d_6$-DMSO 300 MHz) * 7.05 (d, 1H), 6.75 (m, 2H), 3.69 (s, 3H), 3.58 (m, 1H), 3.28 (m, 1H), 3.05 (m, 1H), 2.90 (m, 3H), 2.31 (m, 1H), 2.05 (m, 1H), 1.28 (m, 1H), 1.05 (t, 3H) ppm. MS calculated for $C_{14}H_{19}NO+H$: 218, observed: 218.

Example 49

5-Hydroxy-8-ethyl-1,2,3,3a,8,8a-hexahydroindeno[1,2-c]pyrrole

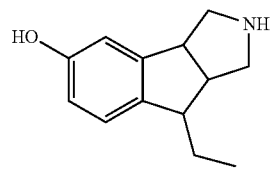

Step A. N-Ethylcarbamate-5-methoxy-8-ethyl-1,2,3,3a,8,8a-hexahydroindeno[1,2-c]pyrrole. (Scheme 1)

Ethyl chloroformate (0.16 mL, 1.65 mmol) was added to a solution of 5-methoxy-8-ethyl-1,2,3,3a,8,8a-hexahydroindeno[1,2-c]pyrrole (from Example 48, Step B) (0.24 g, 1.1 mmol) in CH$_2$Cl$_2$ (6 mL) at 0° C. The resulting solution was stirred overnight at room temperature. The reaction mixture was quenched with aqueous HCl solution (20 mL, 1.0 M) and the product was extracted with EtOAc (3×10 mL). The combined organic extracts were dried over MgSO$_4$ and concentrated. The crude product was purified by column chromatography (SiO$_2$) using a 0-35% EtOAc-hexanes gradient to afford 40 mg (13%) of the subtitle compound. MS calculated for C$_{17}$H$_{23}$NO$_3$+H: 290, observed: 290.

Step B. 5-Hydroxy-8-ethyl-1,2,3,3a,8,8a-hexahydroindeno[1,2-c]pyrrole.

The title compound was prepared by the method of Example 2, Step B utilizing N-ethylcarbamate-5-hydroxy-8-ethyl-1,2,3,3a,8,8a-hexahydroindeno[1,2-c]pyrrole (0.07 mmol). The crude product was purified by reverse-phase liquid chromatography to afford the title compound. $^1$H NMR (d$_6$-DMSO 300 MHz) * 6.98 (d, 1H), 6.59 (m, 2H), 3.68 (m, 1H), 3.44 (m, 1H), 3.05 (m, 4H), 2.45 (m, 1H), 1.98 (m, 1H), 1.25 (m, 1H), 1.05 (t, 3H) ppm. MS calculated for C$_{13}$H$_{17}$NO+H: 204, observed: 204.

Example 50

5,6(2-(3-methyl)furan)-8-methyl-1,2,3,3a,8,8a-hexahydroindeno[1,2-c]pyrrole

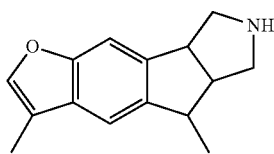 [SMILES: Cc1coc2cc3c(cc12)C(C)C1CNCC31]

Step A. N-Ethylcarbamate-5-methoxy-6-iodo-8-methyl-1,2,3,3a,8,8a-hexahydroindeno[1,2-c]pyrrole. (Scheme 1)

ICl (0.12 g, 0.72 mmol) and CaCO$_3$ (72 mg, 0.72 mmol) were added to a solution of N-ethylcarbamate-5-methoxy-8-methyl-1,2,3,3a,8,8a-hexahydroindeno[1,2-c]pyrrole (from Example 2, Step A) (0.1 g, 0.36 mmol) in MeOH (3.6 mL), and stirred overnight at room temperature. The reaction mixture was filtered through celite, the celite was washed with MeOH, and the filtrate concentrated. The crude material was dissolved in EtOAc, and washed with aqueous sodium bisulfite (5% solution) and brine. The organic extracts were dried over MgSO$_4$ and brine. The crude product was purified via silica plug eluting with Hexanes/EtOAc (3/1, v/v) to afford 0.14 g (97%) of the subtitle compound. MS calculated for C$_{16}$H$_{20}$INO$_3$+H: 402, observed: 402.

Step B. N-Ethylcarbamate-5-hydroxy-6-iodo-8-methyl-1,2,3,3a,8,8a-hexahydroindeno[1,2-c]pyrrole.

BBr$_3$ (0.7 mL, 0.7 mmol, 1 M in CH$_2$Cl$_2$) was added to a solution of N-ethylcarbamate-5-methoxy-6-iodo-8-methyl-1,2,3,3a,8,8a-hexahydroindeno[1,2-c]pyrrole (120 mg, 0.3 mmol) at 0° C. The reaction mixture was stirred overnight from 0° C. to room temperature and quenched with H$_2$O. The solution was filtered through an Extrelut column, the column was washed with CH$_2$Cl$_2$, and the filtrate was concentrated. The crude product was obtained without further purification. MS calculated for C$_{15}$H$_{18}$INO$_3$+H: 388, observed: 388.

Step C. N-Ethylcarbamate-5-allyloxy-6-iodo-8-methyl-1,2,3,3a,8,8a-hexahydroindeno[1,2-c]pyrrole.

Allyl bromide (52 µL, 0.6 mmol) and DBU (65 µL, 0.6 mmol) were added to a solution of N-ethylcarbamate-5-hydroxy-6-iodo-8-ethyl-1,2,3,3a,8,8a-hexahydroindeno[1,2-c]pyrrole (116 mg, 0.3 mmol) in CH$_2$Cl$_2$ (3 mL), and stirred 2 hours at room temperature. The reaction solution was diluted with H$_2$O and filtered through an Extrelut column. The column was washed with CH$_2$Cl$_2$ and the filtrate was concentrated. The crude product was purified via silica plug eluting with Hexanes/EtOAc (3/1, v/v) to afford 50 mg (39%—two steps) of the subtitle compound. MS calculated for C$_{18}$H$_{22}$INO$_3$+H: 428, observed: 428.

Step D. N-Ethylcarbamate-5,6(2-(3-methyl)furan)-8-methyl-1,2,3,3a,8,8a-hexahydroindeno[1,2-c]pyrrole.

KOAc (40 mg, 0.36 mmol), nBu$_4$NBr (50 mg, 0.12 mmol), PPh$_3$ (3 mg, 0.1 mmol), and Pd(OAc)$_2$ (2 mg, 6 µmol) were added to a solution of N-ethylcarbamate-5-allyloxy-6-iodo-8-methyl-1,2,3,3a,8,8a-hexahydroindeno[1,2-c]pyrrole (50 mg, 0.12 mmol) in DMF (1 mL), and stirred overnight at 100 EC. The reaction solution was diluted with H$_2$O and CH$_2$Cl$_2$, and filtered through an Extrelut column. The column was washed with CH$_2$Cl$_2$ and the filtrate was concentrated. The crude product was obtained without further purification. MS calculated for C$_{18}$H$_{21}$NO$_3$+H: 300, observed: 300.

Step E. 5,6(2-(3-Methyl)furan)-8-methyl-1,2,3,3a,8,8a-hexahydroindeno[1,2-c]pyrrole.

The title compound was prepared by the method of Example 2, Step B utilizing N-ethylcarbamate-5,6(2-(3-methyl)furan)-8-methyl-1,2,3,3a,8,8a-hexahydroindeno[1,2-c]pyrrole (0.1 mmol). The crude product was purified by reverse-phase liquid chromatography to afford the title compound. MS calculated for C$_{16}$H$_{170}$NO+H: 228, observed: 228.

Example 51

5-Methoxy-2,3,3a,8a-tetrahydro-1H-2-aza-cyclopenta[a]inden-8-one

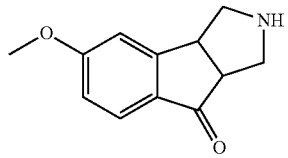

The title compound was prepared by the method of Example 1, Step E utilizing 2-benzyl-5-methoxy-2,3,3a,8a-tetrahydro-1H-2-aza-cyclopenta[a]inden-8-one (from Example 1, Step C) (2.1 mmol). The crude product was purified by reverse-phase liquid chromatography to afford the title compound. $^1$H NMR (d$_6$-DMSO 300 MHz) * 7.48 (d, 1H), 7.12 (d, 1H), 6.95 (dd, 1H), 3.87 (s, 3H), 3.72 (m, 1H), 2.98 (m, 4H), 2.81 (m, 1H) ppm. MS calculated for C$_{12}$H$_{13}$NO$_2$+H: 204, observed: 204.

Example 52

4-Chloro-5-methoxy-2,3,3a,8a-tetrahydro-1H-2-azacyclopenta[a]inden-8-one

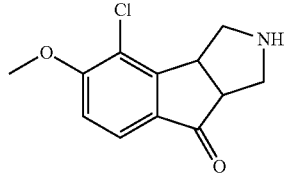 [SMILES: COc1ccc2c(c1Cl)C1CNCC1C2=O]

Step A. N-Ethyl carbamate-5-methoxy-2,3,3a,8a-tetrahydro-1H-2-aza-cyclopenta[a]inden-8-one. (Scheme 1)

Ethyl chloroformate (0.18 mL, 1.9 mmol) and DIEA (1.0 mL, 5.7 mmol) were added to a solution of 5-methoxy-2,3,3a,8a-tetrahydro-1H-2-aza-cyclopenta[a]inden-8-one (from Example 51) (0.38 g, 1.9 mmol) in $CH_2Cl_2$ (10 mL) at 0° C., and stirred overnight at room temperature. The reaction was quenched with aqueous HCl (1 M) and washed with brine. The organic extracts were dried over $MgSO_4$, and concentrated. The crude product was obtained without further purification. MS calculated for $C_{15}H_{17}NO_4$+H: 276, observed: 276.

Step B. N-Ethyl carbamate-4-chloro-5-methoxy-2,3,3a,8a-tetrahydro-1H-2-aza-cyclopenta[a]inden-8-one.

NCS (0.25 g, 1.9 mmol) and acetic acid (10 mL) were added to a solution of ethyl carbamate-5-methoxy-2,3,3a,8a-tetrahydro-1H-2-aza-cyclopenta[a]inden-8-one (0.52 g, 1.9 mmol) in DCE (10 mL), and stirred overnight at 60° C. The reaction was quenched with aqueous HCl (1 M) and washed with brine. The organic extracts were dried over $MgSO_4$, and concentrated. The crude product was purified by column chromatography ($SiO_2$) using a 0-60% EtOAc-hexanes gradient to afford the subtitle compound as a mixture of regioisomers. MS calculated for $C_{15}H_{16}ClNO_4$+H: 310, observed: 310.

Step C. 4-Chloro-5-methoxy-2,3,3a,8a-tetrahydro-1H-2-aza-cyclopenta[a]inden-8-one.

The subtitle compound was prepared by the method of Example 2, Step B utilizing N-ethyl carbamate-4-chloro-5-methoxy-2,3,3a,8a-tetrahydro-1H-2-aza-cyclopenta[a]inden-8-one (0.32 mmol). The crude product was obtained without further purification as a mixture of regioisomers. MS calculated for $C_{12}H_{12}ClNO_2$+H: 238, observed: 238.

Step D. N-tert-butyl carbamate-4-chloro-5-methoxy-2,3,3a,8a-tetrahydro-1H-2-aza-cyclopenta[a]inden-8-one.

The subtitle compound was prepared by the method of Example 20, Step G utilizing 4-chloro-5-methoxy-2,3,3a,8a-tetrahydro-1H-2-aza-cyclopenta[a]inden-8-one (1.02 mmol). The crude product was purified and separated by column chromatography ($SiO_2$) using a 0-60% EtOAc-hexanes gradient to afford the subtitle compound and its regioisomer, N-tert-butyl carbamate-5-methoxy-6-chloro-2,3,3a,8a-tetrahydro-1H-2-aza-cyclopenta[a]inden-8-one. MS calculated for $C_{17}H_{20}ClNO_4$+H: 338, observed: 338.

Step E. 4-Chloro-5-methoxy-2,3,3a,8a-tetrahydro-1H-2-aza-cyclopenta[a]inden-8-one.

The title compound was prepared by the method of Example 20, Step I utilizing N-tert-butyl carbamate-4-chloro-5-methoxy-2,3,3a,8a-tetrahydro-1H-2-aza-cyclopenta[a]inden-8-one (0.10 mmol). The crude product was purified by reverse-phase liquid chromatography to afford the title compound. $^1$H NMR ($d_6$-DMSO 300 MHz) * 7.70 (d, 1H), 7.47 (d, 1H), 4.18 (m, 1H), 4.00 (s, 3H), 3.65 (m, 2H), 3.58 (m, 2H), 3.45 (m, 1H) ppm. MS calculated for $C_{12}H_{12}ClNO_2$+H: 238, observed: 238.

Example 53

5-Methoxy-6-chloro-2,3,3a,8a-tetrahydro-1H-2-aza-cyclopenta[a]inden-8-one

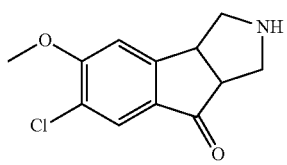 [SMILES: COc1cc2c(cc1Cl)C(=O)C1CNCC21]

The title compound was prepared by the method of Example 20, Step I utilizing N-tert-butyl carbamate-5-methoxy-6-chloro-2,3,3a,8a-tetrahydro-1H-2-aza-cyclopenta[a]inden-8-one (from Example 52, Step D) (0.10 mmol). The crude product was purified by reverse-phase liquid chromatography to afford the title compound. MS calculated for $C_{12}H_{12}ClNO_2$+H: 238, observed: 238.

Example 54

4-Chloro-5-methoxy-2,3,3a,8a-tetrahydro-1H-2-aza-cyclopenta[a]inden-8-ol

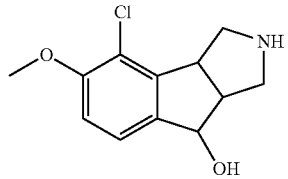 [SMILES: COc1ccc2c(c1Cl)C1CNCC1C2O]

Step A. N-tert-Butyl carbamate-4-chloro-5-methoxy-2,3,3a,8a-tetrahydro-1H-2-aza-cyclopenta[a]inden-8-ol. (Scheme 1)

$NaBH_4$ (4 mg, 0.1 mmol) was added to a solution of N-tert-butyl carbamate-4-chloro-5-methoxy-2,3,3a,8a-tetrahydro-1H-2-aza-cyclopenta[a]inden-8-one (from Example 52, Step D) (20 mg, 0.06 mmol) in MeOH (2 mL), and stirred for 1 hour at room temperature. The reaction was partitioned between $H_2O$ and $CH_2Cl_2$, and filtered through an Extrelut column. The column was washed with $CH_2Cl_2$, and the filtrate was concentrated. The crude product was obtained without further purification as a mixture of diastereomers. MS calculated for $C_{17}H_{22}ClNO_4$+H: 340, observed: 340.

Step B. 4-Chloro-5-methoxy-2,3,3a,8a-tetrahydro-1H-2-aza-cyclopenta[a]inden-8-ol.

The title compound was prepared by the method of Example 20, Step I utilizing N-tert-butyl carbamate-4-chloro-5-methoxy-2,3,3a,8a-tetrahydro-1H-2-aza-cyclopenta[a]inden-8-ol (0.10 mmol). The crude product was purified by reverse-phase liquid chromatography to afford the title compound. MS calculated for $C_{12}H_{12}ClNO_2$+H: 240, observed: 240.

Example 55

5-Methoxy-6-chloro-2,3,3a,8a-tetrahydro-1H-2-aza-cyclopenta[a]inden-8-ol

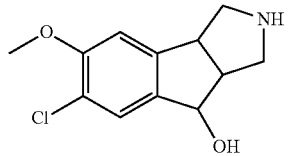 [SMILES: COc1cc2c(cc1Cl)C(O)C1CNCC21]

Step A. N-tert-Butyl carbamate-5-methoxy-6-chloro-2,3,3a,8a-tetrahydro-1H-2-aza-cyclopenta[a]inden-8-ol.

NaBH$_4$ (4 mg, 0.1 mmol) was added to a solution of N-tert-butyl carbamate-5-methoxy-6-chloro-2,3,3a,8a-tetrahydro-1H-2-aza-cyclopenta[a]inden-8-one (from Example 52, Step D, regioisomer) (20 mg, 0.06 mmol) in MeOH (2 mL), and stirred for 1 hour at room temperature. The reaction was partitioned between H$_2$O and CH$_2$Cl$_2$, and filtered through an Extrelut column. The column was washed with CH$_2$Cl$_2$, and the filtrate was concentrated. The crude product was obtained without further purification as a mixture of diastereomers. MS calculated for $C_{17}H_{22}ClNO_4$+H: 340, observed: 340.

Step B. 5-Methoxy-6-chloro-2,3,3a,8a-tetrahydro-1H-2-aza-cyclopenta[a]inden-8-ol.

The title compound was prepared by the method of Example 20, Step I utilizing N-tert-butyl carbamate-4-chloro-5-methoxy-2,3,3a,8a-tetrahydro-1H-2-aza-cyclopenta[a]inden-8-ol (0.10 mmol). The crude product was purified by reverse-phase liquid chromatography to afford the title compound. MS calculated for $C_{12}H_{12}ClNO_2$+H: 240, observed: 240.

Example 56

Separation of Enantiomers for Selected Compounds of the Invention

The following compounds were separated into their respective enantiomers using a 10 mm×250 mm Chiral Pak AD-RH chiral column.

The following procedure was utilized to evaluate representative compounds of the present invention as $5HT_{2c}$ receptor agonists. The results of this assay are set forth in Table 1.

Cell Culture

HEK 293 EBNA expressing the human 5HT2c receptor (VSV Isoform; Burns et al., NATURE 387:30308, 1997) were grown in DMEM containing 10% dialysed FBS, 9 μg/ml blasticidin at 37° C. in 5% CO$_2$ atmosphere.

Calcium Mobilization

HEK 293 EBNA cells expressing human $5HT2_c$ receptor (2×10$^4$/well) were seeded in black 384-well collagen coated plates and incubated overnight at 37° C. in a 5% CO2/95% atmosphere. After removing medium, cells were treated with HBSS buffer (137 mM NaCl, 5.4 mM KCl, 5.5 mM Glucose, 20 mM Hepes, pH 7.5, 2.1 mM MgCl$_2$, 0.3 mM CaCl$_2$, 0.02 mM MgSO$_4$, 3.0 mM NaHCO$_3$, and 0.64 mM KH$_2$PO$_4$) containing the Calcium3 dye (Molecular Device, CA), 2.5 mM probenecid and 0.08% pluronic acid for 60 minutes according to manufacture's instruction. Compounds that were solubilized in 100% DMSO were diluted in CsCl Ringers buffer (58.3 mM CsCl, 5.4 mM KCl, 5.5 mM Glucose, 20 mM Hepes, pH 7.5, 2.1 mM MgCl$_2$, 1.2 mM CaCl$_2$) such that the final DMSO concentration did not exceed 5%. 5HT was utilized as a positive control. Ligand induced calcium release and consequent fluorescence was measured on a Fluorometric Imaging Plate Reader (FLIPR, Molecular Device, CA).

Data Analysis

All data were analyzed by nonlinear least square curve fitting using Prism 4.0 software. Agonist stimulation of calcium-induced fluorescence in FLIPR was fitted to sigmoidal dose response using equation Y=Bottom+(Top−Bottom)/(1+10^((LogEC50−X))), where X is the logarithm of concentration of compounds and Y is the fluorescent response.

| Compound | Column Conditions | Enantiomer | Retention Time (minutes) | Final Products Derived from Enantiomer |
|---|---|---|---|---|
| Example 2, Step A | H$_2$O:CH$_3$CN (55:45) | 1 | 13.70 | 2, 5, 38 |
| | 2.6 mL/min | 2 | 19.24 | 1, 2, 3, 4, 5, 6, 25, 29, 30, 31, 32, 33, 38, 43, 44, 45, 46, 47, 50 |
| Example 21, Step A | H$_2$O:CH$_3$CN (50:50) | 1 | 30.57 | 21 |
| | 2.0 mL/min | 2 | 32.70 | 21 |
| Example 23, Step A | H$_2$O:CH$_3$CN (40:60) | 1 | 17.34 | 15, 23 |
| | 2.0 mL/min | 2 | 21.49 | 15, 23 |
| Example 26, Step H | H$_2$O:CH$_3$CN (40:60) | 1 | 28.47 | 26 |
| | 2.0 mL/min | 2 | 31.17 | 26 |
| Example 27, Step D | MeOH | 1 | 10.30 | 27 |
| | 10.0 mL/min | 2 | 12.13 | 27 |
| Example 34, Step F | H$_2$O:CH$_3$CN (50:50) | 1 | 23.02 | 34, 35 |
| | 1.8 mL/min | 2 | 26.44 | 34, 35 |
| Example 36, Step F | H$_2$O:CH$_3$CN (45:55) | 1 | 16.00 | 36 |
| | 1.8 mL/min | 2 | 23.25 | 36 |
| Example 37, Step D | H$_2$O:CH$_3$CN (45:55) | 1 | 20.42 | 37 |
| | 1.8 mL/min | 2 | 28.95 | 37 |
| Example 41, Step H | MeOH | 1 | 9.92 | 41 |
| | 10.0 mL/min | 2 | 10.75 | 41 |
| Example 42, Step H | MeOH | 1 | 8.05 | 42 |
| | 10.0 mL/min | 2 | 11.72 | 42 |

| Example Number | Molecule | 5-HT2c EC50 (hVSV, μM) |
|---|---|---|
| 1<br>1, Enantiomer 2 | 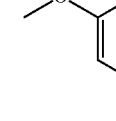 | >10<br><1 |
| 2<br>2, Enantiomer 1<br>2, Enantiomer 2 | 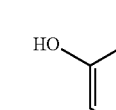 | <0.1<br><1<br><0.1 |
| 3<br>3, Enantiomer 2 | 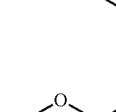 | <0.1<br><0.1 |
| 4<br>4, Enantiomer 2 | 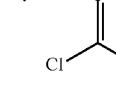 | <1<br><0.1 |
| 5<br>5, Enantiomer 1<br>5, Enantiomer 2 | 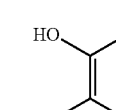 | <0.1<br><1<br><1 |
| 6<br>6, Enantiomer 2 | 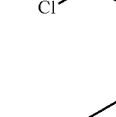 | <1<br><1 |
| 7 | 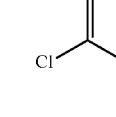 | <10 |
| 8 | 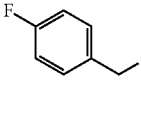 | <10 |
| 9 | 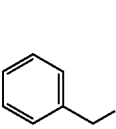 | <10 |
| 10 | 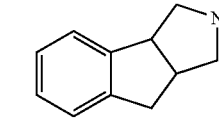 | <10 |
| 11 | 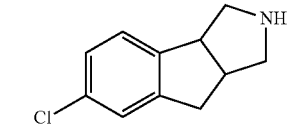 [SMILES: Clc1ccc2c(c1)CC1CNCC21] | <0.1<br><0.1<br><0.1 |
| 12 | 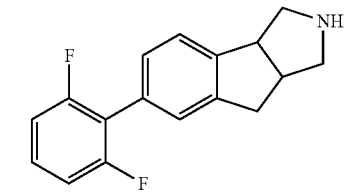 [SMILES: Fc1cccc(F)c1-c1ccc2c(c1)CC1CNCC21] | >10 |
| 13 | 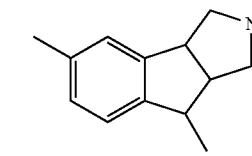 | <1 |
| 14 | 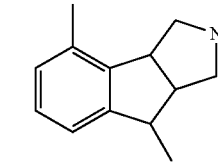 | <1 |
| 15<br>15, Enantiomer 1<br>15, Enantiomer 2 | 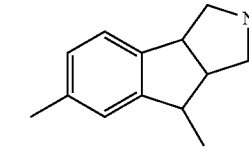 | <1<br><0.1<br><1 |
| 16 | 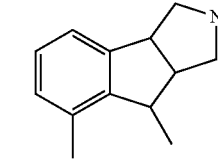 | <1 |
| 17 | 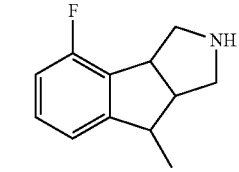 | <10 |
| 18 | 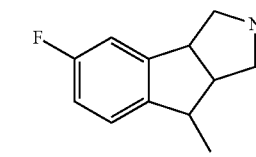 | <1 |

-continued

| Example Number | Molecule | 5-HT2c EC50 (hVSV, μM) |
|---|---|---|
| 19 | 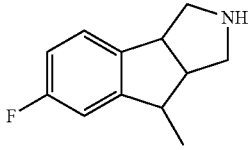 | <1 |
| 20 | 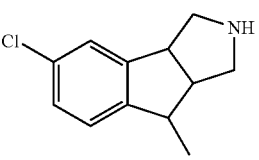 | <10 |
| 21<br>21, Enantiomer 1<br>21, Enantiomer 2 | 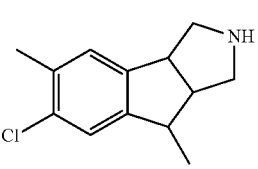 | <0.1<br><1<br><0.1 |
| 22 | 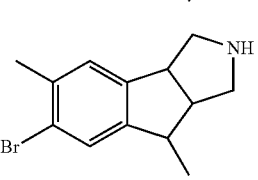 | <1 |
| 23<br>23, Enantiomer 1<br>23, Enantiomer 2 | 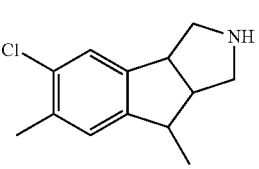 | <1<br><1<br><0.1 |
| 24 | 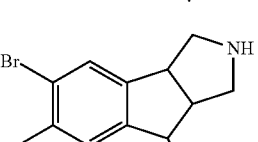 | <1 |
| 25, Enantiomer 2 | 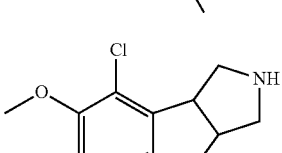 | <1 |
| 26<br>26, Enantiomer 1<br>26, Enantiomer 2 | 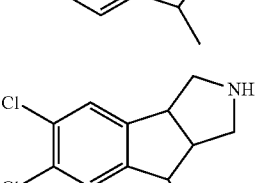 | <0.1<br><1<br><0.1 |
| 27<br>27, Enantiomer 1<br>27, Enantiomer 2 | 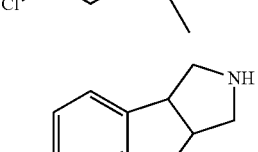 | <0.1<br><1<br><0.1 |

-continued

| Example Number | Molecule | 5-HT2c EC50 (hVSV, μM) |
|---|---|---|
| 28 | 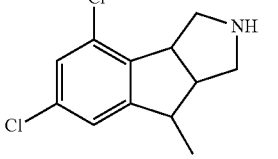 | <0.1 |
| 29, Enantiomer 2 | 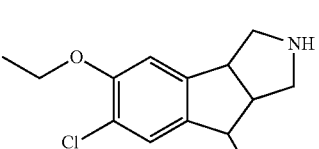 | <0.1 |
| 30, Enantiomer 2 | 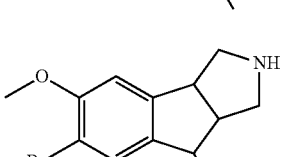 | <0.01 |
| 31, Enantiomer 2 | 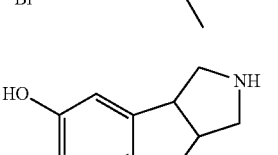 | <0.1 |
| 32, Enantiomer 2 | 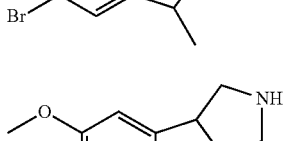 | >10 |
| 33, Enantiomer 2 | 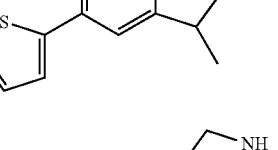 | <1 |
| 34, Enantiomer 1<br>34, Enantiomer 2 | 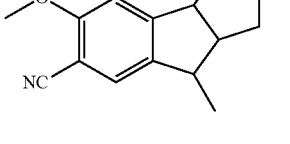 | <1<br><1 |
| 35, Enantiomer 1<br>35, Enantiomer 2 | 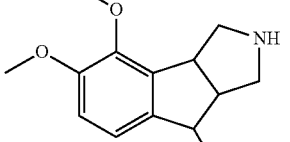 | <0.1<br><0.1 |

-continued
| Example Number | Molecule | 5-HT2c EC50 (hVSV, μM) |
|---|---|---|
| 36, Enantiomer 1 | | >10 |
| 36, Enantiomer 2 | | <1 |
| 37, Enantiomer 1 | | <0.1 |
| 37, Enantiomer 2 | | <0.1 |
| 38 | | <0.1 |
| 38, Enantiomer 1 | | <1 |
| 38, Enantiomer 2 | | <0.1 |
| 39 | | <1 |
| 40 | | >10 |
| 41, Enantiomer 1 | | <1 |
| 41, Enantiomer 2 | | <10 |
| 42, Enantiomer 1 | | <10 |
| 42, Enantiomer 2 | | <0.1 |
| 43, Enantiomer 2 | | <10 |
| 44, Enantiomer 2 | | <10 |
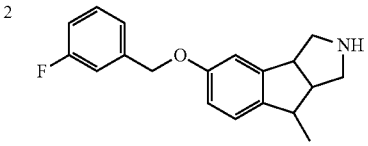
-continued
| Example Number | Molecule | 5-HT2c EC50 (hVSV, μM) |
|---|---|---|
| 45, Enantiomer 2 | | <10 |
| 46, Enantiomer 2 | | <10 |
| 47, Enantiomer 2 | | >10 |
| 48 | | >10 |
| 53 | | <1 |
| 54 | | <1 |
| 55 | | <10 |
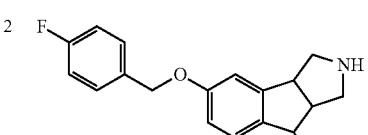

The invention claimed is:
1. A compound of the formula

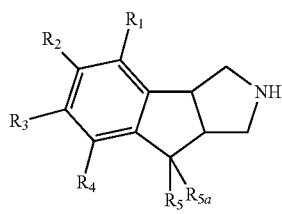

where
$R_1$ is selected from the group consisting of H, halogen, $C_{1-10}$alkyl, $C_{2-10}$ alkenyl, $C_{2-10}$ alkynyl, perhaloalkyl, CN, $N(R_6)_2$, $SR_6$, $CON(R_6)_2$, $NR_6COR_7$, $NR_6CO_2R_7$, $SO_2N(R_6)_2$, $NR_6SO_2R_7$, aryl, heteroaryl, $C_{1-10}$alkylaryl, and $C_{1-10}$alkylheteroaryl;
$R_2$ is selected from the group consisting of halogen, $C_{1-10}$alkyl, $C_{2-10}$ alkenyl, $C_{2-10}$ alkynyl, perhaloalkyl, CN, $OR_6$, $N(R_6)_2$, $SR_6$, $OCOR_7$, $CON(R_6)_2$, $NR_6COR_7$, $NR_6CO_2R_7$, $SO_2N(R_6)_2$, $NR_6SO_2R_7$, aryl, heteroaryl, $C_{1-10}$ alkylaryl, and $C_{1-10}$alkylheteroaryl; and $R_2$ may also be H when $R_5$ is $C_{1-10}$ alkyl or $R_4$ is H;
$R_3$ is selected from the group consisting of halogen, $C_{1-10}$alkyl, $C_{2-10}$ alkenyl, $C_{2-10}$ alkynyl, perhaloalkyl, CN, $OR_6$, $N(R_6)_2$, $SR_6$, $OCOR_7$, $CON(R_6)_2$, $NR_6COR_7$, $NR_6CO_2R_7$, $SO_2N(R_6)_2$, $NR_6SO_2R_7$, aryl, heteroaryl, $C_{1-10}$ alkylaryl, and $C_{1-10}$alkylheteroaryl;
$R_4$ is selected from the group consisting of H, halogen, $C_{1-10}$alkyl, $C_{2-10}$ alkenyl, $C_{2-10}$ alkynyl, perhaloalkyl, CN, $N(R_6)_2$, $SR_6$, $CON(R_6)_2$, $NR_6COR_7$, $NR_6CO_2R_7$, $SO_2N(R_6)_2$, $NR_6SO_2R_7$, aryl, heteroaryl, $C_{1-10}$ alkylaryl, and $C_{1-10}$alkylheteroaryl;
$R_5$ is selected from the group consisting of $C_{1-10}$ alkyl and $C_{2-10}$ alkenyl;
$R_{5a}$ is H;
$R_6$ is selected from the group consisting of H, $C_{1-10}$ alkyl, $C_{2-10}$ alkenyl, $C_{2-10}$ alkynyl, perhaloalkyl, $C_{1-10}$ alkyl-O—$C_{1-10}$ alkyl, aryl, heteroaryl, $C_{1-10}$alkyl-0-aryl, $C_{1-10}$ alkyl-O-heteroaryl, $C_{1-10}$ alkylaryl, and $C_{1-10}$ alkylheteroaryl; and
$R_7$ is selected from the group consisting of $C_{1-10}$ alkyl, $C_{2-10}$ alkenyl, $C_{2-10}$ alkynyl, perhaloalkyl, $C_{1-10}$alkyl-O—$C_{1-10}$ alkyl, aryl, heteroaryl, $C_{1-10}$alkyl-O-aryl, $C_{1-10}$alkyl-O-heteroaryl, $C_{1-10}$ alkylaryl, and $C_{1-10}$ alkylheteroaryl;
or a pharmaceutically acceptable salt thereof.

2. A pharmaceutical composition comprising at least one compound of claim 1 and a pharmaceutically acceptable carrier.

3. The compound according to claim 1 having formula:

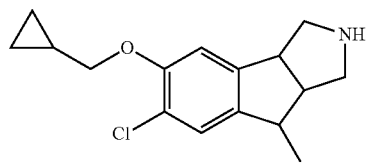

4. The compound according to claim 1 having formula:

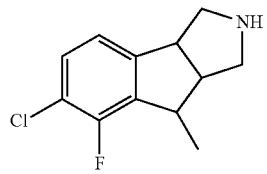

5. A pharmaceutical composition comprising the compound of claim 3 and a pharmaceutically acceptable carrier.

6. A pharmaceutical composition comprising the compound of claim 4 and a pharmaceutically acceptable carrier.

* * * * *